(12) United States Patent
Zeiller et al.

(10) Patent No.: US 7,678,831 B2
(45) Date of Patent: Mar. 16, 2010

(54) BUTANOIC ACID DERIVATIVES, PROCESSES FOR THE PREPARATION THEREOF, PHARMACEUTICAL COMPOSITIONS COMPRISING THEM, AND THERAPEUTIC APPLICATIONS THEREOF

(75) Inventors: Jean Jacques Zeiller, Lyons (FR); Hervè Dumas, Vaulx Milieu (FR); Valérie Guyard-Dangremont, Saint Maurice de Gourdans (FR); Isabelle Berard, Villard les Dombes (FR); Francis Contard, Lyons (FR); Daniel Guerrier, Saint Genis Laval (FR); Gérard Ferrand, Lyons (FR); Yves Bonhomme, Charbonnières les Bains (FR)

(73) Assignee: Merck Patent GmbH, Darmstadt (DE)

( * ) Notice: Subject to any disclaimer, the term of this patent is extended or adjusted under 35 U.S.C. 154(b) by 355 days.

(21) Appl. No.: 11/579,362

(22) PCT Filed: Apr. 6, 2005

(86) PCT No.: PCT/EP2005/003607

§ 371 (c)(1),
(2), (4) Date: Nov. 2, 2006

(87) PCT Pub. No.: WO2005/105764

PCT Pub. Date: Nov. 10, 2005

(65) Prior Publication Data

US 2008/0032982 A1 Feb. 7, 2008

(30) Foreign Application Priority Data

May 3, 2004 (FR) .................................. 04 04711

(51) Int. Cl.
  *A61K 31/19* (2006.01)
  *C07C 65/00* (2006.01)
(52) U.S. Cl. ...................... 514/557; 562/405; 514/438; 549/29

(58) Field of Classification Search ................... 549/29; 562/405; 514/438, 557
See application file for complete search history.

(56) References Cited

U.S. PATENT DOCUMENTS

| 6,251,936 B1 * | 6/2001 | Wrobel et al. ............... 514/443 |
| 7,358,364 B2 * | 4/2008 | Van Zandt et al. ............ 546/85 |
| 2003/0055058 A1 | 3/2003 | Zhang et al. |
| 2005/0272788 A1 | 12/2005 | Acton, III et al. |

FOREIGN PATENT DOCUMENTS

| WO | WO 02/100398 A | 12/2002 |
| WO | WO 2004/019869 A | 3/2004 |

OTHER PUBLICATIONS

Van Zandt et al., 2004, CAS: 141:424429.*
Murthy et al., 2002, CAS: 137:319942.*
Patankar et al., 2003, CAS: 139:328.*
Greenlee et al., 1991, CAS: 115:256165.*
Wrobel et al., 2001, CAS: 135:61241.*

* cited by examiner

*Primary Examiner*—Rei-tsang Shiao
(74) *Attorney, Agent, or Firm*—Millen, White, Zelano, Branigan, P.C.

(57) ABSTRACT

Compounds of the formula (I): in which R, $R^1$ and $R^2$ are as defined in the description, the use thereof for the treatment of dyslipidaemia, atherosclerosis and diabetes, pharmaceutical compositions comprising them, and . processes for the preparation of these compounds. Compounds of formula (I) are activators of PPARα and PPARα isoforms.

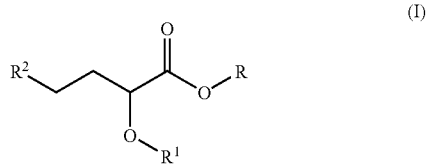

(I)

11 Claims, No Drawings

BUTANOIC ACID DERIVATIVES, PROCESSES FOR THE PREPARATION THEREOF, PHARMACEUTICAL COMPOSITIONS COMPRISING THEM, AND THERAPEUTIC APPLICATIONS THEREOF

The present invention relates to 4-substituted butanoic acid derivatives which can be used in the treatment of dyslipidaemia, atherosclerosis and diabetes, to pharmaceutical compositions comprising them, and to processes for the preparation of these compounds.

The invention also relates to the use of these compounds for the preparation of medicaments for the treatment of dyslipidaemia, atherosclerosis and diabetes.

In most countries, cardiovascular disease remains one of the major diseases and the main cause of death. About one third of men develop a major cardiovascular disease before the age of 60, with women showing a lower risk (ratio of 1 to 10). With advancing years (after the age of 65, women become just as vulnerable to cardiovascular diseases as men), this disease increases even more in scale. Vascular diseases, such as coronary disease, strokes, restenosis and peripheral vascular disease remain the prime cause of death and handicap worldwide.

Whereas the diet and lifestyle can accelerate the development of cardiovascular diseases, a genetic predisposition leading to dyslipidaemia is a significant factor in cardiovascular accidents and death.

The development of atherosclerosis appears to be linked mainly to dyslipidaemia, which means abnormal levels of lipoproteins in the blood plasma. This dysfunction is particularly evident in coronary disease, diabetes and obesity.

The concept intended to explain the development of atherosclerosis was mainly focused on the metabolism of cholesterol and on the metabolism of triglycerides.

However, since the studies of Randle et al. (Lancet, 1963, 785-789), a novel concept has been proposed: a glucose-fatty acid cycle or Randle cycle, which describes the regulation of the equilibrium between the metabolism of lipids in terms of triglycerides and cholesterol, and the oxygenation of glucose. Following this concept, the inventors have developed a novel programme, the aim of which is to find novel compounds acting simultaneously on lipid metabolism and glucose metabolism.

Fibrates are well-known therapeutic agents with a mechanism of action via the "Peroxisome Proliferator Activated Receptors" (PPARs). These receptors are the main regulators of lipid metabolism in the liver (PPARα isoform). In the last 10 years, thiazolidinediones have been described as powerful hypoglycaemiant agents in man and animals. It has been reported that thiazolidinediones are powerful selective activators of another isoform of PPARs: PPARγ (Lehmann et al., J. Biol. Chem., (1995), 270, 12953-12956).

The inventors have discovered a novel class of compounds that are powerful activators of the PPARα and PPARγ isoforms. As a result of this activity, these compounds have a substantial hypolipidaemiant and hypoglycaemiant effect.

More specifically, the invention relates to compounds derived from butanoic acid, of the formula (I) below:

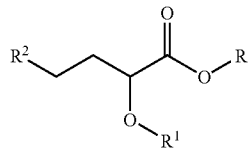

in which:
R is chosen from a hydrogen atom and a $C_1$-$C_{10}$ alkyl radical;
$R^1$ and $R^2$, which may be identical or different, are chosen such that:
A.—either:
$R^1$ is chosen from:
  a ($C_6$-$C_{18}$)aryl radical bearing from two to five identical or different substituents G;
  a ($C_6$-$C_{18}$)aryl radical bearing a substituent G, itself comprising an optionally substituted ($C_6$-$C_{18}$)aryl radical and/or a saturated, unsaturated or aromatic, optionally substituted 5- to 8-membered monocyclic heterocyclic radical containing one or more hetero atoms chosen from O, N and S;
  an optionally substituted ($C_6$-$C_{18}$)aryl radical, fused to a saturated or unsaturated 5- to 8-membered monocyclic or polycyclic nucleus optionally containing one or more hetero atoms chosen from oxygen and sulfur, the said nucleus itself being optionally substituted;
  an optionally substituted ($C_6$-$C_{18}$)aryl radical, fused to a saturated or unsaturated 6- to 8-membered monocyclic or polycyclic nucleus comprising at least one nitrogen atom as hetero atom, the said nucleus itself being optionally substituted; and
  a saturated, unsaturated or aromatic, optionally substituted 5- to 8-membered monocyclic heterocyclic radical containing one or more hetero atoms chosen from oxygen, nitrogen and sulfur;
and, in this case,
$R^2$ is chosen from:
  a ($C_6$-$C_{18}$)aryl radical, which is optionally substituted and/or optionally fused to a saturated or unsaturated 5- to 8-membered monocyclic or polycyclic nucleus optionally containing one or more hetero atoms chosen from O, N and S, the said nucleus itself being optionally substituted; and
  an optionally substituted 5- to 8-membered monocyclic aromatic heterocyclic radical containing one or more hetero atoms chosen from O, N and S;
B.—or:
$R^2$ is chosen from:
  a ($C_6$-$C_{18}$)aryl radical substituted by a ($C_6$-$C_{18}$)aryl radical, which is itself optionally substituted and/or optionally fused to a saturated or unsaturated 5- to 8-membered monocyclic or polycyclic nucleus optionally containing one or more hetero atoms chosen from O, N and S, the said nucleus itself being optionally substituted; and
  an optionally substituted 5- to 8-membered monocyclic aromatic heterocyclic radical containing one or more hetero atoms chosen from O, N and S;
and, in this case,
$R^1$ is chosen from:
  an optionally substituted ($C_6$-$C_{18}$)aryl radical fused to a saturated or unsaturated 5- to 8-membered monocyclic or polycyclic nucleus optionally containing one or more hetero atoms chosen from oxygen and sulfur, the said nucleus itself being optionally substituted;

an optionally substituted ($C_6$-$C_{18}$)aryl radical fused to a saturated or unsaturated 6- to 8-membered monocyclic or polycyclic nucleus bearing at least one nitrogen atom as hetero atom, the said nucleus itself being optionally substituted; and a saturated, unsaturated or aromatic, optionally substituted 5- to 8-membered monocyclic heterocyclic radical containing one or more hetero atoms chosen from oxygen, nitrogen and sulfur;

the optical isomers thereof, and the pharmaceutically acceptable addition salts thereof with acids or bases, with the restriction that when $R^2$ represents a phenyl radical not substituted by an aromatic or heteroaromatic radical, then $R^1$ cannot represent a phenyl radical that is itself substituted by a phenyl or naphthyl radical.

Such compounds have been disclosed in patents U.S. Pat. No. 3,378,582 and FR 1 476 525, which describe certain alkanoic acids bearing an aryl substituent, with hypocholesterolaemic activity.

The acids that can be used to form the salts of the compounds of the formula (I) are mineral or organic acids. The resulting salts are, for example, the hydrochlorides, hydrobromides, sulfates, hydrogen sulfates, dihydrogen phosphates, citrates, maleates, fumarates, 2-naphthalenesulfonates and para-toluenesulfonates.

The bases that can be used to form the salts of the compounds of the formula (I) are mineral or organic bases. The resulting salts are, for example, the salts formed with metals and especially alkali metals, alkaline-earth metals and transition metals (such as sodium, potassium, calcium, magnesium or aluminium), or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The invention especially covers the pharmaceutically acceptable salts, but also the salts that allow a suitable separation or crystallization of the compounds of the formula (I), such as the salts obtained with chiral amines.

The invention also covers the stereoisomers of the compounds of the formula (I), and also mixtures of stereoisomers in all proportions.

The compounds of the formula (I) above also include the prodrugs of these compounds.

The term "prodrugs" means compounds which, once administered to the patient, are chemically and/or biologically converted by the live organism into compounds of the formula (I).

According to the invention, the term "aryl radical" means a monocyclic or polycyclic carbocyclic aromatic radical preferably containing from 6 to 18 carbon atoms. Aryl radicals that may be mentioned include phenyl, naphthyl, anthryl and phenanthryl radicals.

The term "alkyl" means a linear or branched hydrocarbon-based chain containing from 1 to 10 carbon atoms and better still from 1 to 6 carbon atoms, for example from 1 to 4 carbon atoms.

Examples of alkyl radicals are methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

Unless otherwise mentioned, the heterocyclic radicals are monocyclic or polycyclic radicals comprising hetero atoms generally chosen from O, S and N, optionally in oxidized form (in the case of S and N).

Preferably, at least one of the monocycles constituting the heterocycle is comprises from 1 to 4 endocyclic hetero atoms and better still from 1 to 3 hetero atoms.

According to the invention, the polycyclic heterocyclic nucleus consists of one or more monocycles, each of which is 5- to 8-membered.

Examples of 5- to 8-membered monocyclic aromatic heterocyclic groups are heteroaryls, such as pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Preferred heteroaryl radicals that may be mentioned include pyridyl, pyrimidinyl, triazolyl, thiadiazolyl, oxazolyl, thiazolyl and thienyl radicals.

Among the heterocyclic groups defined above, examples of 5- to 8-membered monocyclic aromatic heterocyclic groups containing one or more hetero atoms chosen from oxygen and sulfur are heteroaryls, such as furan and thiophene.

Examples of 6- to 8-membered monocyclic aromatic heterocyclic groups containing at least one nitrogen atom as heterocycle are pyridine, thiazines (including thiadiazines and dithiazines), triazines, pyridazine, pyrazine and pyrimidine.

Preferred heteroaryl radicals that may be mentioned include pyridyl, pyrimidinyl, thiadiazolyl and thienyl radicals.

The saturated or unsaturated heterocyclic radicals are heterocyclic groups bearing no unsaturation, or comprising one or more unsaturations derived from the aromatic heterocyclic groups defined above, respectively. Included along with those are pyrans, thiopyrans, morpholine and thiomorpholine.

The term "$C_2$-$C_{10}$ alkenyl radical" means an aliphatic hydrocarbon-based radical containing one or more unsaturations of ethylenic type, preferably 1 to 3 ethylenic unsaturations. Preferred examples of such $C_2$-$C_{10}$ alkenyl groups are especially radicals chosen from vinyl and $CH_2$=CH—$CH_2$=CH— groups. The alkenyl radical is optionally substituted, preferably with one or more radicals chosen from carboxyl, ($C_1$-$C_6$)alkoxycarbonyl and phenyl.

The aryl and heterocyclic radicals may be optionally substituted by one or more of the following radicals G:

trifluoromethyl; styryl; a halogen atom; a monocyclic, bicyclic or tricyclic aromatic heterocyclic radical comprising one or more hetero atoms chosen from O, N and S; and optionally substituted by one or more radicals T as defined below; a group Het-CO—, in which Het represents an aromatic heterocyclic radical as defined above optionally substituted by one or more radicals T; a $C_1$-$C_6$ alkylenediyl chain; a $C_1$-$C_6$ alkylenedioxy chain; nitro; cyano; ($C_1$-$C_{10}$)alkyl; ($C_1$-$C_{10}$)alkylcarbonyl; ($C_1$-$C_{10}$)alkoxycarbonyl-A-, in which A represents ($C_1$-$C_6$)-alkylene, ($C_2$-$C_6$)alkenylene or a bond; ($C_3$-$C_{10}$)cycloalkyl; trifluoromethoxy; di($C_1$-$C_{10}$)alkylamino; ($C_1$-$C_{10}$)alkoxy($C_1$-$C_{10}$)alkyl; ($C_1$-$C_{10}$)alkoxy; ($C_6$-$C_{18}$)aryl optionally substituted by one or more radicals T; ($C_6$-$C_{18}$)aryl($C_1$-$C_{10}$)alkoxy-(CO)$_n$—, in which n is 0 or 1 and aryl is optionally substituted by one or more radicals T; ($C_6$-$C_{18}$)aryloxy(CO)$_n$—, in which n is 0 or 1 and in which aryl is optionally substituted by one or more radicals T; ($C_6$-$C_{18}$)arylthio, in which aryl is optionally substituted by one or more radicals T; $(C_6-C_{18})$aryloxy$(C_1-C_{10})$alkyl-$(CO)_n$—, in which n is 0 or 1 and in which aryl is optionally substituted by one or more radicals T; a saturated or unsaturated, monocyclic 5- to 8-membered heterocycle comprising one or more hetero atoms chosen from O, N and S, optionally substituted by one or more radicals T; $(C_6-C_{18})$arylcarbonyl optionally substituted by one or more radicals T; $(C_6-C_{18})$arylcarbonyl-B—$(CO)_n$—, in which n is 0 or 1; B represents $(C_1-C_6)$alkylene or $(C_2-C_6)$alkenylene and aryl is optionally substituted by one or more radicals T; $(C_6-C_{18})$aryl-C—$(CO)_n$—, in which n is 0 or 1, C represents $(C_1-C_6)$alkylene or $(C_2-C_6)$alkenylene and aryl is optionally substituted by one or more radicals T; $(C_6-C_{18})$aryl fused to a saturated or unsaturated heterocycle as defined above, optionally substituted by one or more radicals T; $(C_2-C_{10})$alkynyl; T is chosen from a halogen atom; $(C_6-C_{18})$aryl; $(C_1-C_6)$alkyl; $(C_1-C_6)$alkoxy; $(C_1-C_6)$alkoxy$(C_6-C_{18})$aryl; nitro; carboxyl; $(C_1-C_6)$alkoxycarboxyl; and T may represent oxo in the case where it substitutes a saturated or unsaturated heterocycle; or T represents $(C_1-C_6)$-alkoxycarbonyl$(C_1-C_6)$alkyl; or $(C_1-C_6)$alkylcarbonyl$((C_1-C_6)$alkyl$)_n$-, in which n is 0 or 1.

The term "halogen atom" means a chlorine, bromine, iodine or fluorine atom. The monocyclic, bicyclic or tricyclic aromatic heterocyclic radicals preferably comprise one or more hetero atoms generally chosen from O, S and N, optionally in oxidized form (in the case of S and N). Preferably, at least one of the monocycles constituting the heterocycle comprises from 1 to 4 endocyclic hetero atoms and better still from 1 to 3 hetero atoms.

Preferably, the heterocycle consists of one or more monocycles, each of which is 5- to 8-membered.

Examples of 5- to 8-membered monocyclic heteroaryls are especially pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Examples of bicyclic heteroaryls in which each monocycles is 5- to 8-membered are chosen from indolizine, indole, isoindole, benzofuran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazine (such as pyrazolo-1,3,4-triazine), pyrazolopyrimidine and pteridine.

Preferred heteroaryl radicals that may be mentioned include quinolyl, pyridyl, benzothiazolyl and triazolyl radicals.

The tricyclic heteroaryls in which each monocycle is 5- to 8-membered are chosen, for example, from acridine, phenazine and carbazole.

The term "alkylenediyl chain" means a divalent radical of linear or branched aliphatic hydrocarbon-based type derived from the alkyl groups defined above by stripping out a hydrogen atom. Preferred examples of alkylenediyl chains are chains —$(CH_2)_k$—, in which k represents an integer chosen from 2, 3, 4, 5 and 6 and >$C(CH_3)_2$ and —$CH_2$—$C(CH_3)_2$—$CH_2$— chains. The alkylenedioxy chains denote —O-Alk-O— chains, in which Alk represents linear or branched alkylene, it being understood that alkylene is as defined above for alkylenediyl. Preferred meanings of —O-Alk-O— are, for example, —O—$C(CH_3)_2$—O or —O—$CH_2$—$CH_2$—O—.

The term "alkenylene" defines an unsaturated alkylene chain containing one or more ethylenic unsaturations, preferably one to three ethylenic unsaturations. Examples of alkylene chains are —CH=CH— or —CH—CH—CH=CH—.

Examples of $C_3-C_{10}$ cycloalkyl radicals are especially cyclopropyl, cyclobutyl, cyclopentyl, cyclohexyl, cycloheptyl, cyclooctyl or cyclodecyl radicals.

Saturated or unsaturated, monocyclic 5- to 8-membered heterocycles are saturated, or unsaturated, derivatives of aromatic heterocycles.

Mention may be made more particularly of morpholine, piperidine, thiazolidine, oxazolidine, tetrahydrothienyl, tetrahydrofuryl, pyrrolidine, isoxazolidine, imidazolidine or pyrazolidine.

The term "alkynyl" means an aliphatic hydrocarbon-based group containing one or more unsaturations of acetylenic type. A preferred example is —C≡C—.

The compounds of the formula (I) that are preferred are those in which R represents a hydrogen atom, $R^1$ and $R^2$ being as defined previously, the optical isomers thereof, and also the pharmaceutically acceptable addition salts thereof with acids or bases, with the restriction that when $R^2$ represents a phenyl radical not substituted by an aromatic or heteroaromatic radical, then $R^1$ cannot represent a phenyl radical that is itself substituted by a phenyl or naphthyl radical.

Another preferred group of compounds of the invention consists of the compounds for which:

$R^1$ represents a $(C_6-C_{18})$aryl radical bearing a substituent G, itself comprising an optionally substituted $(C_6-C_{18})$aryl radical and/or a saturated, unsaturated or aromatic, optionally substituted 5- to 8-membered monocyclic heterocyclic radical containing one or more hetero atoms chosen from O, N and S; and $R^2$ is chosen from:
  a $(C_6-C_{18})$aryl radical, which is optionally substituted and/or optionally fused to a saturated or unsaturated 5- to 8-membered monocyclic or polycyclic nucleus optionally containing one or more hetero atoms chosen from O, N and S, the said nucleus itself being optionally substituted; and
  an optionally substituted 5- to 8-membered monocyclic aromatic heterocyclic radical containing one or more hetero atoms chosen from O, N and S;

R being as defined above, the optical isomers thereof, and the pharmaceutically acceptable addition salts thereof with acids or bases, with the restriction that when $R^2$ represents a phenyl radical not substituted by an aromatic or heteroaromatic radical, then $R^1$ cannot represent a phenyl radical that is itself substituted by a phenyl or naphthyl radical.

Another preferred group of compounds of the invention consists of the compounds for which:

$R^1$ represents an optionally substituted $(C_6-C_{18})$aryl radical fused to a saturated or unsaturated 5- to 8-membered monocyclic or polycyclic nucleus optionally containing one or more hetero atoms chosen from oxygen and sulfur, the said nucleus itself being optionally substituted; or alternatively fused to a saturated or unsaturated 6- to 8-membered monocyclic or polycyclic nucleus comprising at least one nitrogen atom as hetero atom, the said nucleus itself being optionally substituted; and $R^2$ is chosen from:
  a $(C_6-C_{18})$aryl radical, which is optionally substituted and/or optionally fused to a saturated or unsaturated 5- to 8-membered monocyclic or polycyclic nucleus optionally containing one or more hetero atoms chosen from O, N and S, the said nucleus itself being optionally substituted; and an optionally substituted 5- to 8-membered monocyclic aromatic heterocyclic radical containing one or more hetero atoms chosen from O, N and S;

R being as defined above, the optical isomers thereof, and the pharmaceutically acceptable addition salts thereof with acids or bases.

Another preferred group of compounds of the invention consists of the compounds for which:

$R^1$ represents a saturated, unsaturated or aromatic, optionally substituted 5- to 8-membered monocyclic heterocyclic radical containing one or more hetero atoms chosen from O, N and S; and $R^2$ is chosen from:

a ($C_6$-$C_{18}$)aryl radical, which is optionally substituted and/or optionally fused to a saturated or unsaturated 5- to 8-membered monocyclic or polycyclic nucleus optionally containing one or more hetero atoms chosen from O, N and S, the said nucleus itself being optionally substituted; and an optionally substituted 5- to 8-membered monocyclic aromatic heterocyclic radical containing one or more hetero atoms chosen from O, N and S;

R being as defined above, the optical isomers thereof, and the pharmaceutically acceptable addition salts thereof with acids or bases.

Another preferred group of compounds of the invention consists of the compounds for which:

$R^1$ represents a ($C_6$-$C_{18}$)aryl radical bearing from two to five identical or different substituents G; and $R^2$ is chosen from:

a ($C_6$-$C_{18}$)aryl radical, which is optionally substituted and/or optionally fused to a saturated or unsaturated 5- to 8-membered monocyclic or polycyclic nucleus optionally containing one or more hetero atoms chosen from O, N and S, the said nucleus itself being optionally substituted; and an optionally substituted 5- to 8-membered monocyclic aromatic heterocyclic radical containing one or more hetero atoms chosen from O, N and S;

R being as defined above, the optical isomers thereof, and the pharmaceutically acceptable addition salts thereof with acids or bases.

Compounds that are also preferred are those of the general formula (I) for which:

$R^2$ represents a ($C_6$-$C_{18}$)aryl radical substituted by a ($C_6$-$C_{18}$)aryl radical, which is itself optionally substituted and/or optionally fused to a saturated or unsaturated 5- to 8-membered monocyclic or polycyclic nucleus optionally containing one or more hetero atoms chosen from O, N and S, the said nucleus itself being optionally substituted; and $R^1$ is chosen from:

an optionally substituted ($C_6$-$C_{18}$)aryl radical fused to a saturated or unsaturated, 5- to 8-membered monocyclic or polycyclic nucleus optionally containing one or more hetero atoms chosen from oxygen and sulfur, the said nucleus itself being optionally substituted;

an optionally substituted ($C_6$-$C_{18}$)aryl radical fused to a saturated or unsaturated 6- to 8-membered monocyclic or polycyclic nucleus comprising at least one nitrogen atom as hetero atom, the said nucleus itself being optionally substituted; and a saturated, unsaturated or aromatic, optionally substituted 5- to 8-membered monocyclic heterocyclic radical containing one or more hetero atoms chosen from oxygen, nitrogen and sulfur;

R being as defined above, the optical isomers thereof, and the pharmaceutically acceptable addition salts thereof with acids or bases.

Another preferred group consists of the compounds of the general formula (I) for which:

$R^2$ represents an optionally substituted 5- to 8-membered monocyclic aromatic heterocyclic radical containing one or more hetero atoms chosen from O, N and S; and $R^1$ is chosen from:

an optionally substituted ($C_6$-$C_{18}$)aryl radical fused to a saturated or unsaturated 5- to 8-membered monocyclic or polycyclic nucleus optionally containing one or more hetero atoms chosen from oxygen and sulfur, the said nucleus itself being optionally substituted;

an optionally substituted ($C_6$-$C_{18}$)aryl radical fused to a saturated or unsaturated 6- to 8-membered monocyclic or polycyclic nucleus comprising at least one nitrogen atom as hetero atom, the said nucleus itself being optionally substituted; and a saturated, unsaturated or aromatic, optionally substituted 5- to 8-membered monocyclic heterocyclic radical containing one or more hetero atoms chosen from oxygen, nitrogen and sulfur;

R being as defined above, the optical isomers thereof, and the pharmaceutically acceptable addition salts thereof with acids or bases.

Another preferred group consists of the compounds of the general formula (I) for which:

$R^2$ represents an optionally substituted biphenyl radical; and $R^1$ is chosen from:

an optionally substituted ($C_6$-$C_{18}$)aryl radical fused to a saturated or unsaturated 5- to 8-membered monocyclic or polycyclic nucleus optionally containing one or more hetero atoms chosen from oxygen and sulfur, the said nucleus itself being optionally substituted;

an optionally substituted ($C_6$-$C_{18}$)aryl radical fused to a saturated or unsaturated 6- to 8-membered monocyclic or polycyclic nucleus comprising at least one nitrogen atom as hetero atom, the said nucleus itself being optionally substituted; and a saturated, unsaturated or aromatic, optionally substituted 5- to 8-membered monocyclic heterocyclic radical containing one or more hetero atoms chosen from oxygen, nitrogen and sulfur;

R being as defined above, the optical isomers thereof, and the pharmaceutically acceptable addition salts thereof with acids or bases.

Another preferred group consists of the compounds of the general formula (I) for which:

$R^2$ represents an optionally substituted halogenated biphenyl radical, preferably an optionally substituted 4'-halogenated biphenyl radical; and $R^1$ is chosen from:

an optionally substituted ($C_6$-$C_{18}$)aryl radical fused to a saturated or unsaturated 5- to 8-membered monocyclic or polycyclic nucleus optionally containing one or more hetero atoms chosen from oxygen and sulfur, the said nucleus itself being optionally substituted;

an optionally substituted ($C_6$-$C_{18}$)aryl radical fused to a saturated or unsaturated 6- to 8-membered monocyclic or polycyclic nucleus comprising at least one nitrogen atom as hetero atom, the said nucleus itself being optionally substituted; and a saturated, unsaturated or aromatic, optionally substituted 5- to 8-membered monocyclic heterocyclic radical containing one or more hetero atoms chosen from oxygen, nitrogen and sulfur;

R being as defined above, the optical isomers thereof, and the pharmaceutically acceptable addition salts thereof with acids or bases.

The compounds that are also preferred are those of the general formula (I) for which, when $R^1$ represents a substituted ($C_6$-$C_{10}$)aryl radical, the aryl nucleus is substituted by one or more radicals G chosen from:

trifluoromethyl; a halogen atom; styryl; a monocyclic, bicyclic or tricyclic aromatic heterocyclic radical comprising one or more hetero atoms chosen from O, N and S; and optionally substituted by one or more radicals T as defined below; a group Het-CO—, in which Het represents an aromatic heterocyclic group as defined above, optionally substituted by one or more radicals T; a $C_1$-$C_6$ alkylenediyl chain; a $C_1$-$C_6$ alkylenedioxy chain; amino; nitro; cyano; ($C_1$-$C_{10}$)-alkyl radical; ($C_2$-$C_6$)alkynyl radical; ($C_1$-$C_{10}$)alkylcarbonyl radical; ($C_1$-$C_{10}$)alkoxycarbonyl-A- radical, in which A represents ($C_1$-$C_6$)alkylene, ($C_2$-$C_6$)alkenylene radical or a bond; ($C_3$-$C_{10}$)cycloalkyl radical; trifluoromethoxy radical; di($C_1$-$C_{10}$)-alkylamino radical; ($C_1$-$C_{10}$)alkoxy($C_1$-$C_{10}$) alkyl radical; ($C_1$-$C_{10}$)alkoxy radical; ($C_6$-$C_{18}$)aryl radical optionally substituted by one or more radicals T; ($C_6$-$C_{18}$)aryl ($C_1$-$C_{10}$)alkoxy-(CO)$_n$— radical, in which n is 0 or 1 and in which aryl is optionally substituted by one or more radicals T; ($C_6$-$C_{18}$)aryloxy(CO)$_n$— radical, in which n is 0 or 1 and in which aryl is optionally substituted by one or more radicals T; ($C_6$-$C_{18}$)aryloxy(CO)$_n$—($C_2$-$C_6$)alkenyl radical, in which n is 0 or 1; ($C_6$-$C_{18}$)arylthio radical, in which aryl is optionally substituted by one or more radicals T; ($C_6$-$C_{18}$)aryloxy($C_1$-$C_{10}$)alkyl(CO)$_n$—, in which n is 0 or 1 and in which aryl is optionally substituted by one or more radicals T; a saturated or unsaturated, monocyclic 5- to 8-membered heterocycle comprising one or more hetero atoms chosen from O, N and S, optionally substituted by one or more radicals T; ($C_6$-$C_{18}$) arylcarbonyl radical optionally substituted by one or more radicals T; ($C_6$-$C_{18}$)arylcarbonyl-B—(CO)$_n$— radical, in which n is 0 or 1; B represents ($C_1$-$C_6$)alkylene or ($C_2$-$C_6$) alkenylene and aryl is optionally substituted by one or more radicals T; ($C_6$-$C_{18}$)aryl-C—(CO)$_n$— radical, in which n is 0 or 1, C represents ($C_1$-$C_6$)alkylene or ($C_2$-$C_6$)alkenylene and aryl is optionally substituted by one or more radicals T; ($C_6$-$C_{18}$)aryl radical fused to a saturated or unsaturated heterocycle as defined above, optionally substituted by one or more radicals T; ($C_2$-$C_{10}$)alkynyl radical; T is chosen from a halogen atom; ($C_6$-$C_{18}$)aryl; ($C_1$-$C_6$)alkyl; ($C_1$-$C_6$)alkoxy; nitro; carboxyl; ($C_1$-$C_6$)alkoxycarboxyl; and T may represent oxo in the case where it substitutes a saturated or unsaturated heterocycle; or alternatively T represents ($C_1$-$C_6$)alkoxycarbonyl($C_1$-$C_6$)alkyl; or ($C_1$-$C_6$)alkylcarbonyl(($C_1$-$C_6$) alkyl)$_n$-, in which n is 0 or 1.

More particularly, the preferred compounds are those of the formula (I) chosen from:
(2S)-2-[4-(5-chlorothien-2-yl)phenoxy]-4-phenylbutanoic acid;
2-{2-[3-(4-chlorophenyl)acryloyl]-4-methylphenoxy}-4-phenylbutanoic acid;
(2S)-2-[4-(benzo[b]thiophen-2-yl)phenoxy]-4-phenylbutanoic acid;
(2S)-2-[4-(benzo[b]thiophen-3-yl)phenoxy)-4-phenylbutanoic acid;
4-(2-fluorophenyl)-2-[4-(2-methylthiazol-4-yl)phenoxy] butanoic acid;
4-(4'-chlorobiphenyl-4-yl)-2-(4-nitrophenoxy)butanoic acid;
4-(4-fluorophenyl)-2-[4-(2-methylthiazol-4-yl)phenoxy] butanoic acid; and
(2S)-2-(4-furan-2-ylphenoxy)-4-phenylbutanoic acid.

The invention also relates to pharmaceutical compositions comprising a pharmaceutically effective amount of at least one compound of the formula (I) as defined above in combination with one or more pharmaceutically acceptable vehicles.

These compositions can be administered orally in the form of tablets, gel capsules or granules with immediate release or controlled release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrating agent, a lubricant, a colorant or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatine, shellac, hydroxypropylcellulose, hydroxypropylmethylcellulose, calcium citrate, dextrin and pectin, Examples of lubricants include magnesium stearate, talc, polyethylene glycol, silica and hardened plant oils. The colorant may be any of those permitted for used in medicaments. Examples of flavour enhancers include cocoa powder, mint in herb form, aromatic powder, mint in oil form, borneol and cinnamon powder. Obviously, the tablet or granule can be suitably coated with sugar, gelatine or the like.

An injectable form comprising the compound of the present invention as active principle is prepared, where appropriate, by mixing the said compound with a pH regulator, a buffer agent, a suspension agent, a solubilizer, a stabilizer, an isotonic agent and/or a preserving agent, and by converting the mixture into a form for intravenous, subcutaneous or intramuscular injection, according to a standard process. Where appropriate, the injectable form obtained can be freeze-dried via a standard process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilizers include castor oil solidified with polyoxyethylene, polysorbate 80, nicotinamide, polyethoxylated sorbitan monolaurate and the ethyl ester of castor oil fatty acid.

In addition, the stabilizer encompasses sodium sulfite, sodium metasulfite and ether, while the preserving agent encompasses methyl p-hydroxybenzoate, ethyl p-hydroxybenzoate, sorbic acid, phenol, cresol and chlorocresol.

The present invention also relates to the use of a compound of the formula (I) of the invention for the preparation of a medicament for the prevention of or treating dyslipidaemia, atherosclerosis and diabetes.

The effective administration doses and posologies of the compounds of the invention, intended for the prevention or treatment of a disease, disorder or condition caused by or associated with modulation of PPAR activity, depends on a large number of factors, for example on the nature of the inhibitor, the size of the patient, the aim of the desired treatment, the nature of the pathology to be treated, the specific pharmaceutical composition used and the observations and the conclusions of the treating physician.

For example, in the case of an oral administration, for example a tablet or a gel capsule, a possible suitable dosage of the compounds of the formula (I) is between about 0.1 mg/kg and about 100 mg/kg of body weight per day, preferably between about 0.5 mg/kg and about 50 mg/kg of body weight per day, more preferably between about 1 mg/kg and about 10 mg/kg of body weight per day and more preferably between about 2 mg/kg and about 5 mg/kg of body weight per day of active material.

If representative of body weights of 10 kg and 100 kg are considered in order to illustrate the oral daily dosage range that can be used and as described above, suitable dosages of the compounds of the formula (I) will be between about 1-10 mg and 1000-10 000 mg per day, preferably between about 5-50 mg and 500-5000 mg per day, more preferably between about 10.0-100.0 mg and 100.0-1000.0 mg per day and even more preferably between about 20.0-200.0 mg and about 50.0-500.0 mg per day of active material comprising a preferred compound.

These dosage ranges represent total amounts of active material per day for a given patient. The number of administrations per day at which a dose is administered can vary within wide proportions depending on pharmacokinetic and pharmacological factors, such as the half-life of the active material, which reflects its rate of catabolism and clearance, and also the minimum and optimum levels of the said active material, in blood plasma or in other bodily fluids, which are reached in the patient and which are required for therapeutic efficacy.

Many other factors should also be taken into consideration when determining the number of daily administrations and the amount of active material that should be administered in a single dosage intake. Among these other factors, and not the least of which, is the individual response of the patient to be treated.

The present invention also relates to a general process for the preparation of the compounds of the formula (I), by reaction of a compound of the formula (II) with an alcohol of the formula $R^1$—OH, according to the following reaction scheme:

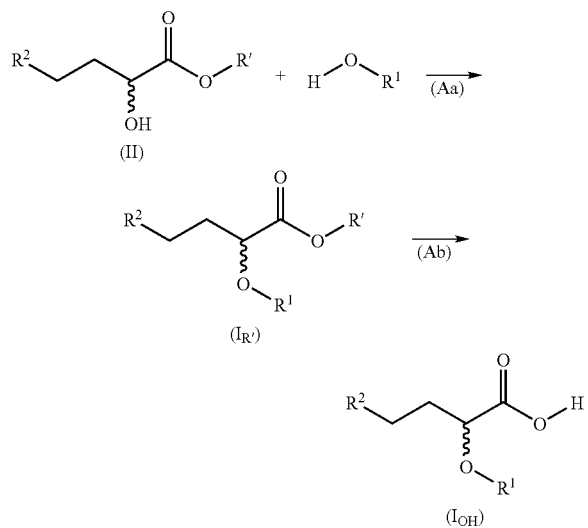

(Aa): THF/PPh$_3$/DIAD/room temp.
(Ab): EtOH/KOH/H$_2$O reflux in which reaction scheme $R^1$ and $R^2$ are as defined above for formula (I), R' represents R as defined above, with the exception of hydrogen, the compound ($I_{R'}$) being the compound of the formula (I) in which R represents a $C_1$-$C_{10}$ alkyl radical, as defined above, and the compound ($I_{OH}$) being the compound of the formula (I) in which R represents —H. THF means tetrahydrofuran. PPh$_3$ means triphenylphosphine, DIAD means diisopropyl azodicarboxylate, "room temp." means room temperature, EtOH is ethanol and KOH is potassium hydroxide.

The reaction step (Aa) is preferably performed in a polar aprotic solvent, such as a linear or cyclic ether of the type, such as diethyl ether, di-tert-butyl ether, diisopropyl ether or dimethoxyethane, or alternatively of the type, such as dioxane or tetrahydrofuran, tetrahydrofuran and dimethoxyethane being preferred.

According to one preferred embodiment of the invention, the molar ratio of the compound of the formula (II) to the alcohol $R^1$—OH ranges between 1 and 1.5, an approximately stoichiometric ratio of between 1 and 1.3 and preferably between 1 and 1.1 being desirable.

So as to facilitate the reaction, it is desirable to and to the medium a coupling agent, such as a lower alkyl (i.e. a $C_1$-$C_6$ alkyl) azodicarboxylate, for example diethyl azodicarboxylate (DEAD) or diisopropyl azodicarboxylate (DIAD).

When it is present in the reaction medium, the coupling agent is incorporated into the medium in a proportion of from 0.9 to 5 molar equivalents and better still in a proportion of from 0.9 to 3 molar equivalents, for example in a proportion of from 0.9 to 2 molar equivalents, relative to the initial amount of compound of the formula (II).

Preferably, it is also recommended to introduce a phosphine into the reaction medium, such as triphenylphosphine. In this case, the molar ratio of the triphenylphosphine to the compound of the formula (II) is preferably maintained between 0.9 and 5, for example between 0.9 and 3 and especially between 0.9 and 2.

The reaction temperature generally ranges between −15° C. and 60° C.

In the above reaction scheme, the saponification reaction step (Ab) is optional, i.e. it is performed only in the case where the desired compound of the formula (I) is a carboxylic acid (R=H).

In this case, the compounds of the formula (I) in which R represents H can advantageously be obtained by saponification of the corresponding compounds of the formula ($I_{R'}$). The saponification can be performed via the action of a base, such as a mineral base chosen from lithium hydroxide, potassium hydroxide, sodium hydroxide, sodium hydrogen carbonate, potassium hydrogen carbonate, sodium carbonate and potassium carbonate. The molar amount of base to be used generally ranges from 1 to 20 equivalents and preferably from 1 to 12 equivalents depending on the strength of the selected base.

More particularly, in the case of lithium hydroxide (LiOH), it is preferred to incorporate from 8 to 12 equivalents of base relative to the amount of ester of the formula (I) present in the reaction medium.

The reaction is preferably performed in a solvent of polar protic type and preferably in a mixture of lower ($C_1$-$C_4$) alkanol and water, such as a mixture of ethanol and water or of methanol and water.

The reaction temperature advantageously ranges between 20° C. and 120° C.

According to another embodiment of the process according to the invention, the compounds of the formula ($I_G$), which is a special case of the compounds of the formula (I) in which $R^1$ represents an aryl radical substituted by a radical G as defined above, can be prepared according to the following reaction scheme:

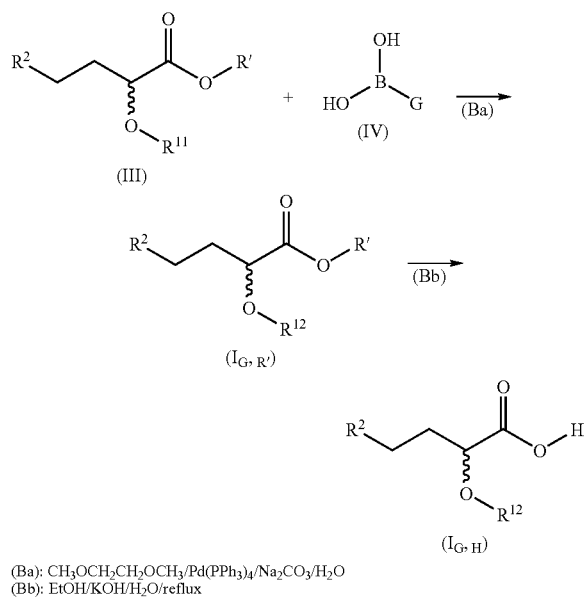

(Ba): CH$_3$OCH$_2$CH$_2$OCH$_3$/Pd(PPh$_3$)$_4$/Na$_2$CO$_3$/H$_2$O
(Bb): EtOH/KOH/H$_2$O/reflux in which reaction scheme:

R$^2$ is as defined above for formula (I);
R' represents R, as defined above, with the exception of hydrogen;
R$^{11}$ represents R$^1$, as defined above, bearing a group that is reactive with the derivative of the formula (IV) and chosen especially from a bromine or iodine atom and a CF$_3$SO$_3$— radical, bromine and iodine being the preferred reactive groups; and
R$^{12}$ represents R$^{11}$, in which the group that is reactive with the derivative of the formula (IV) has been substituted by the radical G.

As indicated in the above reaction schemes, the saponification step (Bb) is optional. The compounds of the formulae (I$_{G, R'}$) and (I$_{G, H}$) form the set of compounds of the formula (I$_G$), which is a special case of the compounds of the formula (I) in which R$^1$ represents an aryl radical substituted by a radical G.

Thus, the compounds of the formula (I) in which R$^1$ represents aryl substituted by a monocyclic, bicyclic or tricyclic aromatic heterocyclic group comprising one or more hetero atoms chosen from O, N and S, and optionally substituted by one or more radicals T as defined above, or alternatively in which R$^1$ represents an aryl group optionally substituted by one or more radicals T, can be prepared by reaction of the corresponding compound of the formula (III) defined above with a compound of the formula (IV) defined in the above reaction scheme, in which G represents a monocyclic, bicyclic or tricyclic aromatic heterocyclic group comprising one or more hetero atoms chosen from O, N and S, and optionally substituted by one or more radicals T as defined above when R$^1$, in the final compound, represents aryl substituted by such a heterocyclic group, or alternatively G represents aryl optionally substituted by one or more radicals T when, in the final compound, R$^1$ represents aryl substituted by an aryl group, which is itself optionally substituted by one or more radicals T.

Advantageously, from 1.5 to 5 equivalents and preferably from 1.5 to 3 equivalents of the compound of the formula (IV) are incorporated relative to the amount of compound of the formula (III) present in the reaction medium.

This reaction is preferably performed in a polar aprotic solvent in the presence of a palladium 0 complex and a base.

A linear or cyclic ether, such as those defined above is more particularly suitable as solvent. Dimethoxyethane is preferred.

The base that will be used is any of the mineral bases mentioned above and advantageously sodium carbonate. For example, from 1.5 to 5 equivalents and preferably from 1.5 to 3 equivalents of base, relative to the amount of compound of the formula (III), can be introduced into the reaction medium.

The amount of palladium 0 complex used is catalytic. Usually, from 0.001 to 1 equivalent and preferably from 0.01 to 0.1 equivalent of the said complex is used. An example of a palladium 0 complex that can be used is tetrakis(triphenylphosphine)palladium 0.

The reaction temperature advantageously ranges between 50° C. and 120° C. and preferably between 70° C. and 90° C.

The compounds of the formula (I) can also be prepared according to a synthetic route using compounds grafted onto resin, for example of Wang bromo type, according to the following reaction scheme:

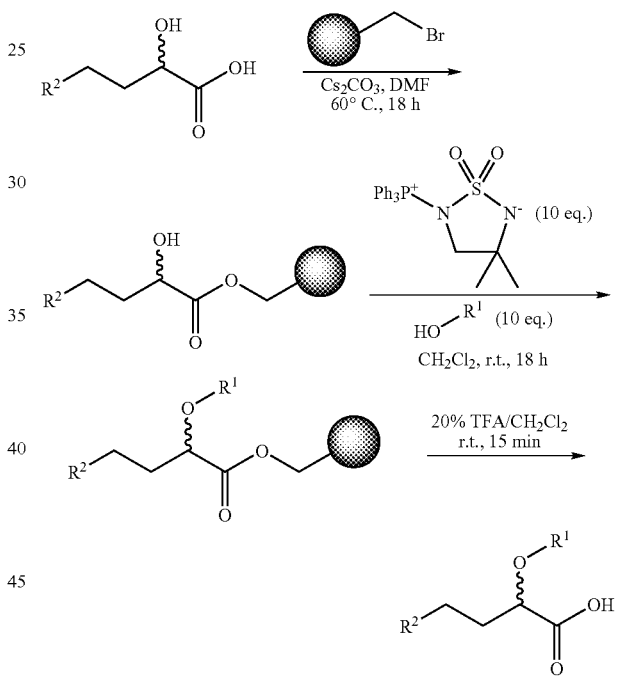

in which scheme R$^1$ and R$^2$ are as defined for the general formula (I).

In the above reaction scheme, caesium carbonate is added to a solution of α-hydroxy acid, in a solvent, for example a protic solvent, such as dimethylformamide, to which is then added a suspension of resin, so as to obtain the α-hydroxy acid derivative grafted onto resin.

To this derivative is then added the alcohol R$^1$—OH in the presence of a phosphine, such as 4,4-dimethyl-2-(triphenylphosphanyl)-1,2,5-thiadiazolidine. The reaction is performed, generally at room temperature, for a time that can range from one to several hours, for example about 18 hours.

The compound is then detached from the resin, according to standard techniques, for example using trifluoroacetic acid, to give the carboxylic acid obtained in the final step of the above reaction scheme. This carboxylic acid is a special case of the compound of the formula (I) in which R represents hydrogen, and can optionally be readily converted into a compound of the formula (I) in which R has the definition indicated previously for all the compounds according to the invention, with the exception of hydrogen, via any method known per se.

In the processes described above, it should be understood that the operating conditions can vary substantially depending on the various substituents present in the compounds of the formula (I) that it is desired to prepare. Such variations and adaptations are readily available to a person skilled in the art, for example from scientific reviews, the patent literature, Chemical Abstracts, and computer databases, including the Internet. Similarly, the starting materials are either commercially available or are available via syntheses that a person skilled in the art can readily find, for example in the various publications and databases described above.

The optical isomers of the compounds of the formula (I) can be obtained, on the one hand, via standard techniques for separating and/or purifying isomers, known to those skilled in the art, from the racemic mixture of the compound of the formula (I). The optical isomers can also be obtained directly via stereoselective synthesis of an optically active starting compound. The following reaction scheme gives an illustration of an example of a stereoselective synthesis using an optically active starting compound:

Example 1

Process for the Preparation of methyl 2-[4-(2-methyl-1,3-thiazol-4-yl)phenoxy]-4-(4-fluorophenyl) butanoate 6.7 mmol of diisopropyl azodicarboxylate dissolved in 5 ml of toluene are added dropwise over 45 minutes to a suspension, under a nitrogen atmosphere, of 7 mmol of methyl 4-(4-fluorophenyl)-2-hydroxybutanoate, 6.3 mmol of 4-(2-methyl-1,3-thiazol-4-yl)phenol and 6.9 mmol of triphenylphosphine in 50 ml of toluene, heated to 54° C.±3° C.

The solution obtained is maintained at this temperature for 1 hour, cooled to room temperature and stirred overnight.

The insoluble material formed is filtered off by suction, washed with 5 ml of ice-cold toluene and then discarded. The filtrate is evaporated under vacuum and the viscous residue is chromatographed on a column of silica, eluting with 90/10 heptane/ethyl acetate.

A small amount of triphenylphosphine is recovered in the first fraction.

The expected product constitutes the second fraction, in the form of a pale yellow oil that crystallizes.

Yield: 52%.

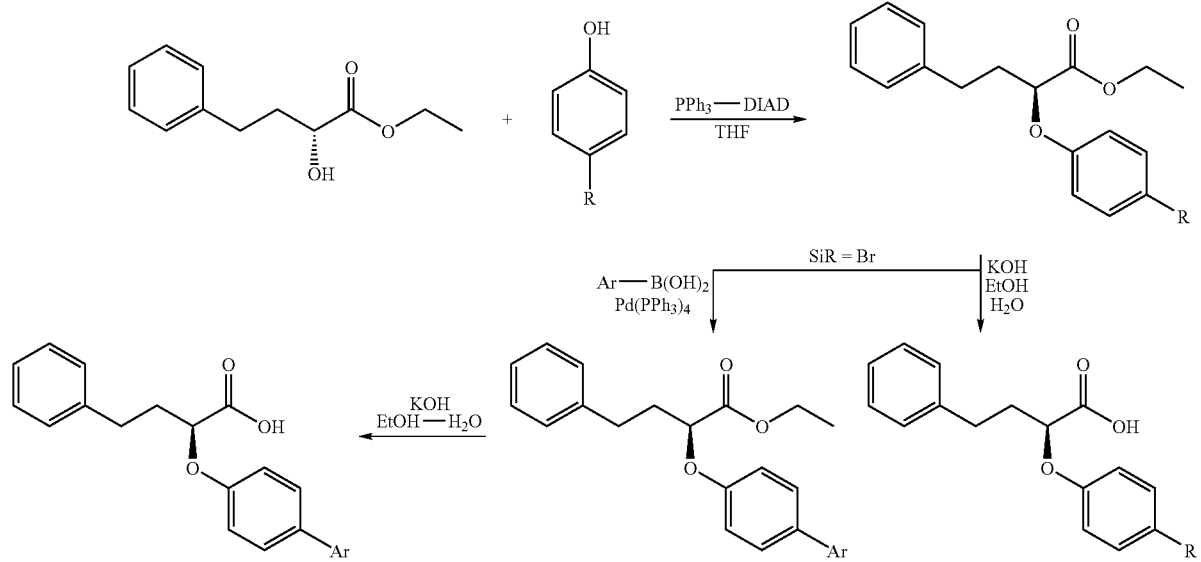

EXAMPLES

The examples that follow illustrate the present invention without limiting it in any way. In these examples and in the proton nuclear magnetic resonance (300 MHz NMR) data, the following abbreviations have been used: s for singlet, d for doublet, t for triplet, q for quartet, o for octet and m for complex multiplet. The chemical shifts δ are expressed in ppm. "MW" means molecular weight and "m.p." means "melting point".

Example 2

Process for the Preparation of 2-[4-(2-methyl-1,3-thiazol-4-yl)phenoxy]-4-(4-fluorophenyl)butanoic acid (Example 145 of the Table)

36 ml (36 mmol) of aqueous 1 M lithium hydroxide monohydrate solution are added dropwise over 30 minutes to a solution of 3.6 mmol of the compound obtained in Example 1, in 100 ml of methanol. The reaction is slightly exothermic.

The mixture is then stirred for 2 hours at room temperature, after which the solvents are evaporated off to dryness under vacuum.

The white solid residue obtained is taken up in 200 ml of water. The resulting suspension is stirred for 30 minutes and then acidified with 1/2 hydrochloric acid (HCl). Stirring is continued for 30 minutes and the medium is then extracted with ethyl acetate, with continued stirring until dissolution is complete.

After separation of the phases by settling, the organic phase is dried over sodium sulfate and then evaporated to dryness under vacuum, to give the expected product in the form of a white solid melting above 260° C.

Yield: 95%.

M.p.: >260° C.

$^1$H NMR (300 MHz; DMSO-d6): 1.90-2.23 (2H, m); 2.59-2.89 (2H, m); 2.68 (3H, s); 4.21-4.39 (1H, m); 6.72-7.30 (6H, m); 7.62-7.84 (3H, m).

Example 3

Process for the Preparation of ethyl (2S)-2-[4-(furan-2-yl)phenoxy]-4-phenylbutanoate 0.024 mmol of tetrakis(triphenylphosphine)palladium, 12.3 mmol of 2-furanboronic acid and 7.5 ml of 2 M sodium carbonate solution are added to a solution of 6.15 mmol of ethyl (2S)-2-(4-bromophenoxy)-4-phenylbutanoate in 25 ml of dimethoxyethane. The mixture is refluxed for 2 hours. After cooling to room temperature, the mixture is taken up in water and extracted with ethyl acetate. The organic phase is dried over sodium sulfate ($Na_2SO_4$) and then evaporated to dryness under vacuum. 2.6 g of a brown oil are obtained. This oil is chromatographed with a 9/1 heptane/ethyl acetate mixture as eluent. 1.5 g of an oil that crystallizes are obtained.

Yield: 68%.

Example 4

Process for the Preparation of (2S)-2-[4-(furan-2-yl)phenoxy]-4-phenylbutanoic acid (Example 22 of the Table)

21.5 mmol of potassium hydroxide are added to a solution of 4.3 mmol of ethyl (2S)-2-(4-furan-2-ylphenoxy)-4-phenylbutanoate, obtained in the preceding example, in 30 ml of ethanol. The mixture is refluxed for 30 minutes, 15 ml of water are added and refluxing is continued for 3 hours 30 minutes. After cooling to room temperature, the ethanol is evaporated off under vacuum. The product is taken up in water and washed with ether. The aqueous phase is acidified with 10% hydrochloric acid. A white precipitate forms, which is extracted with ethyl acetate. The organic phase is dried over sodium sulfate and evaporated under vacuum. 1.2 g of a beige-coloured solid, that recrystallizes from a hexane/ethyl acetate mixture to give 1 g of a solid melting at 140-142° C., are obtained.

Yield: 72.5%.

$^1$H NMR (300 MHz; CDCl$_3$): 2.15-2.50 (2H, m); 2.73-3.05 (2H, m); 4.55-4.75 (1H, m), 6.32-6.63 (2H, m); 6.79-7.04 (2H, m); 7.07-7.76 (8H, m).

Example 5

Process for the Preparation of (E)-2-[4-(2-ethoxycarbonyl-vinyl)-2-methoxyphenoxy]-4-phenylbutanoic acid (Example 66 of the Table)

A 20% solution of caesium carbonate in water (23 ml, 14.4 mmol) is added to a solution of 2-hydroxy-4-phenylbutanoic acid (7 g, 3.8 mmol) in methanol (200 ml). After stirring for 10 minutes, the solvents are evaporated off and the residue is taken up in toluene, which is then evaporated off. The residue is taken up in dimethylformamide (DMF) (125 ml), and is then added to a suspension of resin (23.7 g, 18 mmol) in DMF (125 ml). The reaction is stirred for 18 hours at 60° C. The resin is then washed several times with tetrahydrofuran (THF) (3×150 ml, 2 minutes), 1/1 THF/H$_2$O (3×150 ml, 2 minutes), methanol (3×150 ml, 2 minutes), dichloromethane (3×150 ml, 2 minutes) and methanol (3×150 ml, 2 minutes). The resin is dried under vacuum at 50° C.

A solution of ethyl (E)-3-(4-hydroxy-2-methoxy)phenyl-pent-2-enoate (1 mmol) in dichloromethane (2 ml) is added to grafted resin (150 mg, 0.1 mmol). A solution of 4,4-dimethyl-2-(triphenylphosphanyl)-1,2,5-thiadiazo-li-dine (1 mmol) in dichloromethane (8 ml) is then added and the suspension is stirred at room temperature for 18 hours. The resin is filtered off and washed with DMF (5 ml), 50/50 DMF/H$_2$O (5 ml), methanol (2×5 ml) and 80/20 dichloromethane/dichloroethane (DCM/DCE) (3×5 ml). The resin is then treated with 20/80 trifluoroacetic acid/dichloromethane (TFA/DCM) solution for 15 minutes. The resin is filtered off and washed with dichloromethane (2×5 ml). The filtrate is evaporated to give 1.9 mg of an oil, which is purified by preparative LCMS (liquid chromatography/mass spectrometry).

Mass spectrometry: ES—: 383.3.

The examples that follow are obtained according to procedures similar to those that have just been presented in the preceding examples.

| Ex. | STRUCTURE | MW | M.p. | NMR DATA | MS DATA |
|---|---|---|---|---|---|
| 6 | 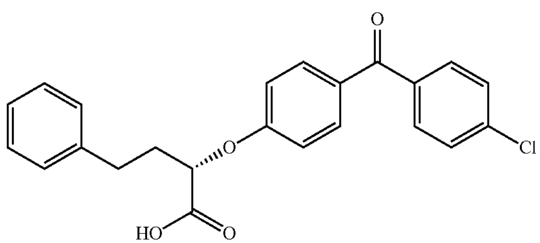 | 394.85 | 148° C. | ¹H NMR (300 MHz, CDCl₃) δ ppm: 2.19-2.51 (2 H, m); 2.71-3.05 (2 H, m); 4.58-4.81 (1 H, m); 6.81-7.01 (2 H, m); 7.07-7.34 (5 H, m); 7.34-7.55 (2 H, m); 7.60-7.90 (4 H, m). | |
| 7 | 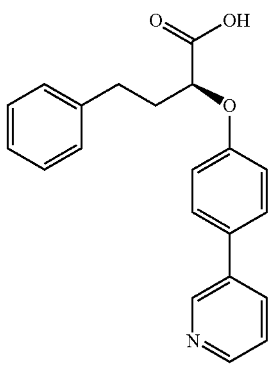 | 333.39 | 140° C. | ¹H NMR (300 MHz, CDCl₃) δ ppm: 2.42-2.78 (2 H, m); 2.96-3.34 (2 H, m); 4.77-5.00 (1 H, m); 7.11-7.81 (10 H, m); 8.05-8.28 (1 H, m); 8.61-8.84 (1 H, m); 8.87-9.09 (1 H, m); 11.27 (1 H, broad s). | |
| 8 | 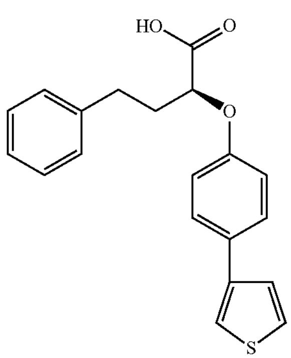 | 338.43 | 176-177° C. | ¹H NMR (300 MHz, CDCl₃) δ ppm: 1.98-2.42 (2 H, m); 2.60-2.99 (2 H, m); 4.40-4.70 (1 H, m); 6.69-6.92 (2 H, m); 6.96-7.58 (10 H, m); 8.70 (1 H, broad s). | |

-continued

| Ex. | STRUCTURE | MW | M.p. | NMR DATA | MS DATA |
|---|---|---|---|---|---|
| 9 | 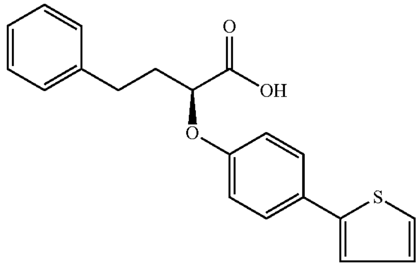 | 338.43 | 151-153° C. | ¹H NMR (300 MHz, CDCl₃) δ ppm: 2.14-2.48 (2 H, m); 2.71-3.04 (2 H, m); 4.52-4.73 (1 H, m); 6.79-6.96 (2 H, m); 6.97-7.10 (1 H, m); 7.11-7.37 (7 H, m); 7.44-7.61 (2 H, m). | |
| 10 | 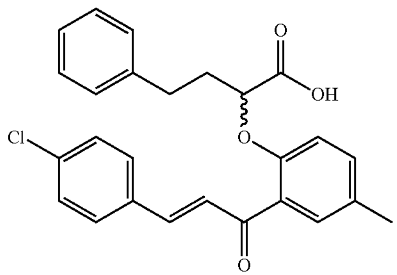 | 434.92 | | ¹H NMR (300 MHz, DMSO-d₆) δ ppm: 1.92-2.31 (5 H, m); 2.53-2.78 (2 H, m); 4.73-5.10 (1 H, m); 6.78-8.17 (14 H, m); 13.34 (1 H, broad s). | |
| 11 | 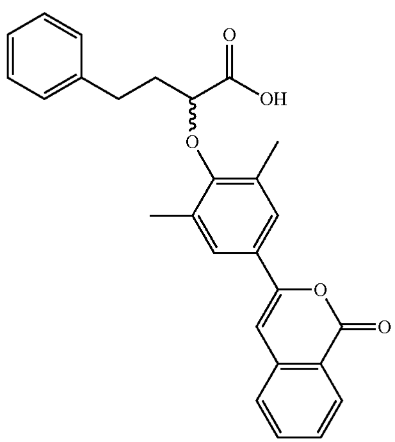 | 428.48 | | ¹H NMR (300 MHz, DMSO-d₆) δ ppm: 2.07-2.36 (5 H, m); 2.60-2.90 (2 H, m); 4.38-4.59 (1 H, m); 6.95-8.34 (12 H, m); 13.05 (1 H, broad s). | |

-continued

| Ex. | STRUCTURE | MW | M.p. | NMR DATA | MS DATA |
|---|---|---|---|---|---|
| 12 | 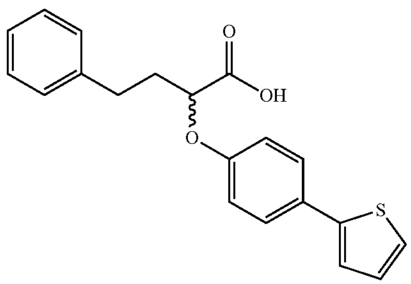 | 338.43 | | ¹H NMR (300 MHz, CDCl₃) δ ppm: 2.12-2.49 (2 H, m); 2.68-3.08 (2 H, m); 4.52-4.80 (1 H, m); 6.75-7.62 (12 H, m). | |
| 13 | 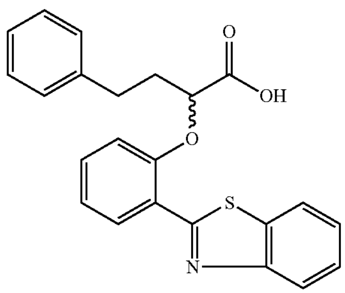 | 389.47 | | | ES+ 390.2 ES− 388.2 |
| 14 | 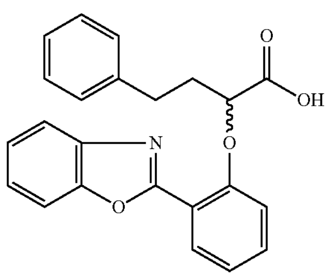 | 373.41 | | | ES+ 374.2 ES− 372.2 |

-continued

| Ex. | STRUCTURE | MW | M.p. | NMR DATA | MS DATA |
|---|---|---|---|---|---|
| 15 | 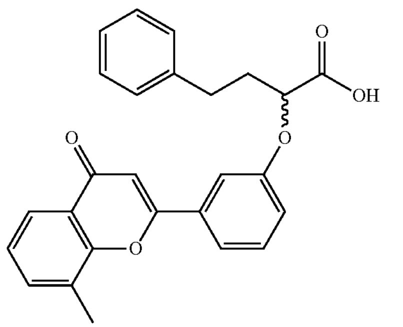 | 414.45 | | | ES+ M + H = 415.4 |
| 16 | 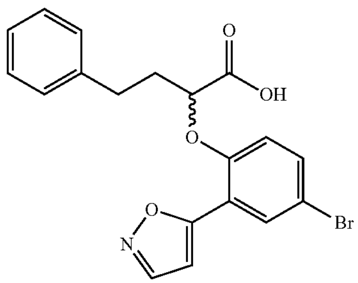 | 402.24 | | | ES+ M + H = 402.3<br>ES− M − H = 400.3<br>with 1 bromine |
| 17 | 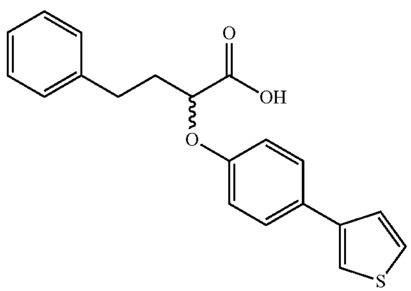 | 338.43 | 148-145° C. | $^1$H NMR (300 MHz, CDCl$_3$) δ ppm: 2.08-2.52 (2 H, m); 2.71-3.09 (2 H, m); 4.54-4.75 (1 H, m); 6.76-7.66 (12 H, m); | |

-continued
| Ex. | STRUCTURE | MW | M.p. | NMR DATA | MS DATA |
|---|---|---|---|---|---|
| 18 | 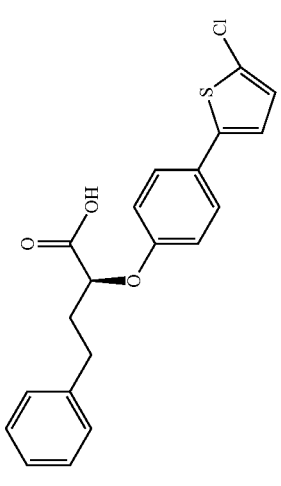 | 372.87 | | ¹H NMR (300 MHz, CDCl₃) δ ppm: 2.37-2.73 (2 H, m); 2.93-3.32 (2 H, m); 4.67-5.00 (1 H, m); 5.65 (1 H, broad s); 6.88-7.85 (11 H, m). | |
| 19 | 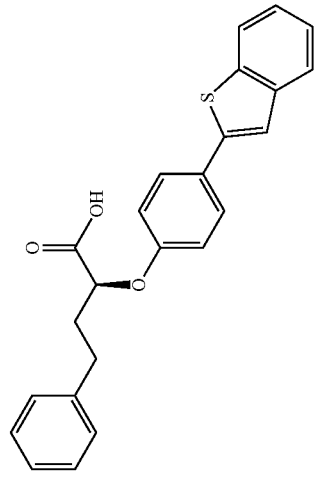 | 388.49 | | ¹H NMR (300 MHz, DMSO-d₆) δ ppm: 2.03-2.31 (2 H, m); 2.69-2.89 (2 H, m); 4.58-4.82 (1 H, m); 6.85-8.09 (14 H, m); 13.20 (1 H, broad s). | |
| 20 | 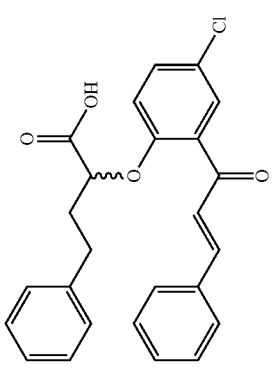 | 420.89 | | | AP + M + H = 387.3 |

-continued

| Ex. | STRUCTURE | MW | M.p. | NMR DATA | MS DATA |
|---|---|---|---|---|---|
| 21 | 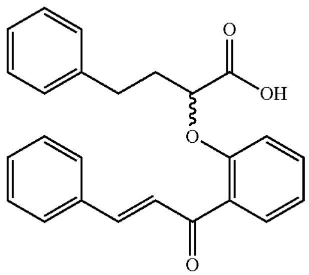 | 386.44 | | | AP + M + H = 421.3 with 1 chlorine |
| 22 | 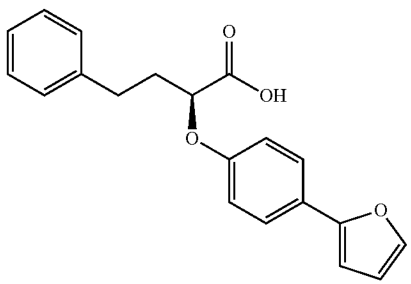 | 322.36 | 140–142° C. | ¹H NMR (300 MHz, CDCl₃) δ ppm: 2.15–2.50 (2 H, m); 2.73–3.05 (2 H, m); 4.55–4.75 (1 H, m); 6.32–6.63 (2 H, m); 6.79–7.04 (2 H, m); 7.07–7.76 (8 H, m). | |
| 23 | 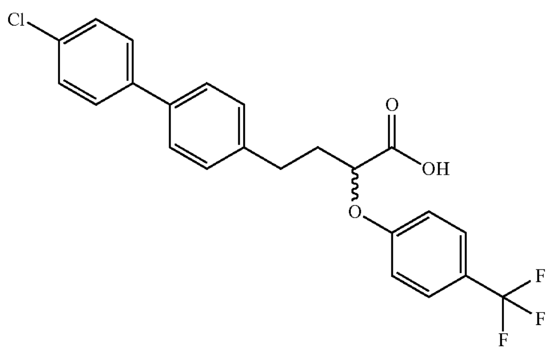 | 434.84 | | ¹H NMR (300 MHz, DMSO-d₆) δ ppm: 2.08–2.33 (2 H, m); 2.76–2.86 (2 H, m); 4.69–4.90 (1 H, m); 6.98–7.13 (2 H, m); 7.17–7.42 (2 H, m); 7.43–7.82 (8 H, m). | ES− 433.2/435.2 1 chlorine atom |

| Ex. | STRUCTURE | MW | M.p. | NMR DATA | MS DATA |
|---|---|---|---|---|---|
| 24 | 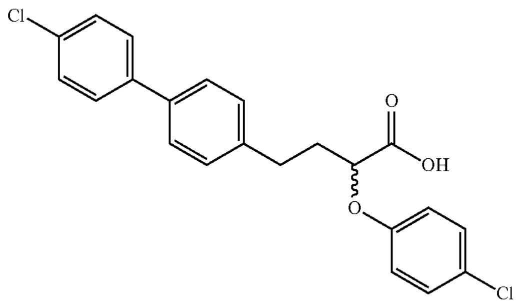 | 401.29 | | ¹H NMR (300 MHz, DMSO-d₆) δ ppm: 2.08-2.26 (2 H, m); 2.75-2.86 (2 H, m); 4.59-4.75 (1 H, m); 6.85-7.01 (2 H, m); 7.16-7.81 (10 H, m). | |
| 25 | 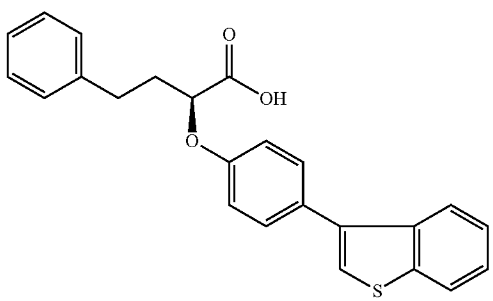 | 388.49 | | ¹H NMR (300 MHz, CDCl₃) δ ppm: 2.13-2.46 (2 H, m); 2.67-3.04 (2 H, m); 4.46-4.80 (1 H, m); 6.72-7.58 (12 H, m); 7.67-7.97 (2 H, m); 8.72 (1 H, broad s). | |
| 26 | 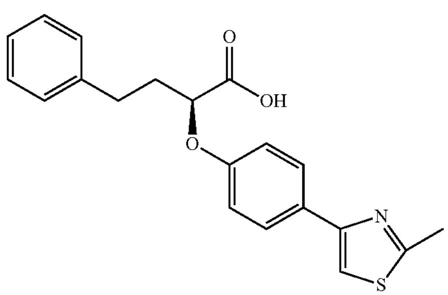 | 353.44 | 150-152° C. | ¹H NMR (300 MHz, CDCl₃) δ ppm: 2.2-2.49 (2 H, m); 2.76 (3 H, s); 2.80-3.08 (2 H, m); 4.54-4.70 (1 H, m); 6.83-6.99 (2 H, m); 7.10-7.35 (6 H, m); 7.64-7.81 (2 H, m). | |

-continued
| Ex. | STRUCTURE | MW | M.p. | NMR DATA | MS DATA |
|---|---|---|---|---|---|
| 27 | 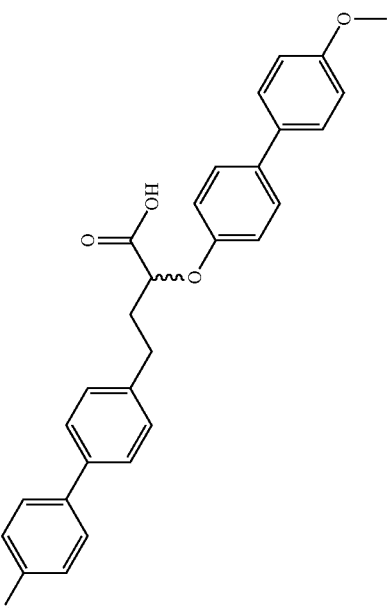 | 472.97 | | ¹H NMR (300 MHz, DMSO-d₆) δ ppm: 2.04-2.32 (2 H, m); 2.76-2.95 (2 H, m); 3.77 (3 H, s); 4.57-4.75 (1 H, m); 6.86-7.10 (4 H, m); 7.22-7.91 (12 H, m); 13.15 (1 H, broad s). | |
| 28 | 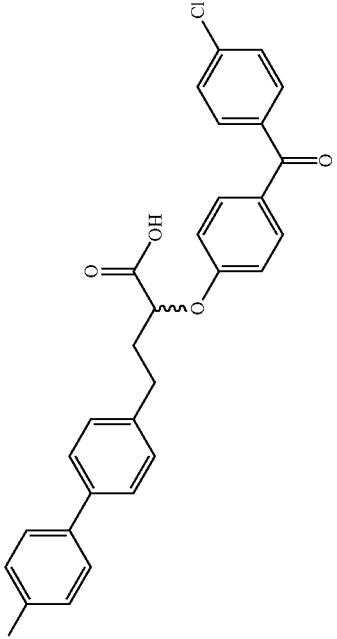 | 505.39 | | ¹H NMR (300 MHz, DMSO-d₆) δ ppm: 2.13-2.33 (2 H, m); 2.76-2.92 (2 H, m); 4.77-4.91 (1 H, m); 6.95-7.12 (2 H, m); 7.24-7.36 (2 H, m); 7.42-7.82 (12 h,); 13.27 (1 H, broad s). | |

-continued

| Ex. | STRUCTURE | MW | M.p. | NMR DATA | MS DATA |
|---|---|---|---|---|---|
| 29 | 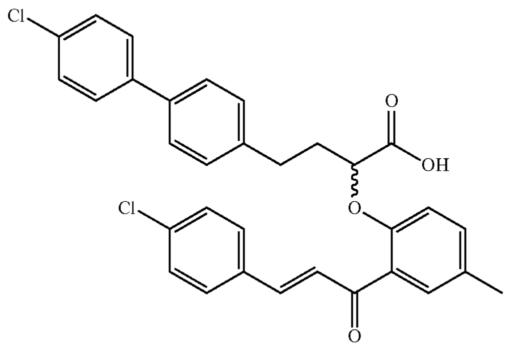 | 545.46 | | ¹H NMR (300 MHz, DMSO-d₆) δ ppm: 1.97-2.23 (2 H, m); 2.27 (3 H, s); 2.57-2.80 (2 H, m); 4.86-5.06 (1 H, m); 6.79-7.09 (2 H, m); 7.20-8.15 (15 H, m). | |
| 30 | 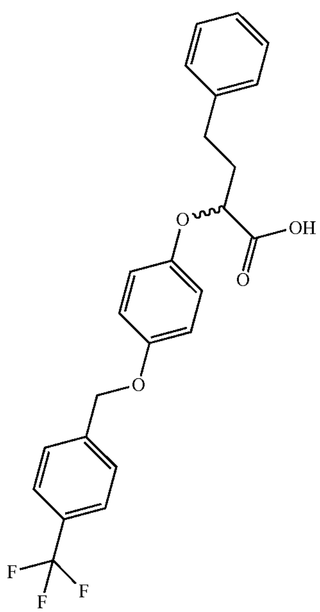 | 430.42 | | | ES− 341.2 |

-continued

| Ex. | STRUCTURE | MW | M.p. | NMR DATA | MS DATA |
|---|---|---|---|---|---|
| 31 | 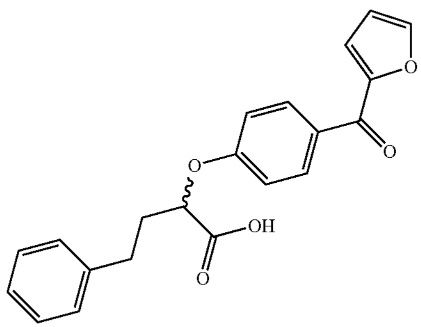 | 350.37 | | | ES− 349.1 |
| 32 | 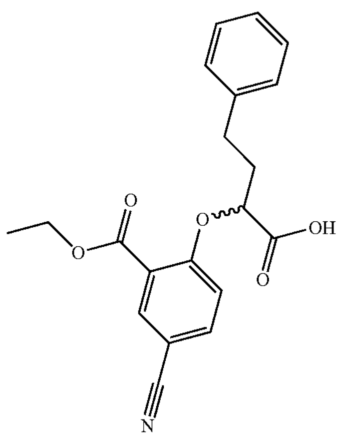 | 353.37 | | | ES+ 354.2<br>ES− 352.1 |

-continued
| Ex. | STRUCTURE | MW | M.p. | NMR DATA | MS DATA |
|---|---|---|---|---|---|
| 33 | 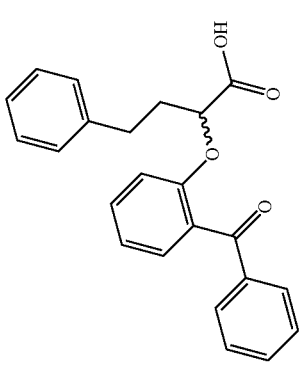 | 360.41 | | | ES− 359.2 |
| 34 | 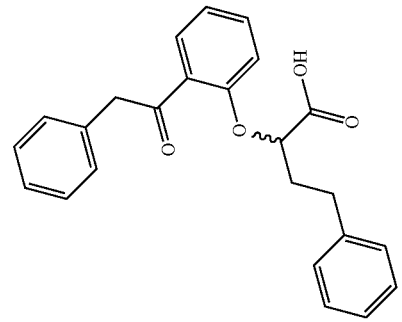 | 374.43 | | | ES− 373.2 |

-continued

| Ex. | STRUCTURE | MW | M.p. | NMR DATA | MS DATA |
|---|---|---|---|---|---|
| 35 | 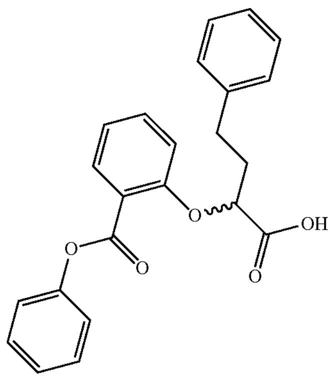 | 376.41 | | | ES− 375.2 |
| 36 | 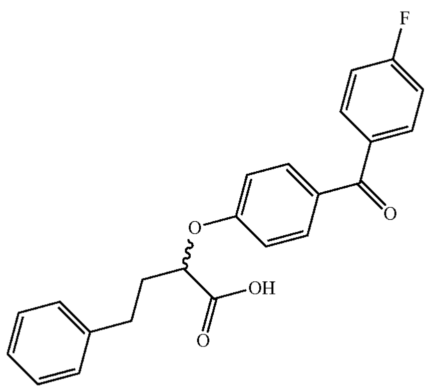 | 378.40 | | | ES− 377.1 |

| Ex. | STRUCTURE | MW | M.p. | NMR DATA | MS DATA |
|---|---|---|---|---|---|
| 37 | 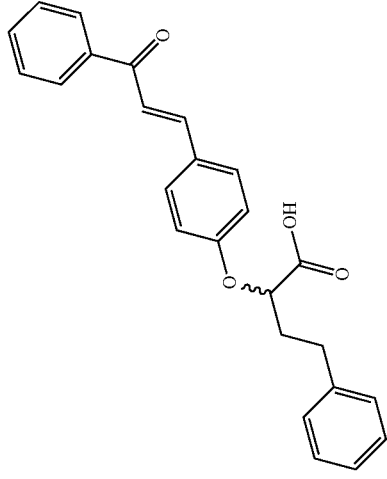 | 386.44 | | | ES– 385.2 |
| 38 | 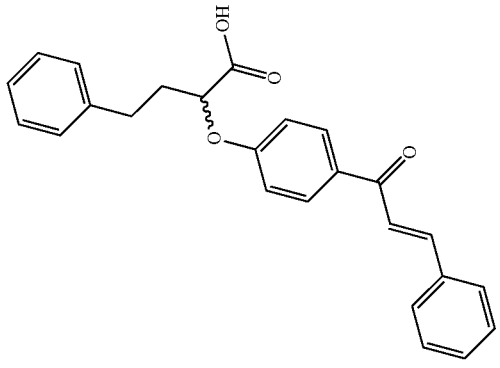 | 386.44 | | | ES– 385.2 |

-continued

| Ex. | STRUCTURE | MW | M.p. | NMR DATA | MS DATA |
|---|---|---|---|---|---|
| 39 | 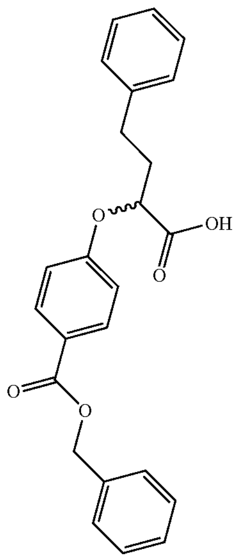 | 390.43 | | | ES− 389.2 |
| 40 | 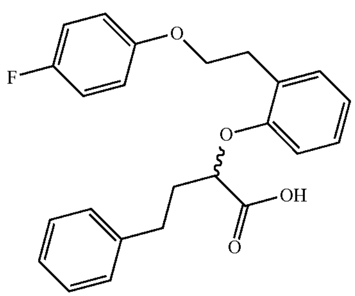 | 394.44 | | | ES− 393.2 |

-continued
| Ex. | STRUCTURE | MW | M.p. | NMR DATA | MS DATA |
|---|---|---|---|---|---|
| 41 | 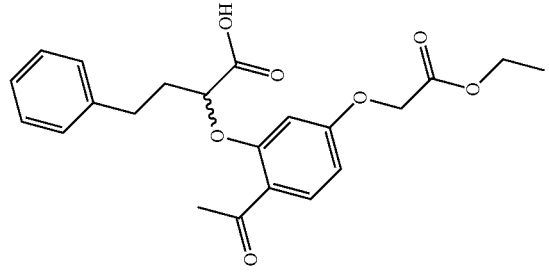 | 400.42 | | | ES− 399.2 |
| 42 | 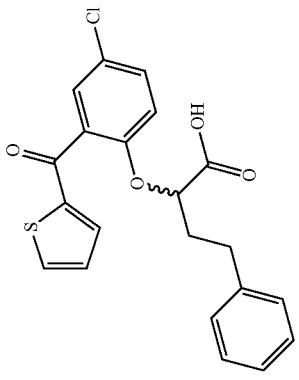 | 400.88 | | | ES− 399.1/401.1<br>1 chlorine atom |

-continued
| Ex. | STRUCTURE | MW | M.p. | NMR DATA | MS DATA |
|---|---|---|---|---|---|
| 43 | 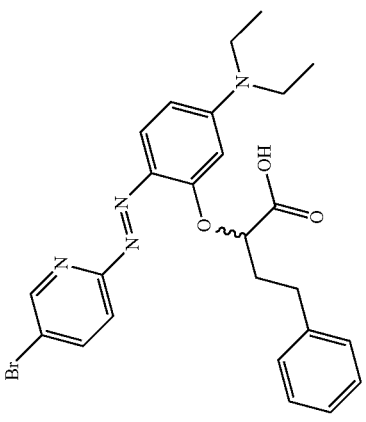 | 511.42 | | | ES+ 511.2/513.2 1 bromine atom |
| 44 | 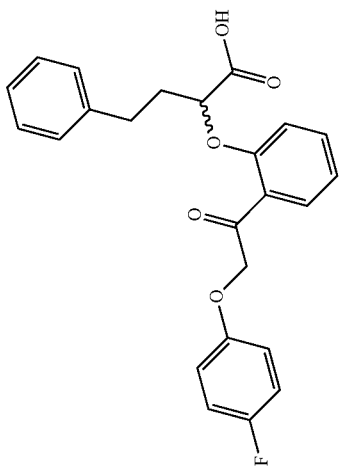 | 408.42 | | | ES- 407.2 |

-continued
| Ex. | STRUCTURE | MW | M.p. | NMR DATA | MS DATA |
|---|---|---|---|---|---|
| 45 | 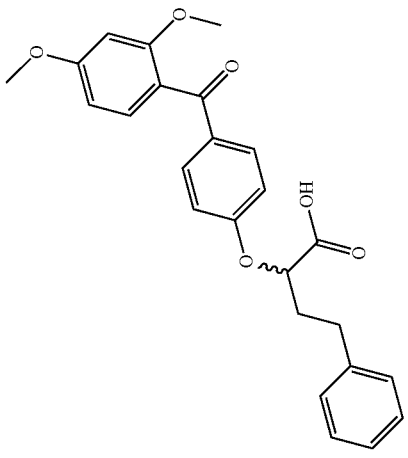 | 420.46 | | | ES– 419.2 |
| 46 | 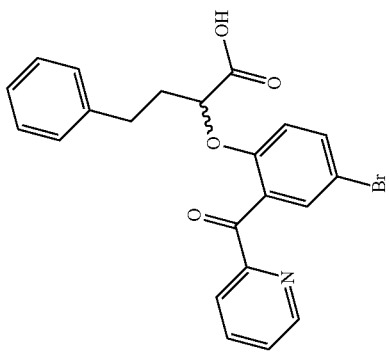 | 440.29 | | | ES– 438.1/440.1<br>1 bromine atom |

-continued
| Ex. | STRUCTURE | MW | M.p. | NMR DATA | MS DATA |
|---|---|---|---|---|---|
| 47 | 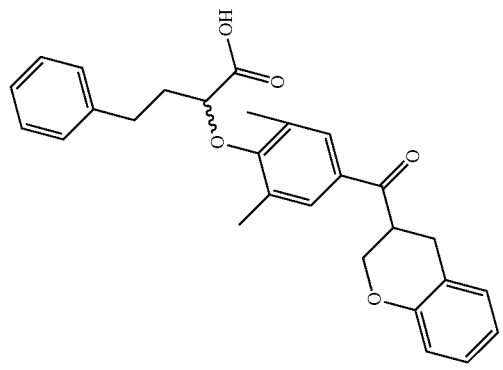 | 444.52 | | | ES- 443.3 |
| 48 | 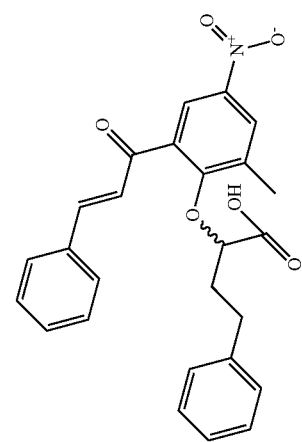 | 445.47 | | | ES- 444.3 |

-continued

| Ex. | STRUCTURE | MW | M.p. | NMR DATA | MS DATA |
|---|---|---|---|---|---|
| 49 | (structure) | 463.32 | | | ES– 461.1/463.1 1 bromine atom |
| 50 | (structure) | 465.34 | | | ES– 463.1/465.1 1 bromine atom |

-continued

| Ex. | STRUCTURE | MW | M.p. | NMR DATA | MS DATA |
|---|---|---|---|---|---|
| 51 | 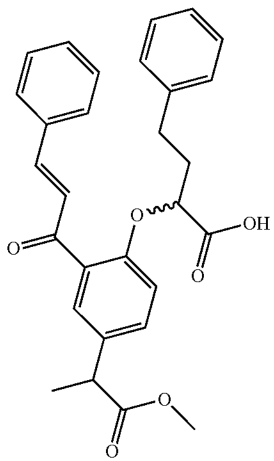 | 472.53 | | | ES- 471.3 |
| 52 | 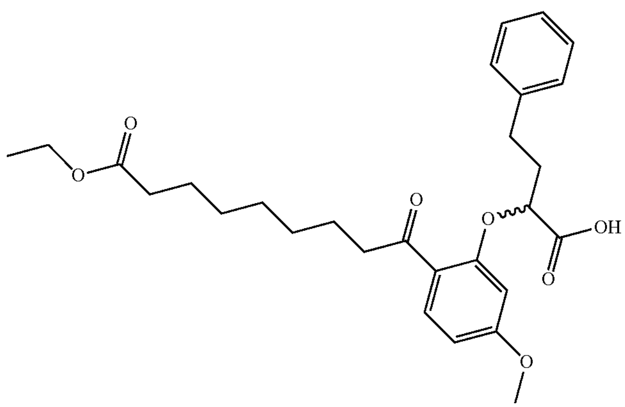 | 484.59 | | | ES- 483.3 |

-continued
| Ex. | STRUCTURE | MW | M.p. | NMR DATA | MS DATA |
|---|---|---|---|---|---|
| 53 | 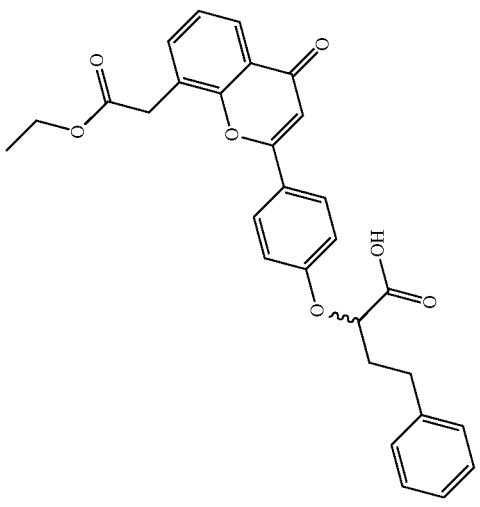 | 486.52 | | | ES+ 487.2 |
| 54 | 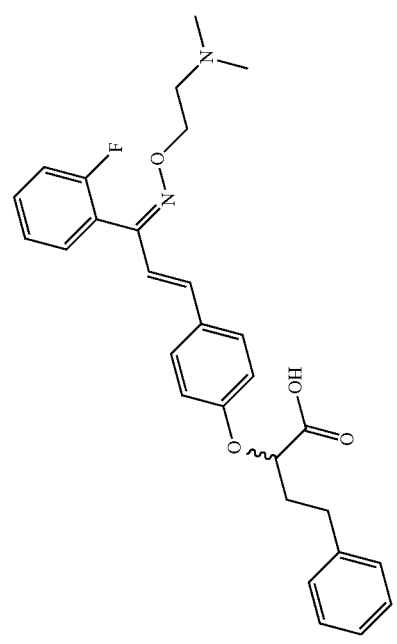 | 490.57 | | | ES+ 491.4 |

-continued

| Ex. | STRUCTURE | MW | M.p. | NMR DATA | MS DATA |
|---|---|---|---|---|---|
| 55 | 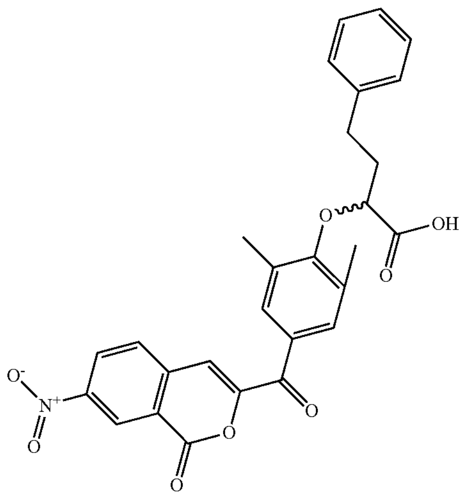 | 501.49 | | | ES− 500.1 |
| 56 | 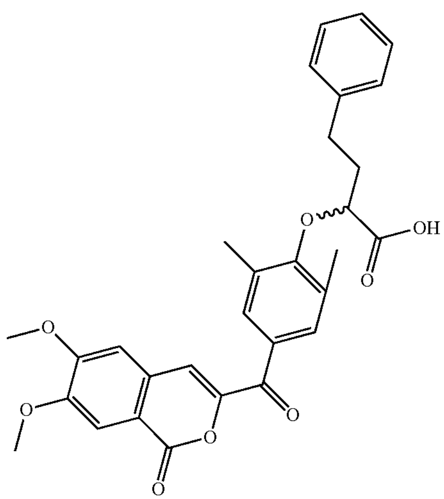 | 516.54 | | | ES+ 517.4 |

| Ex. | STRUCTURE | MW | M.p. | NMR DATA | MS DATA |
|---|---|---|---|---|---|
| 57 | ![structure] | 541.44 | | | ES+ 541.3/543.3 1 bromine atom |
| 58 | ![structure] | 299.30 | | | ES− 298.2 |
| 59 | ![structure] | 323.35 | | | ES+ 324.2 |

-continued
| Ex. | STRUCTURE | MW | M.p. | NMR DATA | MS DATA |
|---|---|---|---|---|---|
| 60 | 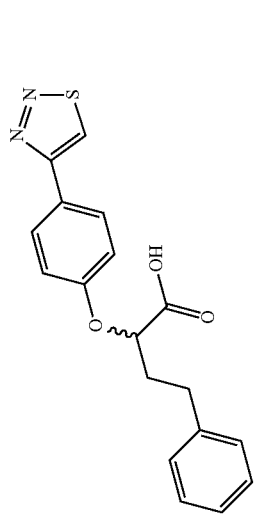 | 340.40 | | | ES– 339.1 |
| 61 | 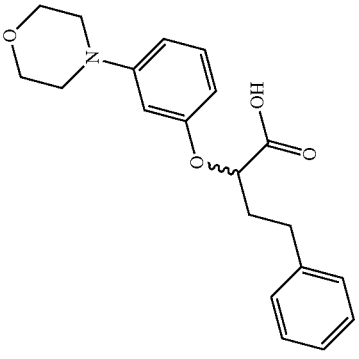 | 341.40 | | | ES– 340.2 |
| 62 | 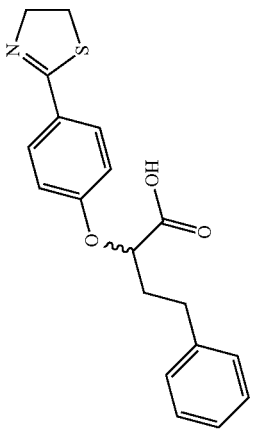 | 341.43 | | | ES– 340.2 |

-continued
| Ex. | STRUCTURE | MW | M.p. | NMR DATA | MS DATA |
|---|---|---|---|---|---|
| 63 | 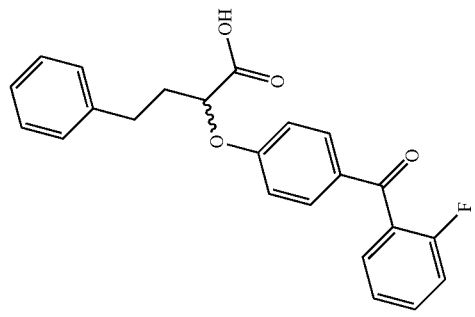 | 378.40 | | | ES− 377.2 |
| 64 | 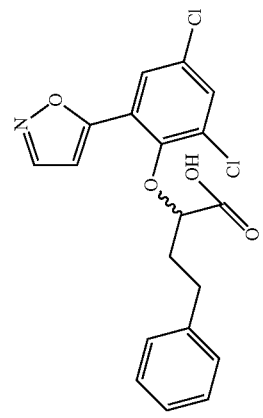 | 392.24 | | | ES− 390.2/392.2 2 chlorine atoms |

-continued
| Ex. | STRUCTURE | MW | M.p. | NMR DATA | MS DATA |
|---|---|---|---|---|---|
| 65 | 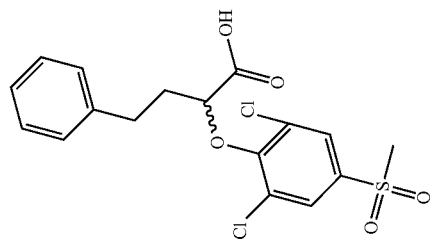 | 403.28 | | | ES- 401.1/403.1<br>2 chlorine atoms |
| 66 | 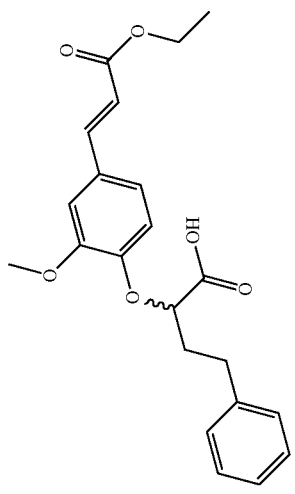 | 384.43 | | | ES- 383.3 |

-continued
| Ex. | STRUCTURE | MW | M.p. | NMR DATA | MS DATA |
|---|---|---|---|---|---|
| 67 | 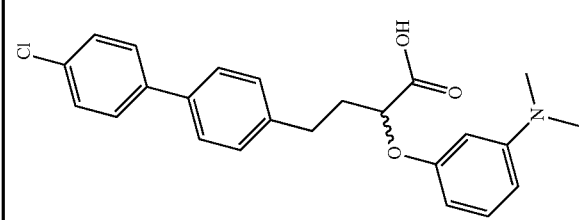 | 409.91 | | | ES– 408.2/410.2<br>1 chlorine atom |
| 68 | 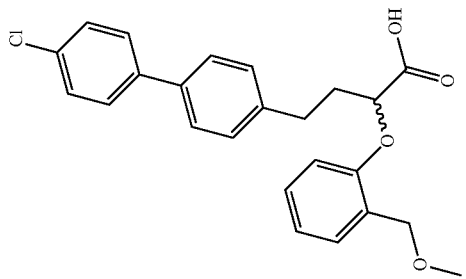 | 410.89 | | | ES– 409.1/411.1<br>1 chlorine atom |

| Ex. | STRUCTURE | MW | M.p. | NMR DATA | MS DATA |
|---|---|---|---|---|---|
| 69 | 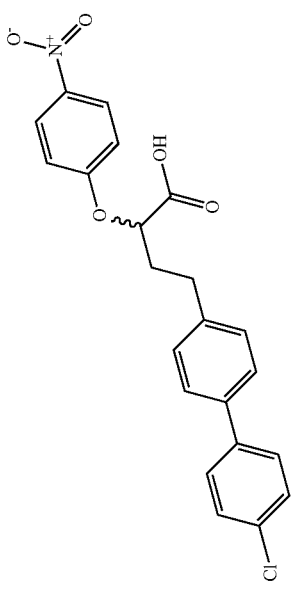 | 411.84 | | | ES– 410.2/412.2 1 chlorine atom |
| 70 | 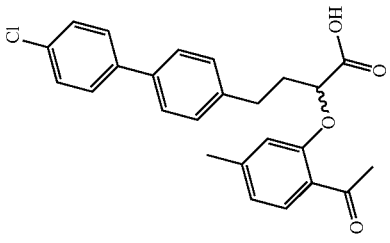 | 422.91 | | | ES– 421.2/423.2 1 chlorine atom |

-continued

| Ex. | STRUCTURE | MW | M.p. | NMR DATA | MS DATA |
|---|---|---|---|---|---|
| 71 | 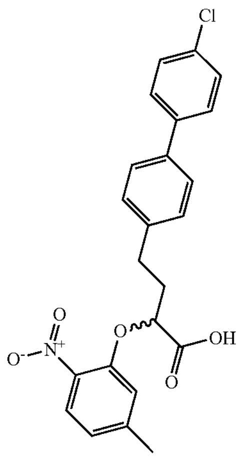 | 425.87 | | | ES- 424.2/426.2 1 chlorine atom |
| 72 | 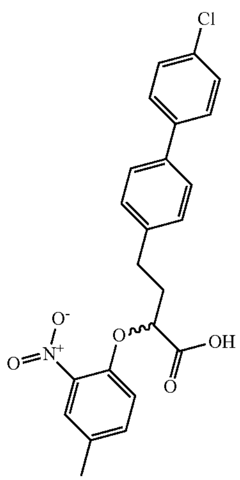 | 425.87 | | | ES- 424.2/426.2 1 chlorine atom |

| Ex. | STRUCTURE | MW | M.p. | NMR DATA | MS DATA |
|---|---|---|---|---|---|
| 73 | 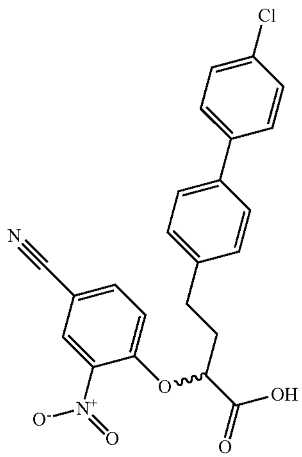 | 436.85 | | | ES− 435.2/437.2<br>1 chlorine atom |
| 74 | 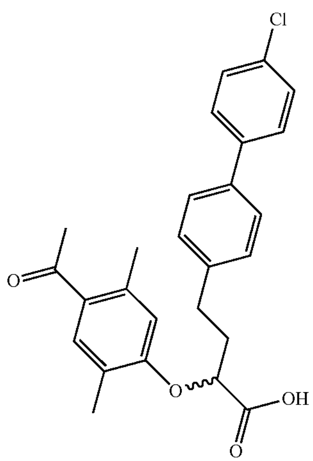 | 436.93 | | | ES− 435.2/437.2<br>1 chlorine atom |

| Ex. | STRUCTURE | MW | M.p. | NMR DATA | MS DATA |
|---|---|---|---|---|---|
| 75 | 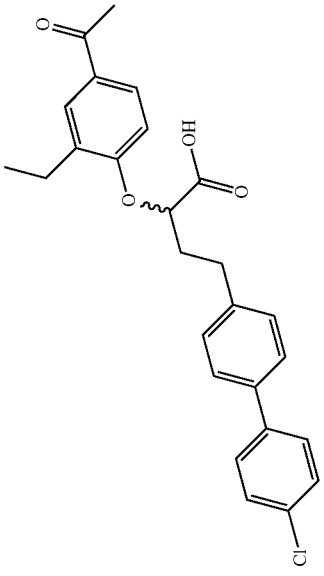 | 436.93 | | | ES− 435.2/437.2 1 chlorine atom |
| 76 | 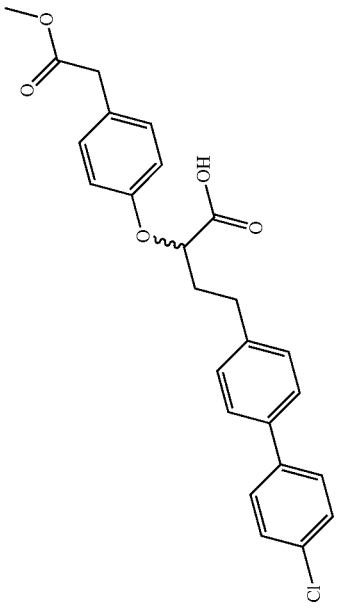 | 438.90 | | | ES− 437.2/439.2 1 chlorine atom |
| 77 | 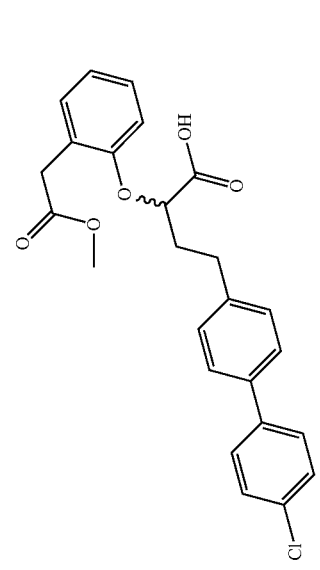 | 438.90 | | | ES− 437.2/439.2 1 chlorine atom |

-continued
| Ex. | STRUCTURE | MW | M.p. | NMR DATA | MS DATA |
|---|---|---|---|---|---|
| 78 | 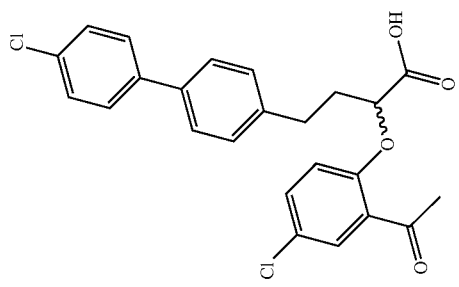 | 443.32 | | | ES− 441.2/443.2/ 445.2<br>2 chlorine atoms |
| 79 | 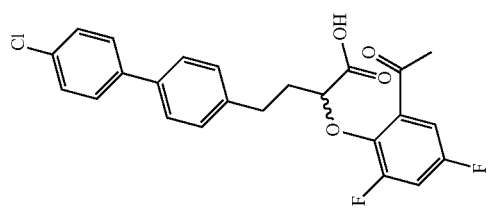 | 444.86 | | | ES− 443.2/445.2<br>1 chlorine atom |

| Ex. | STRUCTURE | MW | M.p. | NMR DATA | MS DATA |
|---|---|---|---|---|---|
| 80 | (4'-chlorobiphenyl-CH₂CH₂-CH(COOH)-O-phenyl-CH=CH-COOCH₃) | 450.92 | | | ES− 449.2/451.2<br>1 chlorine atom |
| 81 | (4'-chlorobiphenyl-CH₂CH₂-CH(COOH)-O-phenyl-CH₂CH₂-COOCH₃) | 452.93 | | | ES− 451.3/453.3<br>1 chlorine atom |

-continued
| Ex. | STRUCTURE | MW | M.p. | NMR DATA | MS DATA |
|---|---|---|---|---|---|
| 82 | 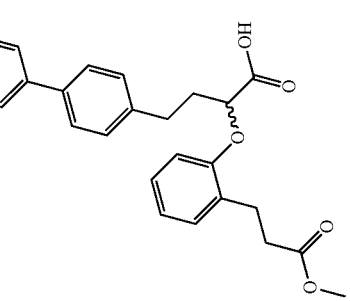 | 452.93 | | | ES− 451.3/453.3 1 chlorine atom |
| 83 | 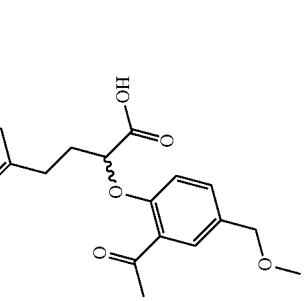 | 452.93 | | | ES− 451.3/453.3 1 chlorine atom |

-continued

| Ex. | STRUCTURE | MW | M.p. | NMR DATA | MS DATA |
|---|---|---|---|---|---|
| 84 | 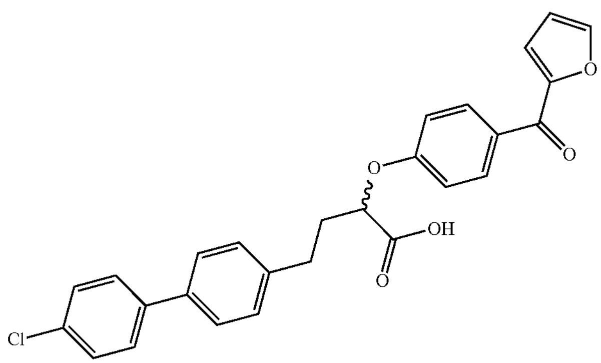 | 460.91 | | | ES- 459.2/461.2 1 chlorine atom |
| 85 | 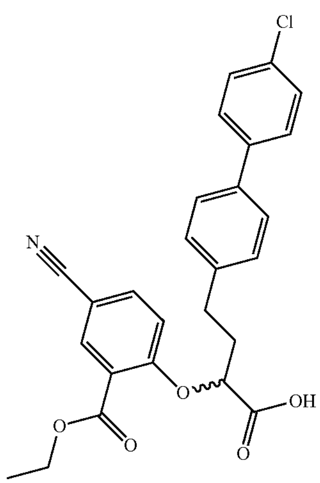 | 463.91 | | | ES- 462.2/464.2 1 chlorine atom |

-continued

| Ex. | STRUCTURE | MW | M.p. | NMR DATA | MS DATA |
|---|---|---|---|---|---|
| 86 | 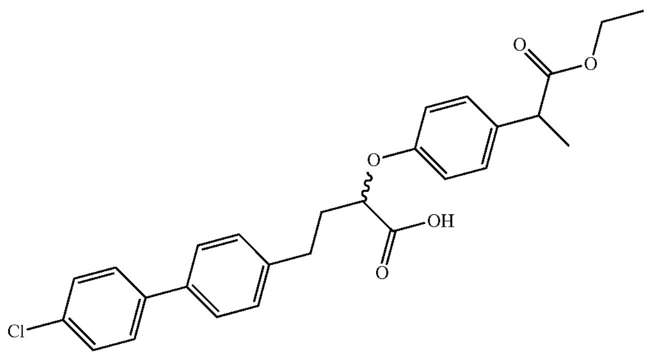 | 466.96 | | | ES− 465.2/467.2 1 chlorine atom |
| 87 | 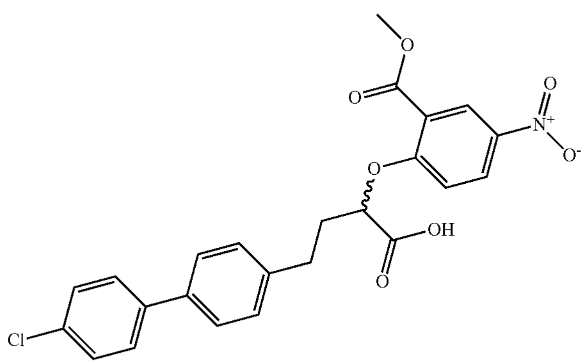 | 469.88 | | | ES− 468.2/470.2 2 chlorine atoms |

-continued
| Ex. | STRUCTURE | MW | M.p. | NMR DATA | MS DATA |
|---|---|---|---|---|---|
| 88 | 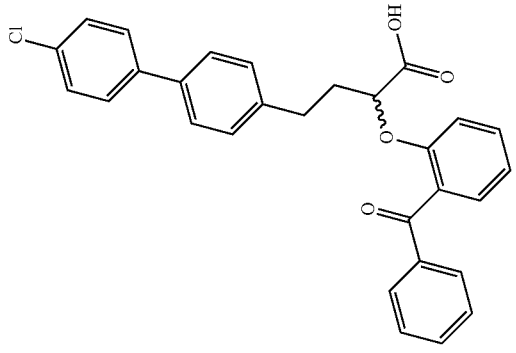 | 470.95 | | | ES− 469.2/471.2 1 chlorine atom |
| 89 | 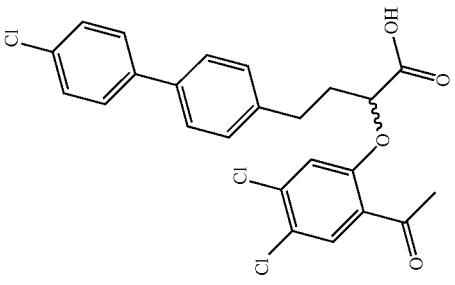 | 477.77 | | | ES− 475.2/477.2/ 479.2 3 chlorine atoms |

-continued
| Ex. | STRUCTURE | MW | M.p. | NMR DATA | MS DATA |
|---|---|---|---|---|---|
| 90 | 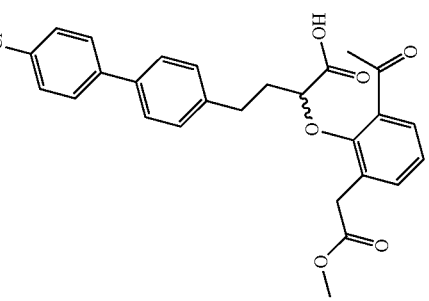 | 480.94 | | | ES– 479.2/481.2<br>1 chlorine atom |
| 91 | 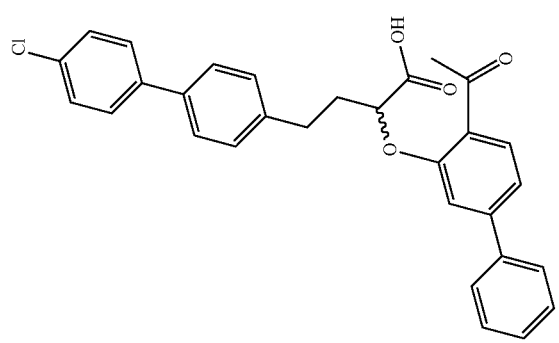 | 484.98 | | | ES– 483.2/485.2<br>1 chlorine atom |

| Ex. | STRUCTURE | MW | M.p. | NMR DATA | MS DATA |
|---|---|---|---|---|---|
| 92 | 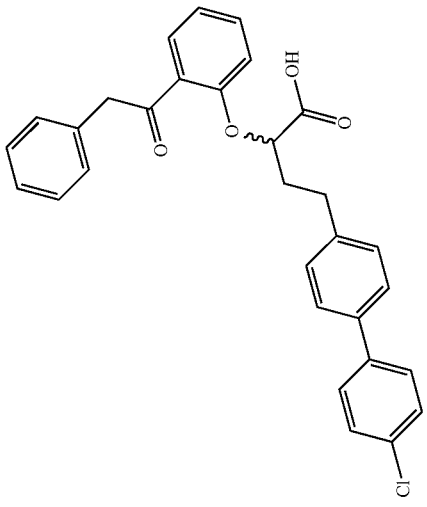 | 484.98 | | | ES− 483.2/485.2<br>1 chlorine atom |
| 93 | 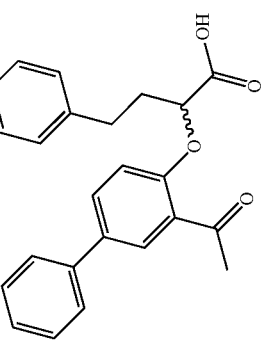 | 484.98 | | | ES− 483.2/485.2<br>1 chlorine atom |

| Ex. | STRUCTURE | MW | M.p. | NMR DATA | MS DATA |
|---|---|---|---|---|---|
| 94 | 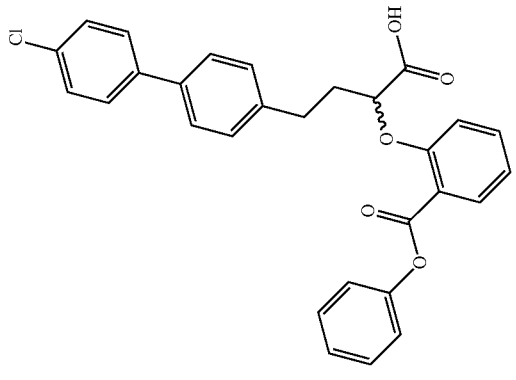 | 486.95 | | | ES− 485.2/487.2<br>1 chlorine atom |
| 95 | 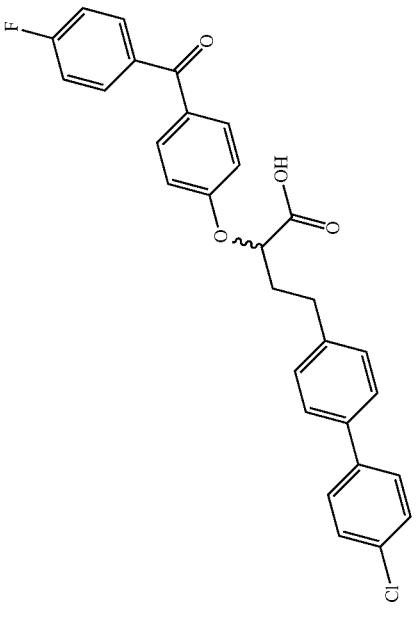 | 488.94 | | | ES− 487.3/489.3<br>2 chlorine atoms |

-continued
| Ex. | STRUCTURE | MW | M.p. | NMR DATA | MS DATA |
|---|---|---|---|---|---|
| 96 | 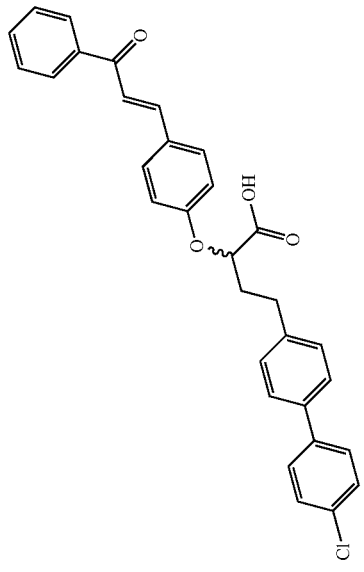 | 496.99 | | | ES- 495.2/497.2<br>1 chlorine atom |
| 97 | 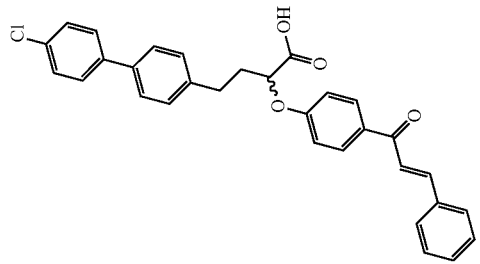 | 496.99 | | | ES- 495.2/497.2<br>1 chlorine atom |

-continued
| Ex. | STRUCTURE | MW | M.p. | NMR DATA | MS DATA |
|---|---|---|---|---|---|
| 98 | 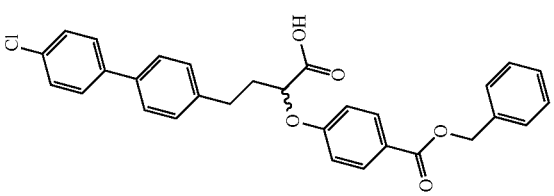 | 500.98 | | | ES− 499.3/501.3 1 chlorine atom |
| 99 | 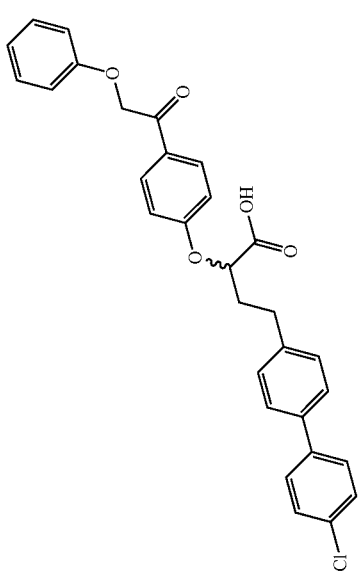 | 500.98 | | | ES− 499.3 |

-continued
| Ex. | STRUCTURE | MW | M.p. | NMR DATA | MS DATA |
|---|---|---|---|---|---|
| 100 | 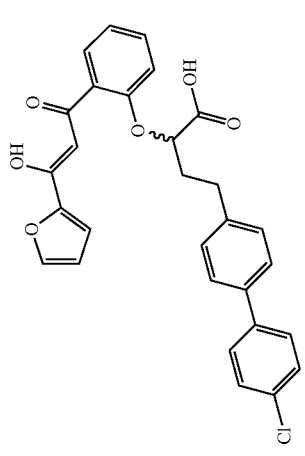 | 502.95 | | | ES+ 503.3/505.3 1 chlorine atom |
| 101 | 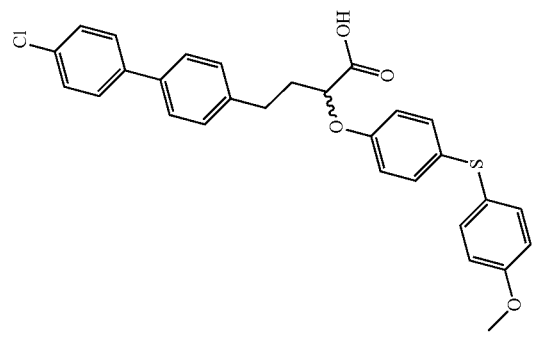 | 505.03 | | | ES− 503.3/505.3 1 chlorine atom |

-continued

| Ex. | STRUCTURE | MW | M.p. | NMR DATA | MS DATA |
|---|---|---|---|---|---|
| 102 | 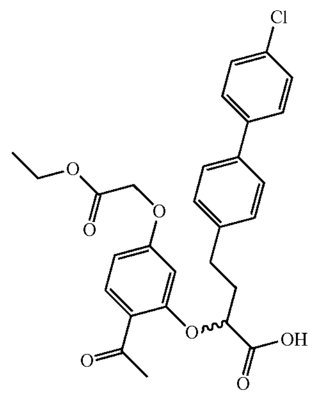 | 510.97 | | | ES- 509.3/511.3<br>1 chlorine atom |
| 103 | 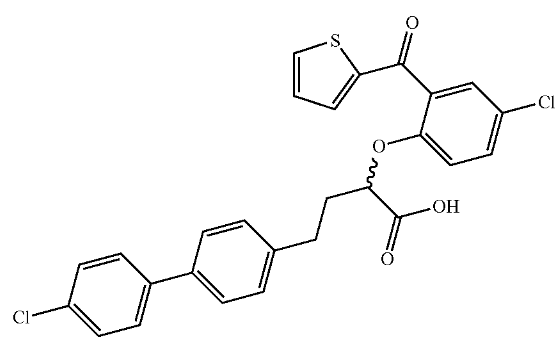 | 511.42 | | | ES- 509.2/511.2/<br>513.2<br>2 chlorine atoms |

| Ex. | STRUCTURE | MW | M.p. | NMR DATA | MS DATA |
|---|---|---|---|---|---|
| 104 | 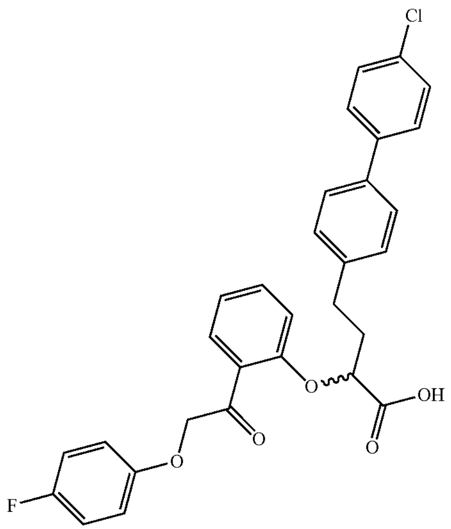 | 518.97 | | | ES− 517.3/519.3 1 chlorine atom |
| 105 | 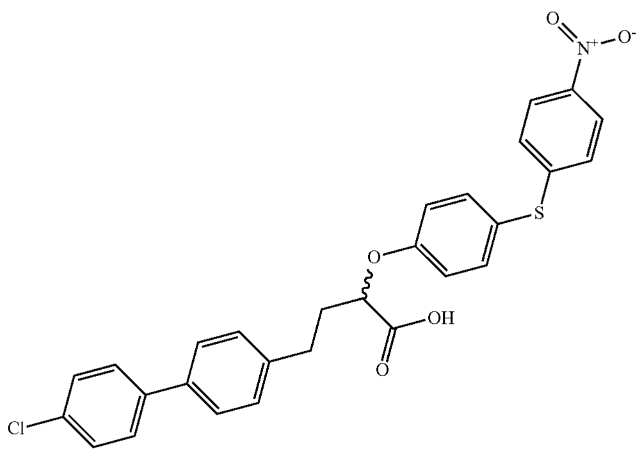 | 520.00 | | | ES− 518.2/520.2 1 chlorine atom |

| Ex. | STRUCTURE | MW | M.p. | NMR DATA | MS DATA |
|---|---|---|---|---|---|
| 106 | 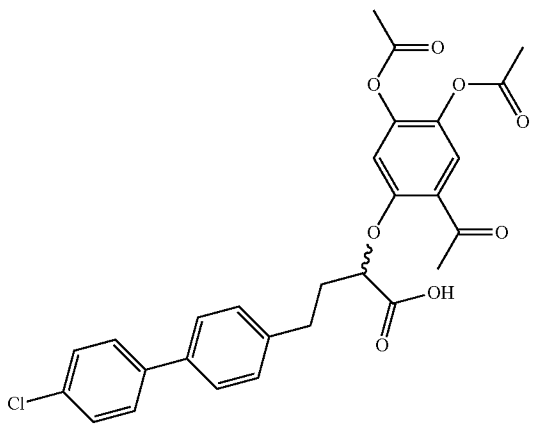 | 524.95 | | | ES- 523.3/525.3<br>1 chlorine atom |
| 107 | 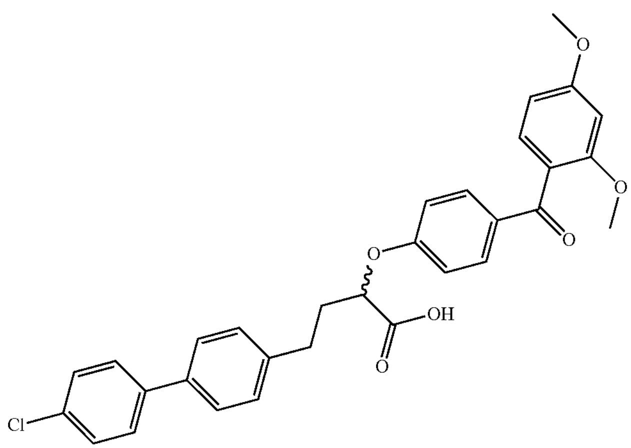 | 531.00 | | | ES- 529.1/531.1<br>1 chlorine atom |

-continued

| Ex. | STRUCTURE | MW | M.p. | NMR DATA | MS DATA |
|---|---|---|---|---|---|
| 108 | (structure) | 550.83 | | | ES− 550.2/552.2/554.2<br>1 chlorine atom and 1 bromine atom |
| 109 | (structure) | 573.86 | | | ES− 571.2/573.2/575.2<br>1 chlorine atom + 1 bromine atom |

-continued
| Ex. | STRUCTURE | MW | M.p. | NMR DATA | MS DATA |
|---|---|---|---|---|---|
| 110 | 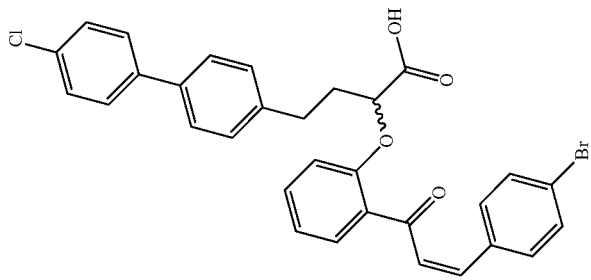 | 575.88 | | | ES− 573.2/575.2/577.2<br>1 chlorine atom and 1 bromine atom |
| 111 | 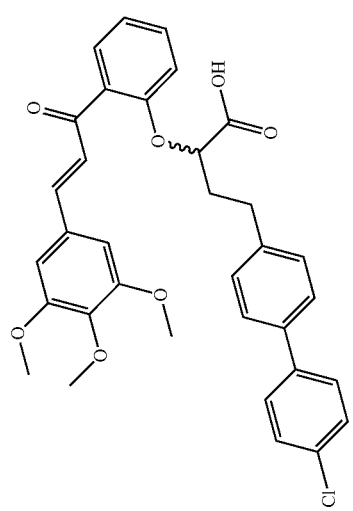 | 587.06 | | | ES− 585.3/587.3<br>1 chlorine atom |

| Ex. | STRUCTURE | MW | M.p. | NMR DATA | MS DATA |
|---|---|---|---|---|---|
| 112 | 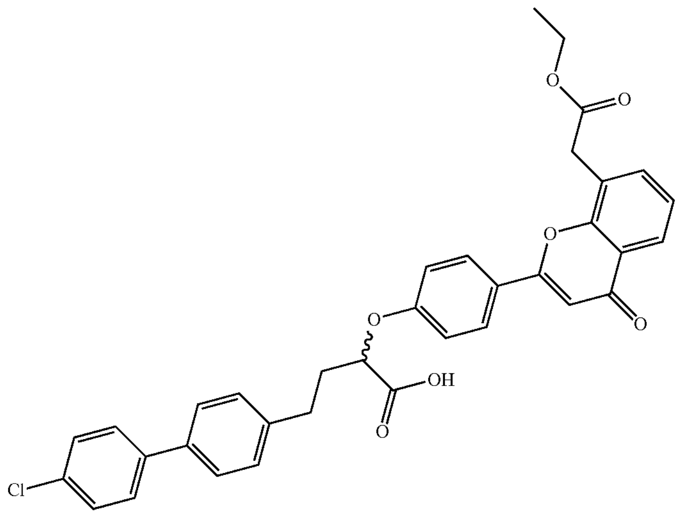 | 597.06 | | | ES- 595.3/597.3 1 chlorine atom |
| 113 | 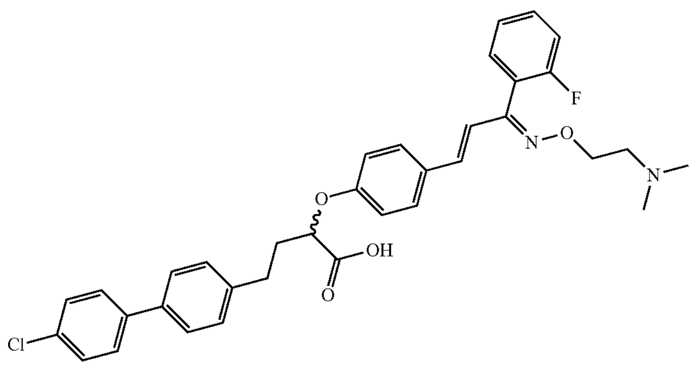 | 601.11 | | | ES- 599.4/601.4 1 chlorine atom |

-continued

| Ex. | STRUCTURE | MW | M.p. | NMR DATA | MS DATA |
|---|---|---|---|---|---|
| 114 | 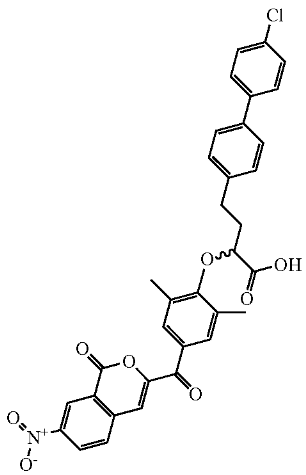 | 612.03 | | | ES– 610.3/612.3<br>1 chlorine atom |
| 115 | 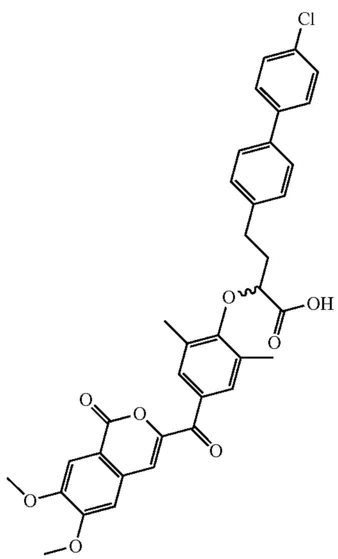 | 627.09 | | | ES– 625.1/627.1<br>1 chlorine atom |

-continued
| Ex. | STRUCTURE | MW | M.p. | NMR DATA | MS DATA |
|---|---|---|---|---|---|
| 116 | 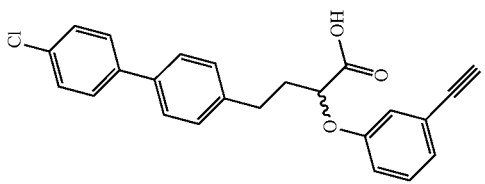 | 390.86 | | | ES− 389.1/391.1<br>1 chlorine atom |
| 117 | 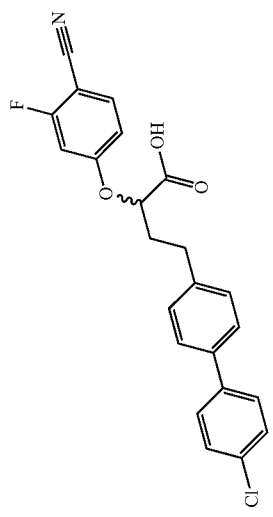 | 409.84 | | | ES− 408.2/410.2<br>1 chlorine atom |

-continued

| Ex. | STRUCTURE | MW | M.p. | NMR DATA | MS DATA |
|---|---|---|---|---|---|
| 118 | (structure: 4'-chlorobiphenyl-CH2CH2-CH(COOH)-O-(3,5-dimethyl-4-cyanophenyl)) | 419.91 | | | ES– 418.2/420.2 1 chlorine atom |
| 119 | (structure: 4'-chlorobiphenyl-CH2CH2-CH(COOH)-O-(2,4,6-trifluorophenyl)) | 420.81 | | | ES– 419.2/421.2 1 chlorine atom |

-continued
| Ex. | STRUCTURE | MW | M.p. | NMR DATA | MS DATA |
|---|---|---|---|---|---|
| 120 | 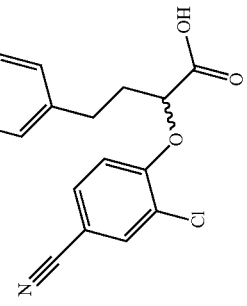 | 426.30 | | | ES− 424.2/426.2/ 426.2 2 chlorine atoms |
| 121 | 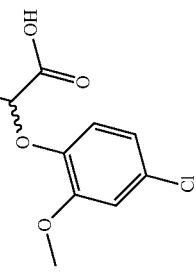 | 431.31 | | | ES− 429.2/431.2 2 chlorine atoms |

-continued
| Ex. | STRUCTURE | MW | M.p. | NMR DATA | MS DATA |
|---|---|---|---|---|---|
| 122 | 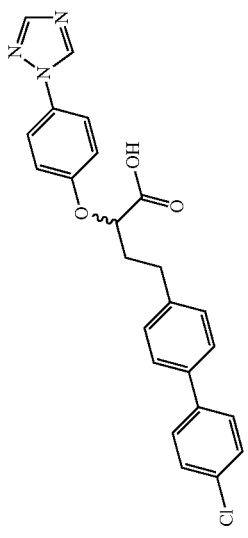 | 433.89 | | | ES- 432.2/434.2<br>1 chlorine atom |
| 123 | 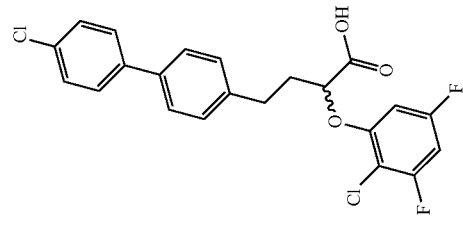 | 437.27 | | | ES- 435.1/437.1/<br>439.1<br>2 chlorine atoms |

-continued
| Ex. | STRUCTURE | MW | M.p. | NMR DATA | MS DATA |
|---|---|---|---|---|---|
| 124 | 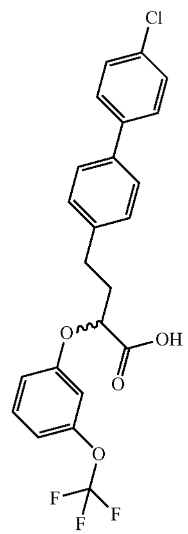 | 450.84 | | | ES- 449.2/451.2<br>1 chlorine atom |
| 125 | 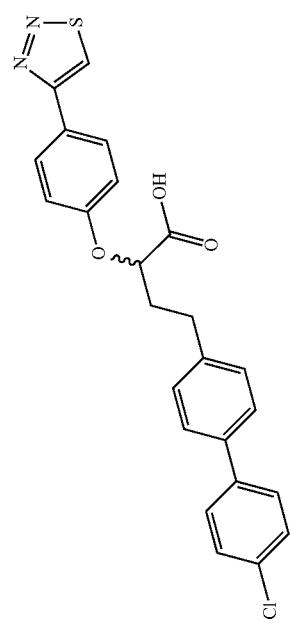 | 450.94 | | | ES- 449.2/451.2<br>1 chlorine atom |

-continued
| Ex. | STRUCTURE | MW | M.p. | NMR DATA | MS DATA |
|---|---|---|---|---|---|
| 126 | 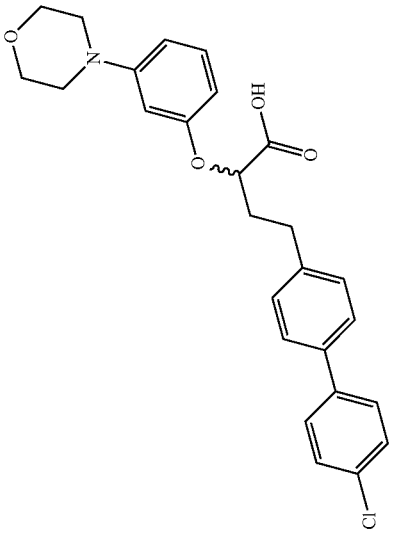 | 451.95 | | | ES− 450.3/452.3<br>1 chlorine atom |
| 127 | 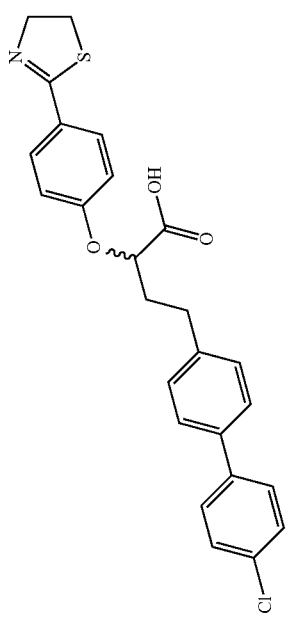 | 451.97 | | | ES− 450.3/452.3<br>1 chlorine atom |

| Ex. | STRUCTURE | MW | M.p. | NMR DATA | MS DATA |
|---|---|---|---|---|---|
| 128 | 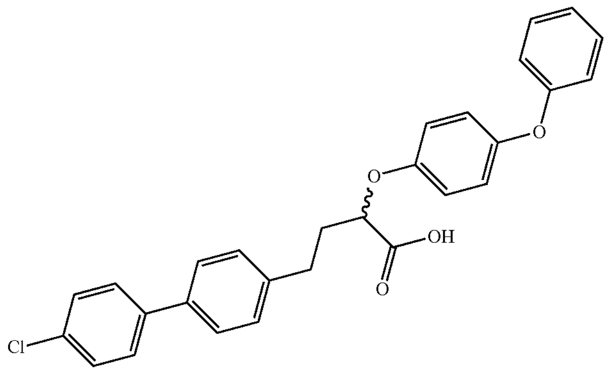 | 458.94 | | | ES− 457.2/459.2 1 chlorine atom |
| 129 | 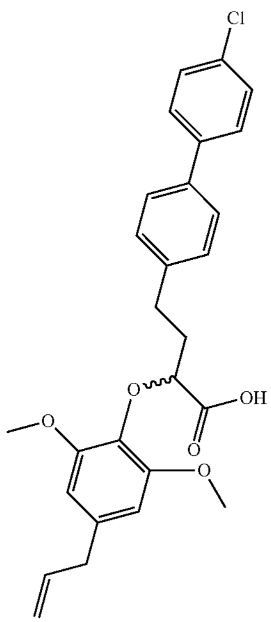 | 465.95 | | | ES− 465.3/467.3 1 chlorine atom |

| Ex. | STRUCTURE | MW | M.p. | NMR DATA | MS DATA |
|---|---|---|---|---|---|
| 130 | 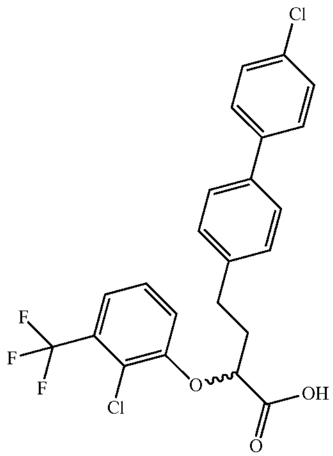 | 469.28 | | | ES− 467.2/469.2/ 471.2 2 chlorine atoms |
| 131 | 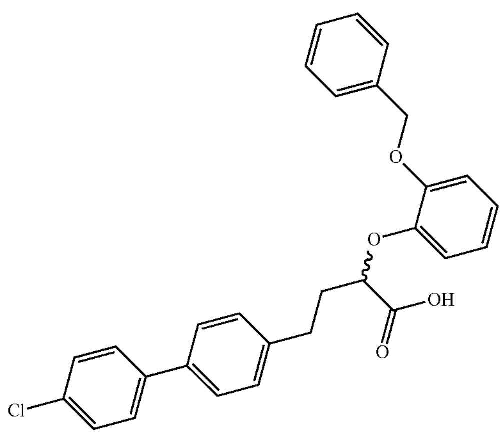 | 472.97 | | | ES− 471.3/473.3 1 chlorine atom |

-continued
| Ex. | STRUCTURE | MW | M.p. | NMR DATA | MS DATA |
|---|---|---|---|---|---|
| 132 | 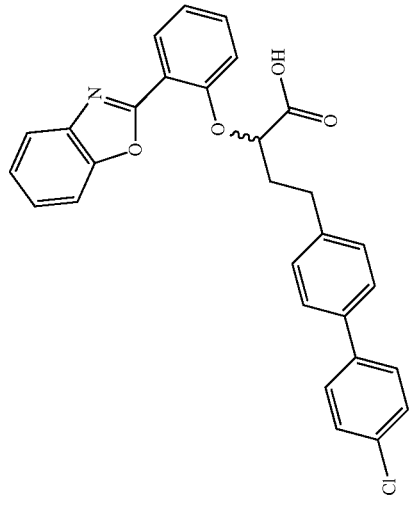 | 483.95 | | | ES- 482.2/484.2<br>1 chlorine atom |
| 133 | 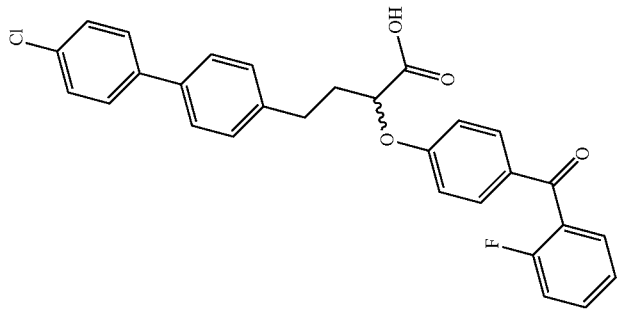 | 488.94 | | | ES- 487.2/489.2 |

-continued
| Ex. | STRUCTURE | MW | M.p. | NMR DATA | MS DATA |
|---|---|---|---|---|---|
| 134 | 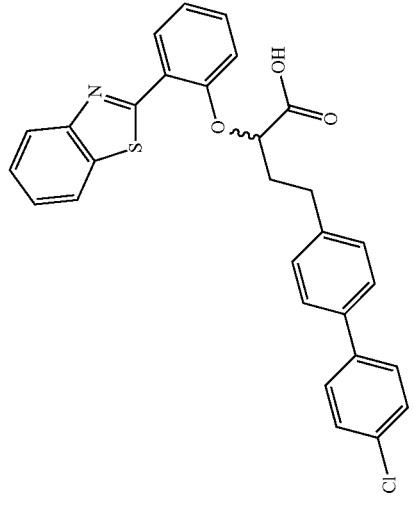 | 500.02 | | | ES– 498.2/500.2 |
| 135 | 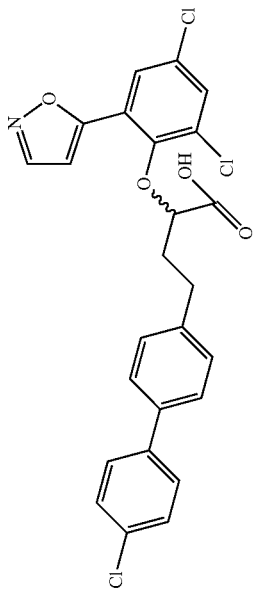 | 502.78 | | | ES– 500.1/502.1/504.2<br>3 chlorine atoms |

-continued

| Ex. | STRUCTURE | MW | M.p. | NMR DATA | MS DATA |
|---|---|---|---|---|---|
| 136 | (structure) | 513.82 | | | ES– 511.1/513.1/515.1<br>3 chlorine atoms |
| 137 | (structure) | 537.01 | | | ES– 535.3/537.3<br>1 chlorine atom |

-continued
| Ex. | STRUCTURE | MW | M.p. | NMR DATA | MS DATA |
|---|---|---|---|---|---|
| 138 | 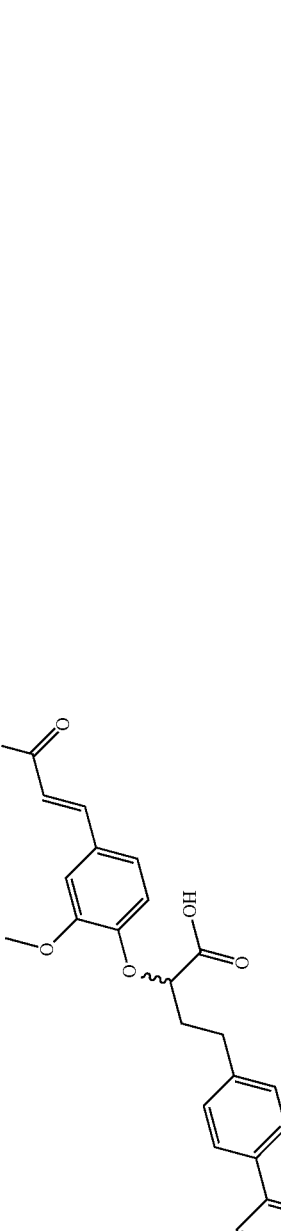 | 494.97 | | | ES- 493.3/495.3 1 chlorine atom |
| 139 | 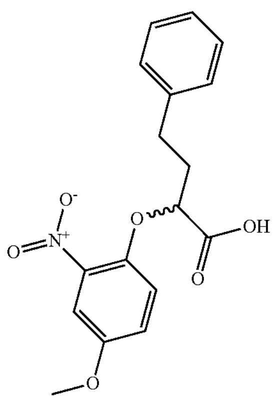 | 331.32 | | | ES- 330.1 |
| 140 | 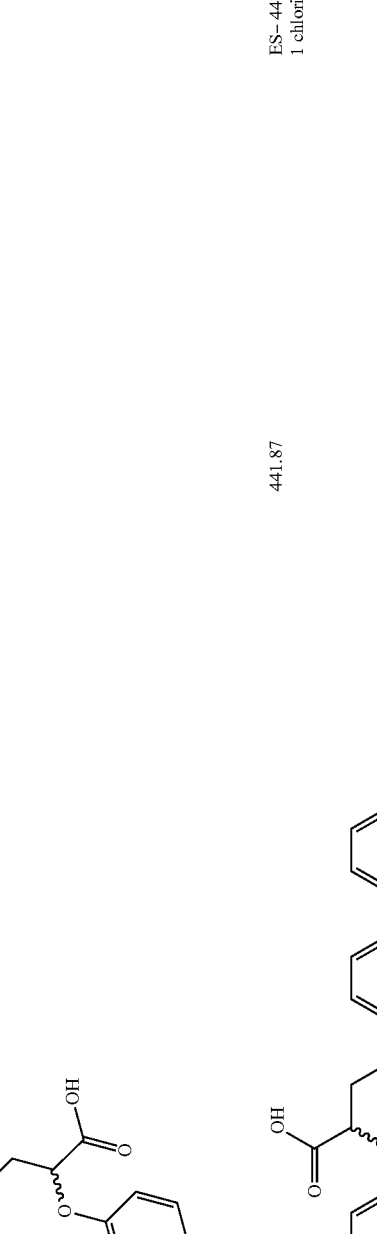 | 441.87 | | | ES- 440.2/442.2 1 chlorine atom |

| Ex. | STRUCTURE | MW | M.p. | NMR DATA | MS DATA |
|---|---|---|---|---|---|
| 141 | 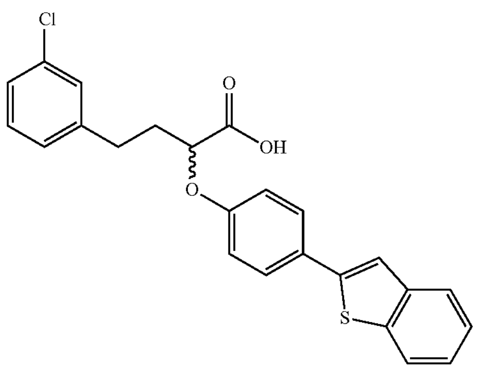 | 422.93 | 109-110° C. | ¹H NMR (300 MHz, CDCl₃) δ ppm:): 2.12-2.48 (2 H, m); 2.66-3.04 (2 H, m); 4.40-4.69 (1 H, m); 5.53 (1 H, broad s); 6.62-6.84 (4 H, m); 6.93-7.48 (9 H, m). | |
| 142 | 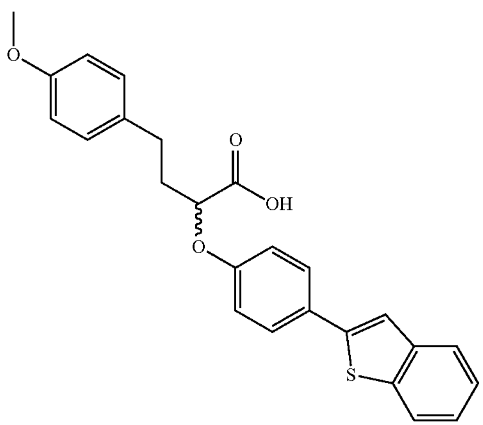 | 418.51 | 198-199° C. | ¹H NMR (300 MHz, DMSO-d₆) δ ppm:): 1.99-2.18 (2 H, m); 2.59-2.84 (2 H, m); 3.70 (3 H, s); 4.44-4.65 (1 H, m); 6.74-7.47 (8 H, m); 7.55-8.06 (5 H, m). | |
| 143 | 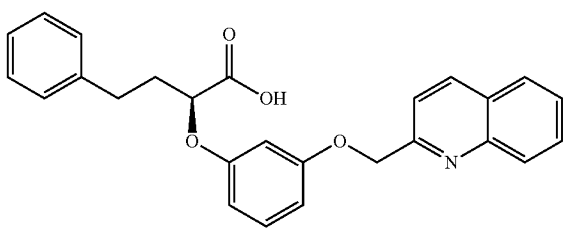 | 413.47 | 124° C. | ¹H NMR (300 MHz, CDCl₃) δ ppm:): 2.16-2.47 (2 H, m); 2.64-3.07 (2 H, m); 4.56-4.76 (1 H, m); 5.21 (2 H, s); 6.27-6.73 (3 H, m); 6.92-7.34 (6 H, m); 7.44-7.91 (4 H, m); 7.99-8.28 (2 H, m); 9.01 (1 H, broad s). | |

| Ex. | STRUCTURE | MW | M.p. | NMR DATA | MS DATA |
|---|---|---|---|---|---|
| 144 | 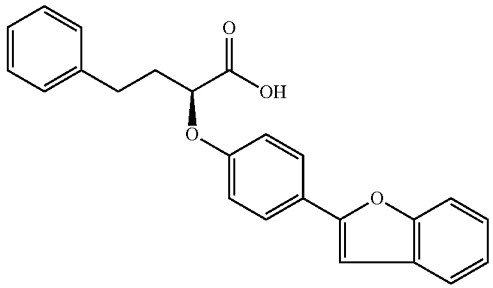 | 372.42 | 198° C. | ¹H NMR (300 MHz, CDCl₃) δ ppm:): 2.27-2.56 (2 H, m); 2.79-3.14 (2 H, m); 4.63-4.88 (1 H, m); 6.87-7.12 (3 H, m); 7.16-7.45 (7 H, m); 7.47-7.97 (4 H, m). | |
| 145 | 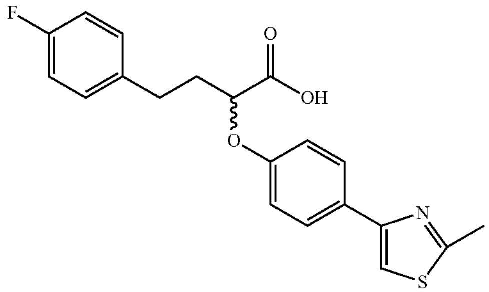 | 371.43 | >260° C. | ¹H NMR (300 MHz, DMSO-d₆) δ ppm:): 1.90-2.23 (2 H, m); 2.59-2.89 (2 H, m); 2.68 (3 H, s); 4.21-4.39 (1 H, m); 6.72-7.30 (6 H, m); 7.62-7.84 (3 H, m). | |
| 146 | 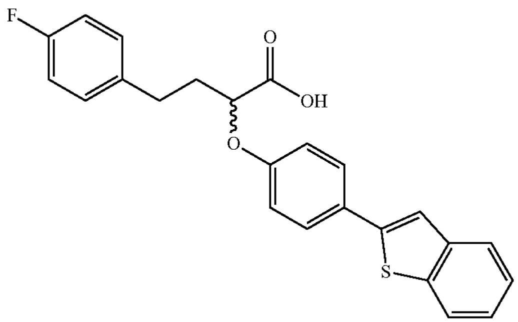 | 406.48 | 188-190° C. | ¹H NMR (300 MHz, CDCl₃) δ ppm:): 2.03-2.38 (2 H, m); 2.61-2.93 (2 H, m); 4.46-4.68 (1 H, m); 6.66-7.44 (9 H, m); 7.44-7.87 (4 H, m). | |

| Ex. | STRUCTURE | MW | M.p. | NMR DATA | MS DATA |
|---|---|---|---|---|---|
| 147 | 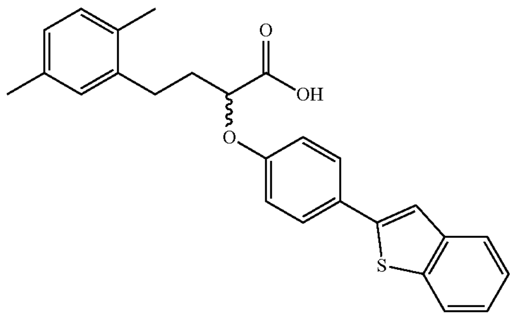 | 416.54 | | 1H NMR (300 MHz, CDCl3) δ ppm:): 1.71-2.10 (2 H, m); 2.17 (3 H, s); 2.19 (3 H, s); 2.50-2.71 (2 H, m); 4.09-4.32 (1 H, m); 6.53-7.10 (6 H, m); 7.10-7.70 (6 H, m). | |
| 148 | 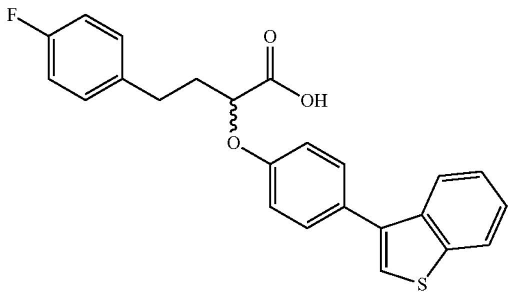 | 406.48 | | 1H NMR (300 MHz, CDCl3) δ ppm:): 2.16-2.51 (2 H, m); 2.70-3.07 (2 H, m); 4.54-4.80 (1 H, m); 6.82-7.58 (11 H, m); 7.76-8.03 (2 H, m). | |
| 149 | 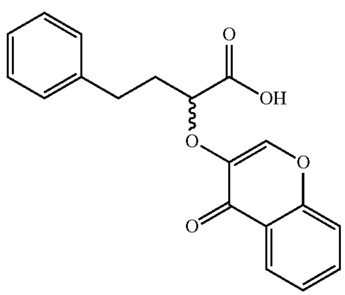 | 324.33 | | 1H NMR (300 MHz, CDCl3) δ ppm:): 2.15-2.53 (2 H, m); 2.75-3.04 (2 H, m); 4.43-4.57 (1 H, m); 7.07-7.60 (7 H, m); 7.66-7.84 (1 H, m); 8.00 (1 H, s); 8.17-8.37 (1 H, m). | |

-continued

| Ex. | STRUCTURE | MW | M.p. | NMR DATA | MS DATA |
|---|---|---|---|---|---|
| 150 | 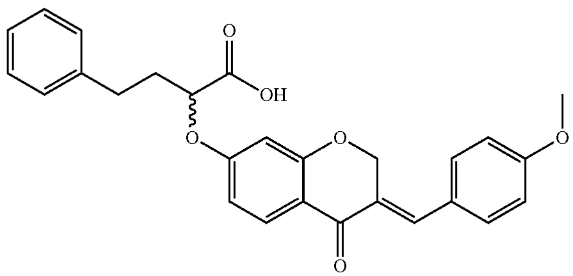 | 444.48 | | ¹H NMR (300 MHz, DMSO-d₆) δ ppm:): 2.03-2.23 (2 H, m); 2.66-2.84 (2 H, m); 3.82 (3 H, s); 4.67-4.84 (1 H, m); 5.40 (2 H, s); 6.32-6.76 (2 H, m); 6.83-7.51 (9 H, m); 7.58-7.99 (2 H, m). | |
| 151 | 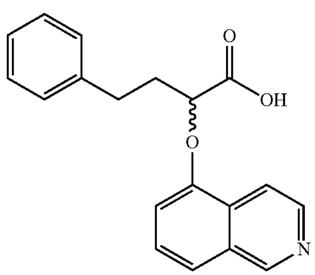 | 307.35 | | | ES+ M + H = 308.4 |
| 152 | 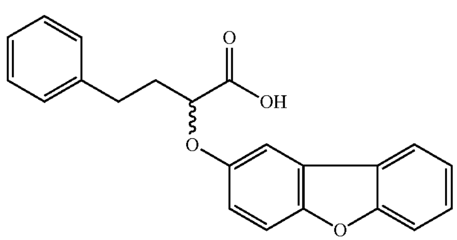 | 346.38 | 136° C. | | ES− 345.2 |

-continued

| Ex. | STRUCTURE | MW | M.p. | NMR DATA | MS DATA |
|---|---|---|---|---|---|
| 153 | 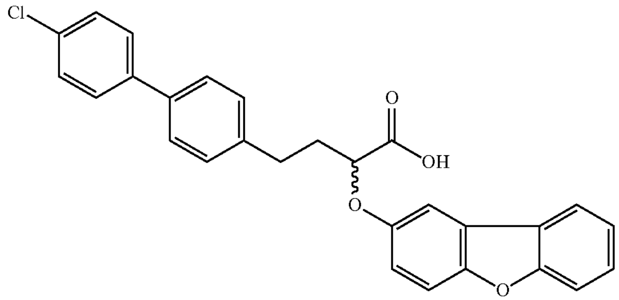 | 456.92 | | ¹H NMR (300 MHz, DMSO-d₆) δ ppm:): 2.10-2.37 (2 H, m); 2.79-2.99 (2 H, m); 4.67-4.88 (1 H, m); 6.98-7.16 (1 H, m); 7.24-7.74 (13 H, m); 8.00-8.18 (1 H, m); 12.99 (1 H, broad s). | ES- 455.2/457.2 1 chlorine atom |
| 154 | 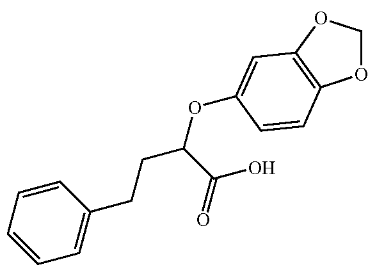 | 300.31 | | | ES+ 299.2 |
| 155 | 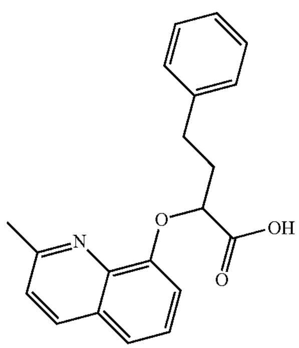 | 321.37 | | | ES+ 322.3 |

-continued
| Ex. | STRUCTURE | MW | M.p. | NMR DATA | MS DATA |
|---|---|---|---|---|---|
| 156 | 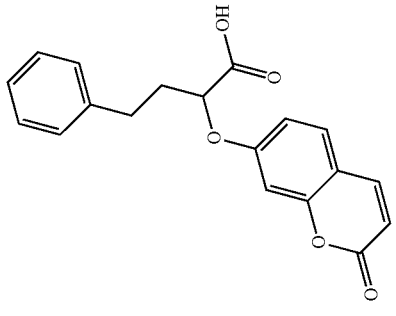 | 324.33 | | | ES– 322.1 |
| 157 | 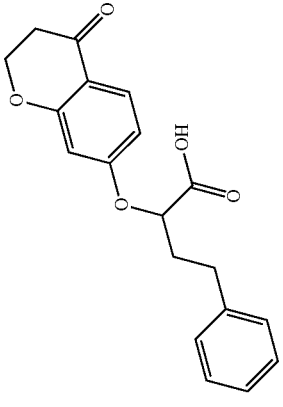 | 326.35 | | | ES– 325.1 |

-continued
| Ex. | STRUCTURE | MW | M.p. | NMR DATA | MS DATA |
|---|---|---|---|---|---|
| 158 | 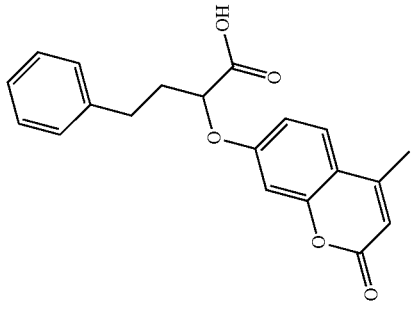 | 338.36 | | | ES– 327.1 |
| 159 | 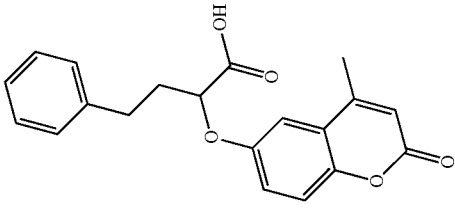 | 338.36 | | | ES– 337.2 |

| Ex. | STRUCTURE | MW | M.p. | NMR DATA | MS DATA |
|---|---|---|---|---|---|
| 160 | 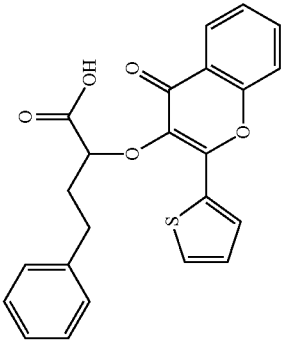 | 406.46 | | | ES− 405.1 |
| 161 | 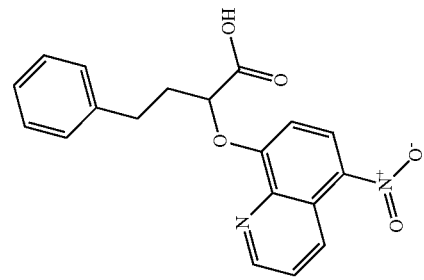 | 352.34 | | | ES+ 353.2 |

-continued
| Ex. | STRUCTURE | MW | M.p. | NMR DATA | MS DATA |
|---|---|---|---|---|---|
| 162 | 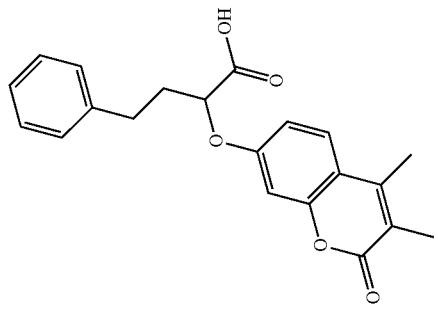 | 352.38 | | | ES– 351.2 |
| 163 | 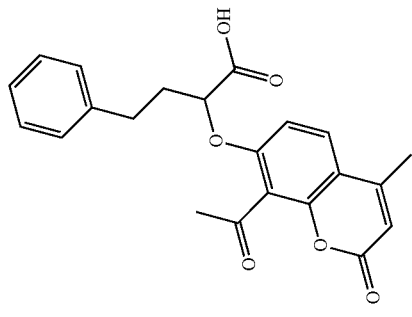 | 380.39 | | | ES– 337.1 |

-continued
| Ex. | STRUCTURE | MW | M.p. | NMR DATA | MS DATA |
|---|---|---|---|---|---|
| 164 | 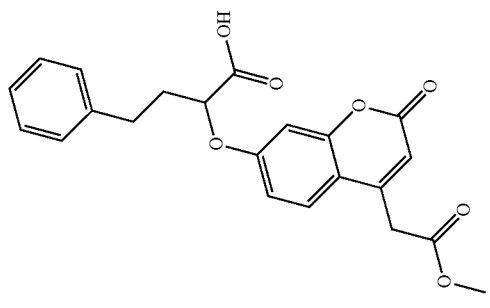 | 396.39 | | | ES– 395.1 |
| 165 | 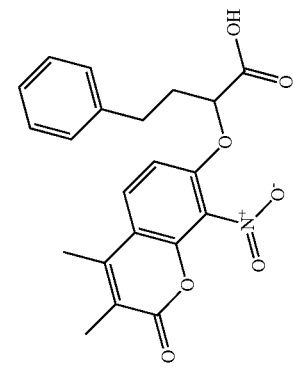 | 397.38 | | | ES– 396.1 |

-continued

| Ex. | STRUCTURE | MW | M.p. | NMR DATA | MS DATA |
|---|---|---|---|---|---|
| 166 | 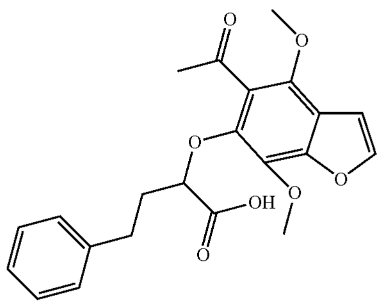 | 398.41 | | | ES- 397.2 |
| 167 | 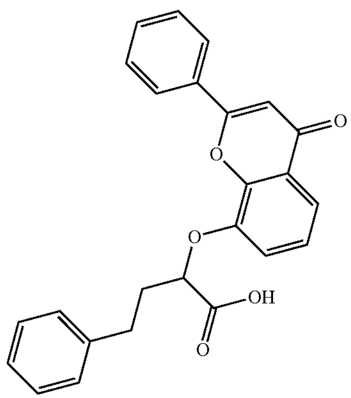 | 400.43 | | | ES- 399.1 |
| 168 | 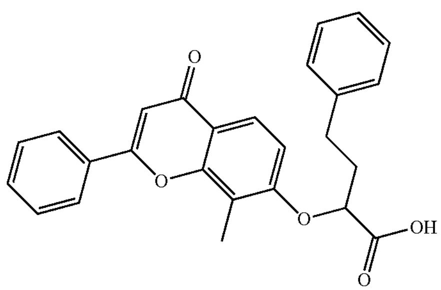 | 414.45 | | | ES+ 415.2 |

-continued

| Ex. | STRUCTURE | MW | M.p. | NMR DATA | MS DATA |
|---|---|---|---|---|---|
| 169 | 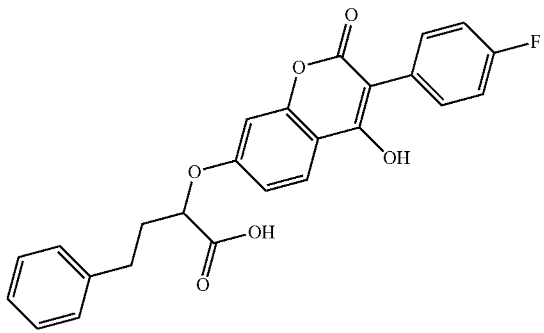 | 434.42 | | | ES– 433.2 |
| 170 | 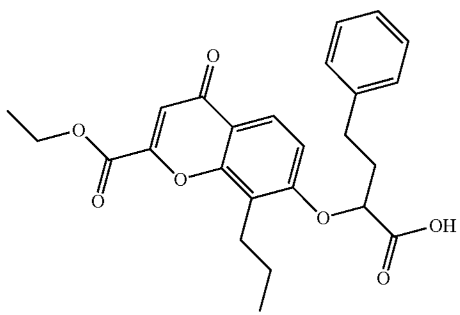 | 438.47 | | | ES– 437.2 |
| 171 | 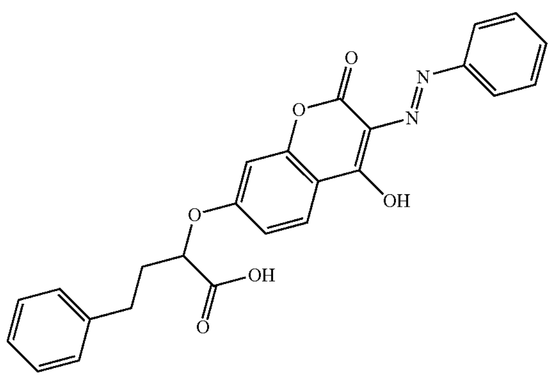 | 444.44 | | | ES– 443.2 |

-continued

| Ex. | STRUCTURE | MW | M.p. | NMR DATA | MS DATA |
|---|---|---|---|---|---|
| 172 | 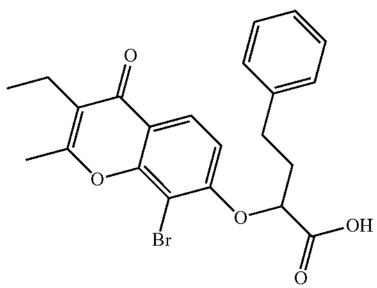 | 445.31 | | | ES− 443.1/445.1 1 bromine atom |
| 173 | 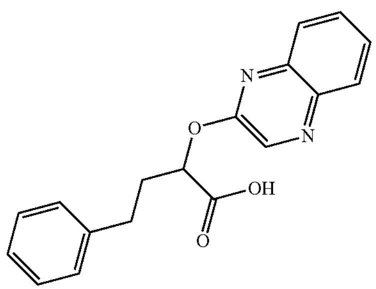 | 308.34 | | | ES− 307.2 ES+ 309.2 |
| 174 | 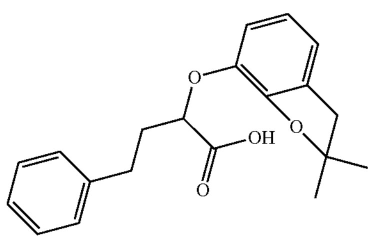 | 326.39 | | | ES− 325.2 |

-continued
| Ex. | STRUCTURE | MW | M.p. | NMR DATA | MS DATA |
|---|---|---|---|---|---|
| 175 | 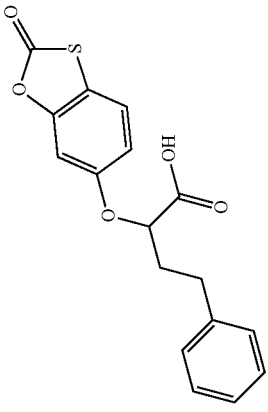 | 330.36 | | | ES- 329.1 |
| 176 | 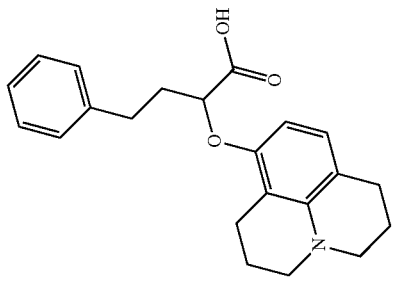 | 351.44 | | | ES- 350.2<br>ES+ 352.2 |

-continued

| Ex. | STRUCTURE | MW | M.p. | NMR DATA | MS DATA |
|---|---|---|---|---|---|
| 177 | 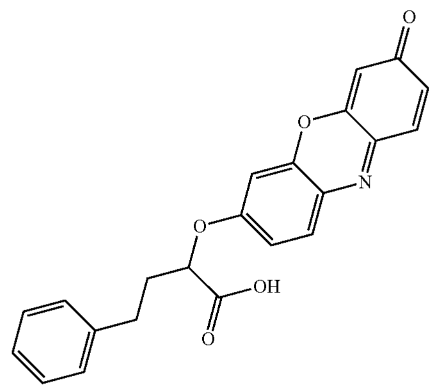 | 375.38 | | | ES− 374.2 |
| 178 | 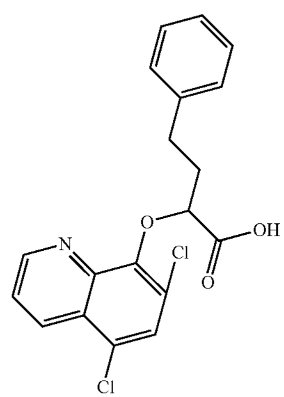 | 376.24 | | | ES+ 376.2/378.2 2 chlorine atoms |

| Ex. | STRUCTURE | MW | M.p. | NMR DATA | MS DATA |
|---|---|---|---|---|---|
| 179 | 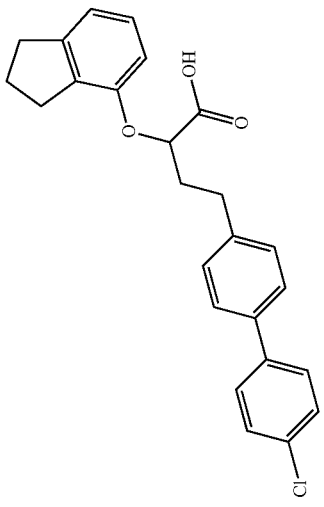 | 406.91 | | | ES- 405.2/407.2 1 chlorine atom |
| 180 | 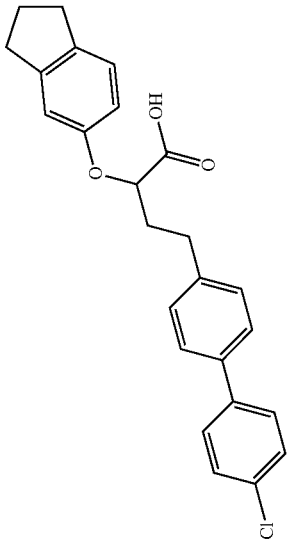 | 406.91 | | | ES- 405.2/407.2 1 chlorine atom |
| 181 | 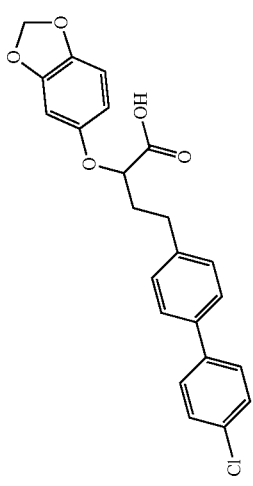 | 410.85 | | | ES- 409.1/411.1 1 chlorine atom |

-continued

| Ex. | STRUCTURE | MW | M.p. | NMR DATA | MS DATA |
|---|---|---|---|---|---|
| 182 | 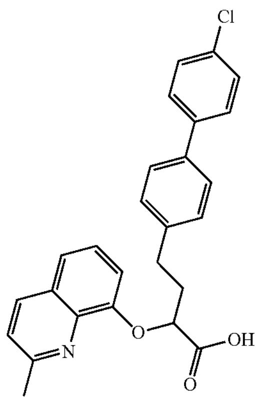 | 431.92 | | | ES– 430.2/432.2 1 chlorine atom |
| 183 | 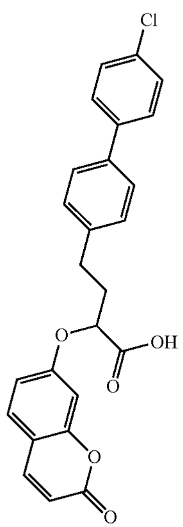 | 434.87 | | | ES– 433.2/435.2 1 chlorine atom |

-continued

| Ex. | STRUCTURE | MW | M.p. | NMR DATA | MS DATA |
|---|---|---|---|---|---|
| 184 | 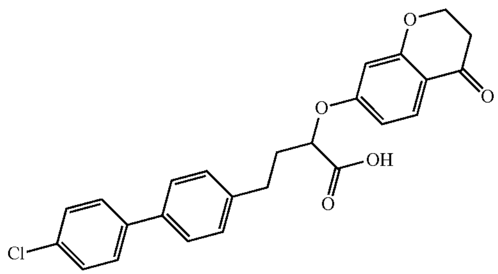 | 436.89 | | | ES- 435.2/437.2<br>1 chlorine atom |
| 185 | 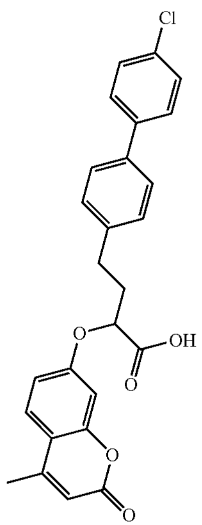 | 448.90 | | | ES- 447.2/449.2<br>1 chlorine atom |

-continued
| Ex. | STRUCTURE | MW | M.p. | NMR DATA | MS DATA |
|---|---|---|---|---|---|
| 186 | 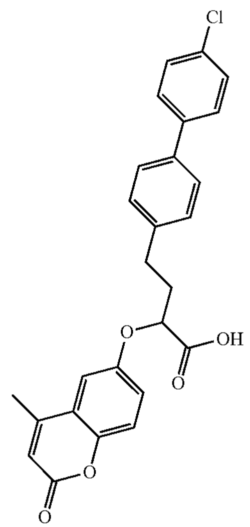 | 448.90 | | | ES- 447.2/449.2<br>1 chlorine atom |
| 187 | 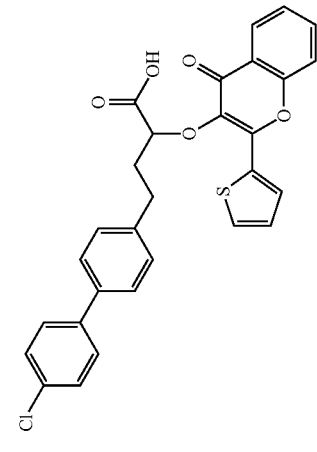 | 517.00 | | | ES- 515.3/517.3<br>1 chlorine atom |

-continued
| Ex. | STRUCTURE | MW | M.p. | NMR DATA | MS DATA |
|---|---|---|---|---|---|
| 188 | 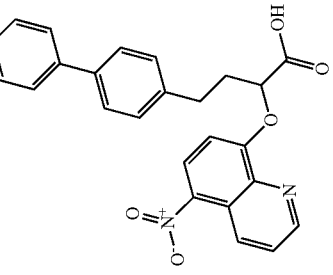 | 462.89 | | | ES– 461.2/463.2 1 chlorine atom |
| 189 | 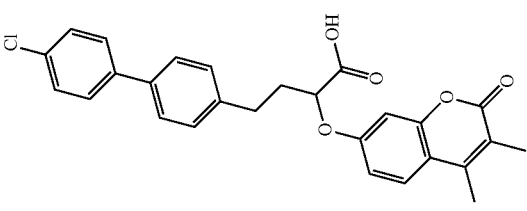 | 462.93 | | | ES– 461.2/463.2 1 chlorine atom |

| Ex. | STRUCTURE | MW | M.p. | NMR DATA | MS DATA |
|---|---|---|---|---|---|
| 190 | 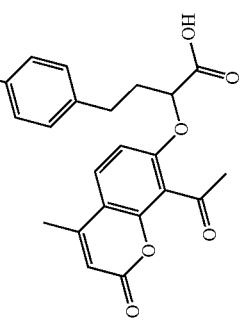 | 490.94 | | | ES– 489.2/491.2<br>1 chlorine atom |
| 191 | 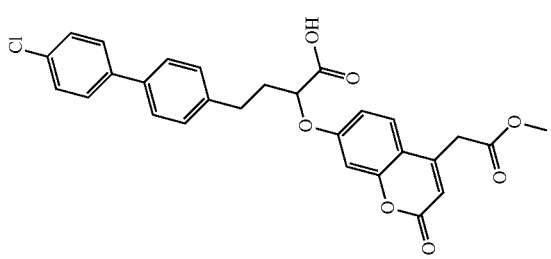 | 506.94 | | | ES– 505.2/507.2<br>1 chlorine atom |

| Ex. | STRUCTURE | MW | M.p. | NMR DATA | MS DATA |
|---|---|---|---|---|---|
| 192 | 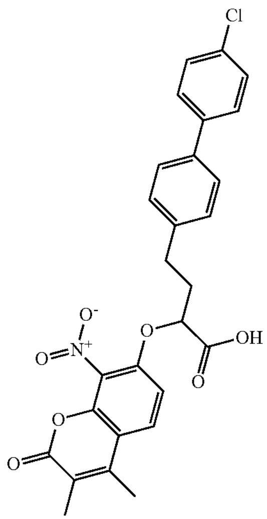 | 507.92 | | | ES− 506.2/508.2<br>1 chlorine atom |
| 193 | 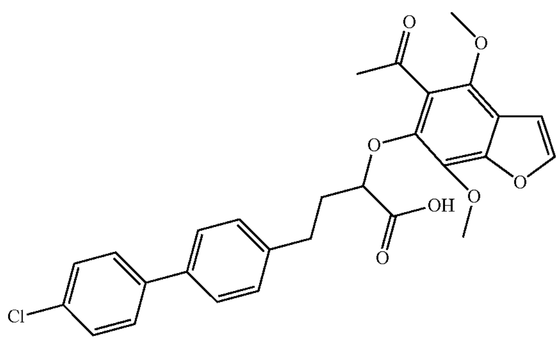 | 508.95 | | | ES− 507.3/509.3<br>1 chlorine atom |

| Ex. | STRUCTURE | MW | M.p. | NMR DATA | MS DATA |
|---|---|---|---|---|---|
| 194 | 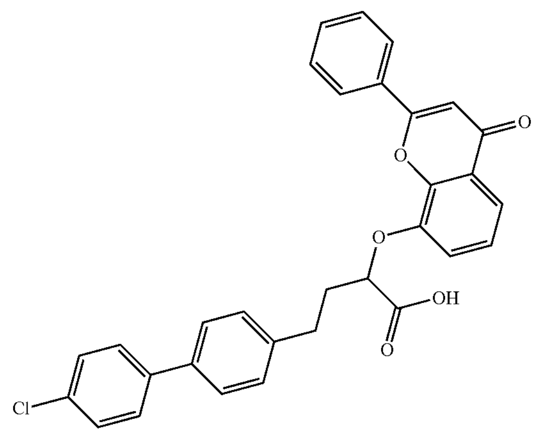 | 510.97 | | | ES− 509.3/511.3<br>1 chlorine atom |
| 195 | 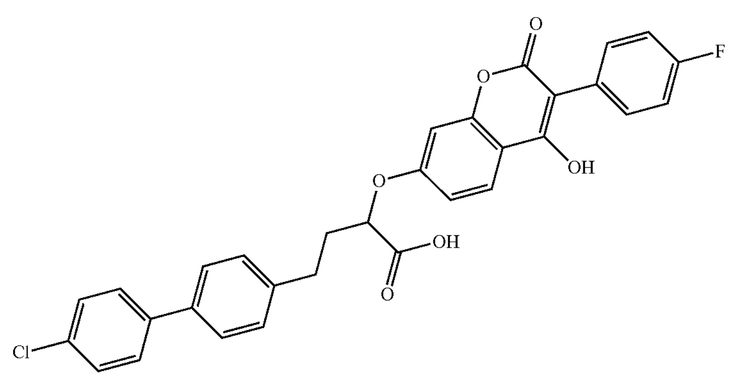 | 544.96 | | | ES+ 545.3/547.3<br>1 chlorine atom |

-continued

| Ex. | STRUCTURE | MW | M.p. | NMR DATA | MS DATA |
|---|---|---|---|---|---|
| 196 | 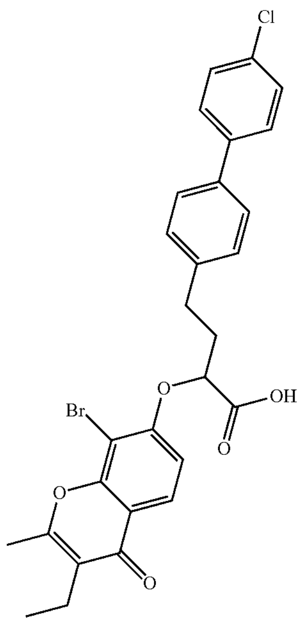 | 555.85 | | | ES− 509.2/511.2/513.2<br>1 chlorine atom and 1 bromine atom |
| 197 | 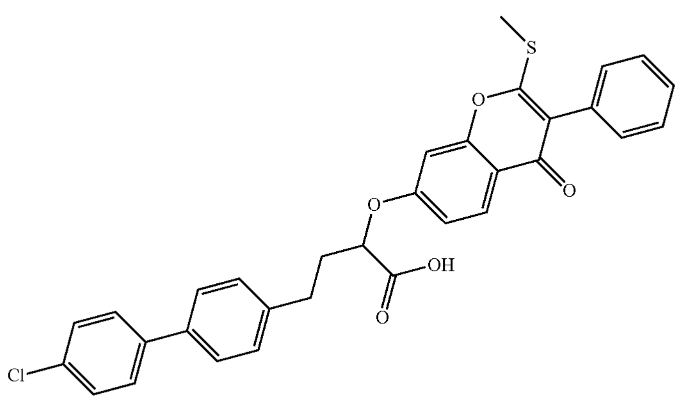 | 557.06 | | | ES− 555.2/557.2<br>1 chlorine atom |

-continued

| Ex. | STRUCTURE | MW | M.p. | NMR DATA | MS DATA |
|---|---|---|---|---|---|
| 198 | 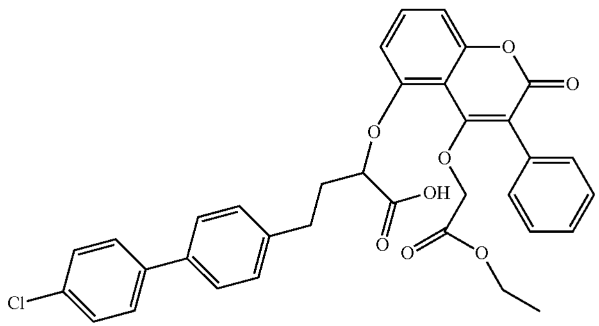 | 613.06 | | | ES+ 613.4/615.4 1 chlorine atom |
| 199 | 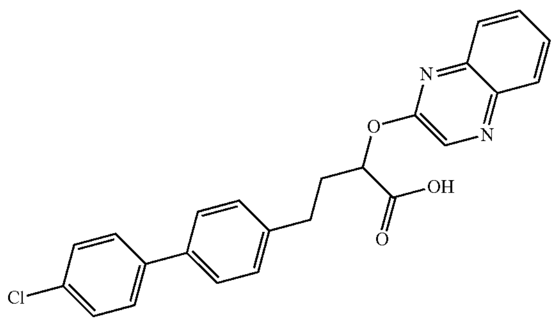 | 418.88 | | | ES− 417.2/419.2 1 chlorine atom |
| 200 | 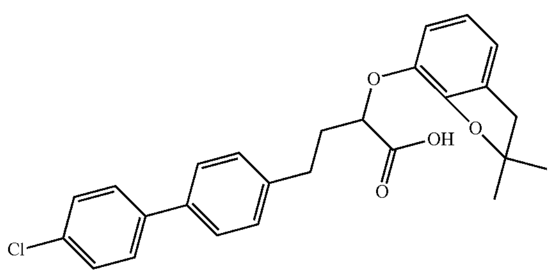 | 436.93 | | | ES+ 437.3/439.3 1 chlorine atom |

-continued
| Ex. | STRUCTURE | MW | M.p. | NMR DATA | MS DATA |
|---|---|---|---|---|---|
| 201 | 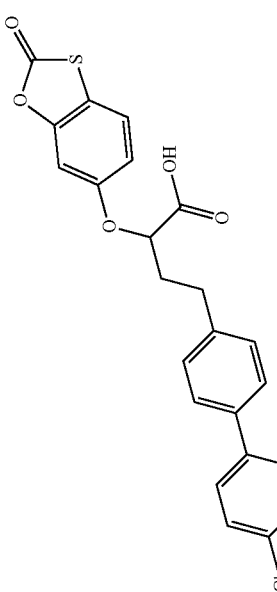 | 440.90 | | | ES− 439.2/441.2 1 chlorine atom |
| 202 | 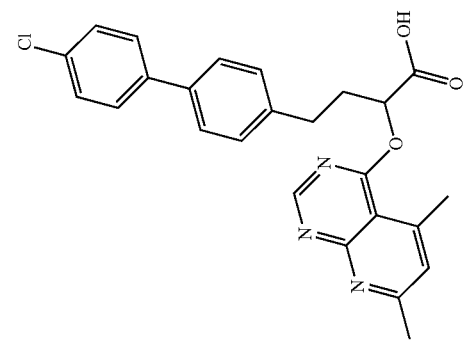 | 447.92 | | | ES+ 448.3/450.3 1 chlorine atom |

-continued
| Ex. | STRUCTURE | MW | M.p. | NMR DATA | MS DATA |
|---|---|---|---|---|---|
| 203 | 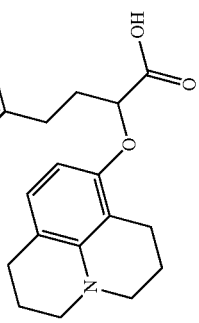 | 461.99 | | | ES– 460.3/462.3<br>1 chlorine atom |
| 204 | 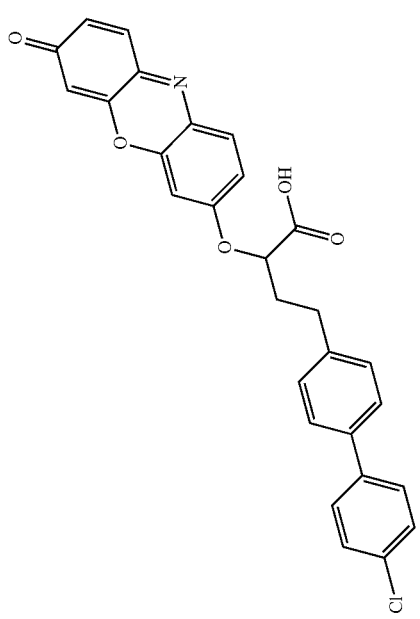 | 485.92 | | | ES– 484.2/486.2<br>1 chlorine atom |

-continued
| Ex. | STRUCTURE | MW | M.p. | NMR DATA | MS DATA |
|---|---|---|---|---|---|
| 205 | 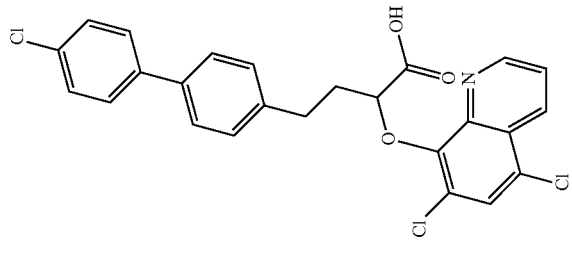 | 486.78 | | | ES- 484.1/486.1<br>1 chlorine atom |
| 206 | 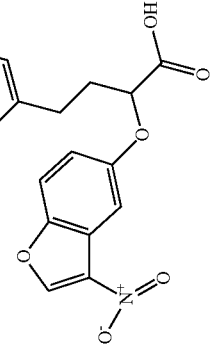 | 451.86 | | | ES- 450.2/452.2<br>1 chlorine atom |

| Ex. | STRUCTURE | MW | M.p. | NMR DATA | MS DATA |
|---|---|---|---|---|---|
| 207 | 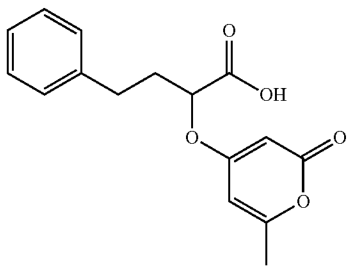 | 288.30 | 165° C. | ¹H NMR (300 MHz, DMSO-d6) δ ppm: 1.90-2.13 (2 H, m); 2.15 (3 H, s); 2.55-2.84 (2 H, m); 5.07-5.26 (1 H, m); 6.06 (1 H, s); 7.05-7.37 (5 H, m). | |
| 208 | 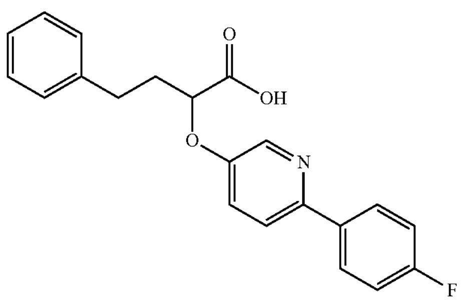 | 351.38 | | ¹H NMR (300 MHz, CDCl₃) δ ppm: 2.3 (m, 2 H) 2.9 (m, 2 H) 4.7 (t, J = 6.0 Hz, 1 H) 7.1 (m, 2 H) 7.2 (m, 3 H) 7.3 (m, 2 H) 7.4 (dd, J = 8.1, 2.4 Hz, 1 H) 7.5 (d, J = 8.7 Hz, 1 H) 7.8 (m, 2 H) 8.3 (d, J = 2.6 Hz, 1 H) | |
| 209 | 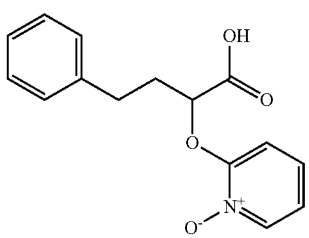 | 273.29 | | | ES+ 274.1 |

-continued

| Ex. | STRUCTURE | MW | M.p. | NMR DATA | MS DATA |
|---|---|---|---|---|---|
| 210 | 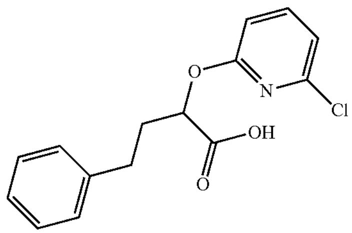 | 291.73 | | | ES− 290.2/292.2 1 chlorine atom |
| 211 | 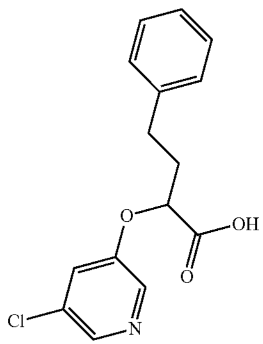 | 291.73 | | | ES+ 292.2/294.2 1 chlorine atom |
| 212 | 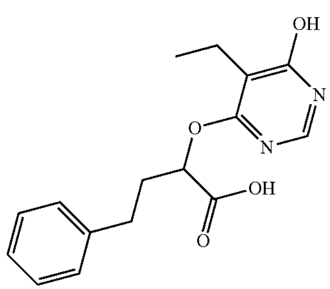 | 302.33 | | | ES− 301.2 |

-continued

| Ex. | STRUCTURE | MW | M.p. | NMR DATA | MS DATA |
|---|---|---|---|---|---|
| 213 | 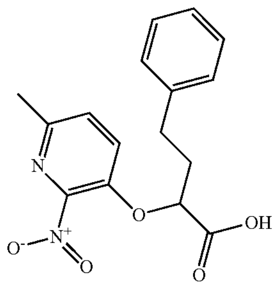 | 316.31 | | | ES− 315.2<br>ES+ 317.2 |
| 214 | 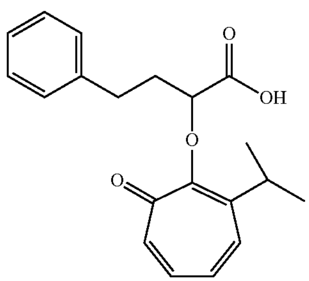 | 326.39 | | | ES− 325.2<br>ES+ 327.2 |
| 215 | 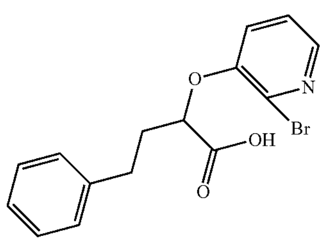 | 336.18 | | | ES− 334.1/336.1<br>ES+ 336.1/338.1 |

-continued

| Ex. | STRUCTURE | MW | M.p. | NMR DATA | MS DATA |
|---|---|---|---|---|---|
| 216 | 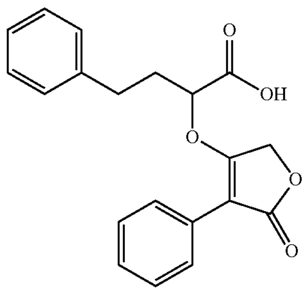 | 338.36 | | | ES− 337.1 |
| 217 | 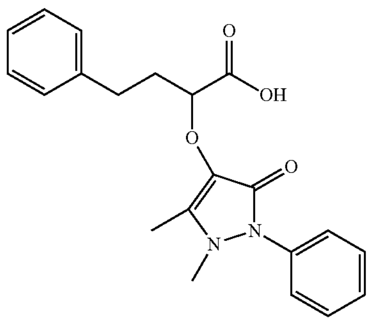 | 366.41 | | | ES− 365.2<br>ES+ 367.2 |
| 218 | 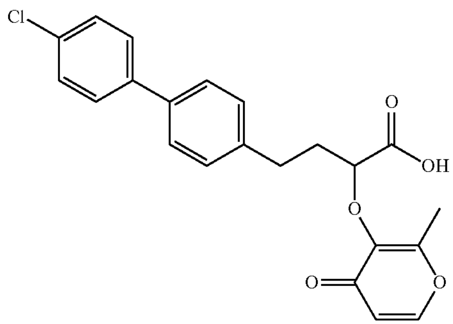 | 398.84 | | | ES− 397.1/399.1<br>1 chlorine atom |

-continued

| Ex. | STRUCTURE | MW | M.p. | NMR DATA | MS DATA |
|---|---|---|---|---|---|
| 219 | 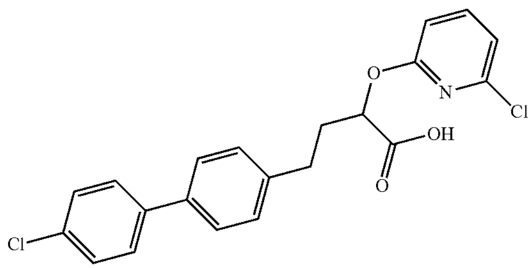 | 402.28 | | | ES- 400.1/403.1 1 chlorine atom |
| 220 | 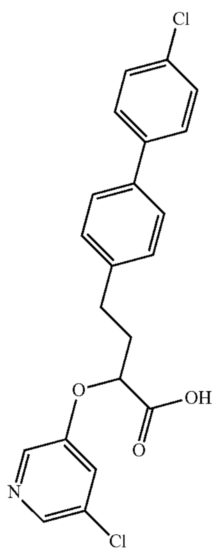 | 402.28 | | | ES- 400.1/403.1 1 chlorine atom |
| 221 | 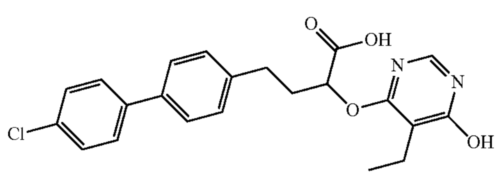 | 412.87 | | | ES- 411.3/415.3 1 chlorine atom |

-continued
| Ex. | STRUCTURE | MW | M.p. | NMR DATA | MS DATA |
|---|---|---|---|---|---|
| 222 | 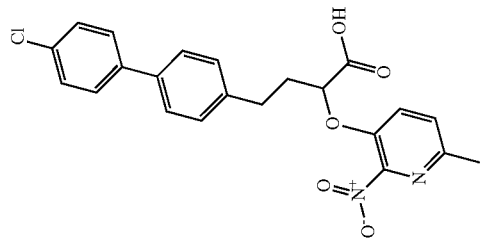 | 426.85 | | | ES− 425.2/427.2<br>1 chlorine atom |
| 223 | 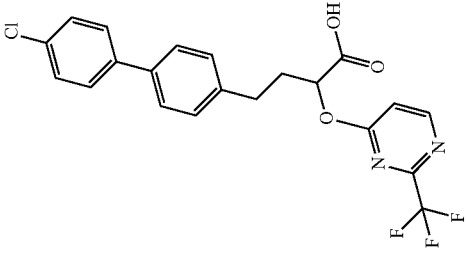 | 436.82 | | | ES− 435.2/437.2<br>1 chlorine atom |

-continued

| Ex. | STRUCTURE | MW | M.p. | NMR DATA | MS DATA |
|---|---|---|---|---|---|
| 224 | 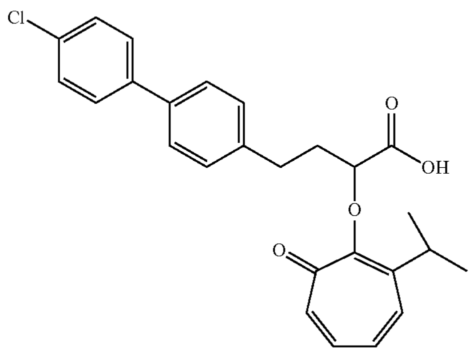 | 436.93 | | | ES- 435.2/437.2 1 chlorine atom |
| 225 | 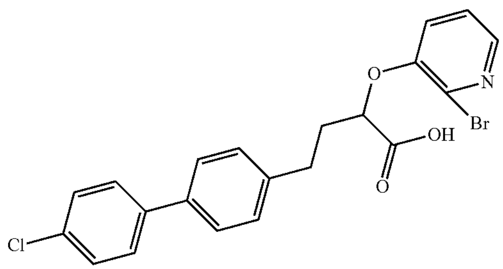 | 446.73 | | | ES- 441.1/443.1/ 445.1 1 chlorine atom and 1 bromine atom |
| 226 | 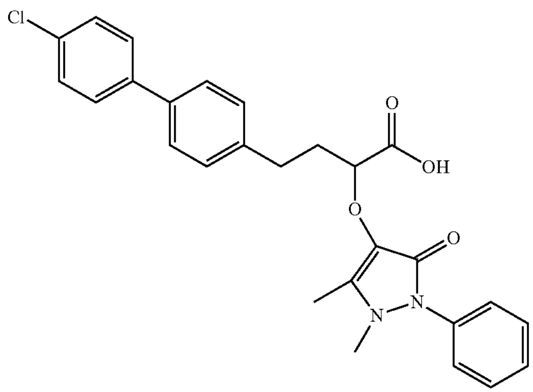 | 476.96 | | | ES- 475.3/477.3 1 chlorine atom |

| Ex. | STRUCTURE | MW | M.p. | NMR DATA | MS DATA |
|---|---|---|---|---|---|
| 227 | (4-bromophenyl-furan structure with carboxylic acid) | 325.16 | 102-104° C. | ¹H NMR (300 MHz, CDCl3): 2.15-2.46 (2 H, m); 2.72-3.03 (2 H, m); 4.49-4.70 (1 H, m); 5.87-6.08 (1 H, m); 6.14-6.36 (1 H, m); 6.61-6.86 (2 H, m); 7.18-7.50 (3 H, m). | |
| 228 | (trifluoromethylphenyl-furan structure with carboxylic acid) | 314.26 | 99-99.5° C. | ¹H NMR (300 MHz, CDCl3): 2.13-2.45 (2 H, m); 2.63-2.94 (2 H, m); 4.56-4.74 (1 H, m); 6.85-7.23 (5 H, m); 7.47-7.66 (2 H, m). | |
| 229 | (trifluoromethylphenyl-thiophene structure with carboxylic acid) | 330.32 | 116-118° C. | ¹H NMR (300 MHz, CDCl3): 2.21-2.51 (2 H, m); 2.96-3.25 (2 H, m); 4.62-4.80 (1 H, m); 6.70-7.01 (4 H, m); 7.06-7.20 (1 H, m); 7.42-7.68 (2 H, m). | |
| 230 | (methylthiazole-phenyl-fluorophenyl structure with carboxylic acid) | 371.43 | | ¹H NMR (300 MHz, CDCl₃) δ ppm: 2.3 (m, 2 H) 2.8 (s, 3 H) 3.0 (m, 2 H) 4.6 (dd, J = 7.7, 5.1 Hz, 1 H) 6.9 (d, J = 8.8 Hz, 2 H) 7.0 (m, 2 H) 7.2 (m, 3 H) 7.7 (d, J = 8.8 Hz, 2 H) 8.8 (s, 1 H) | |

Results

The activity of the compounds of the invention leading to a hypolipidaemiant and hypoglycaemiant effect was demonstrated in vitro and in vivo by performing the following tests.

Demonstration of the in vitro Activity

The measurement of the PPAR activation was performed according to a technique described by Lehmann et al. (*J. Biol. Chem.*, 270, (1995), 12953-12956).

CV-1 cells (monkey kidney cells) are co-transfected with an expression vector for the chimeric proteins PPARα-Gal4 or PPARγ-Gal4 and with a "reporter" plasmid that allows the expression of the luciferase gene placed under the control of a promoter comprising Gal4 response elements.

The cells are plated into 96-well microplates and co-transfected using a commercial reagent with the reporter plasmid (pG5-tk-pGL3) and the expression vector for the chimeric protein (PPARα-Gal4 or PPARγ-Gal4). After incubating for 4 hours, whole culture medium (comprising 10% foetal calf serum) is added to the wells. After 24 hours, the medium is removed and replaced with whole medium comprising the test products (50 μM final). The products are left in contact with the cells for 18 hours. The cells are then lysed and the luciferase activity is measured using a luminometer. A PPAR activation factor can then be calculated by means of activation of the expression of the reporter gene induced by the product (relative to the control cells that have not received any product).

By way of example, the compound of Example 18 at a concentration of 50 μM, activates the chimeric protein PPARα-Gal-4 by a factor of 16, and the chimeric protein PPARγ-Gal4 by a factor of 41. In the absence of the binding domain for the PPAR α or γ ligand (vector expressing Gal4 alone), the luciferase activity measured in the presence of this product is zero.

Demonstration of the in vivo Activity

The antidiabetic and hypolipidaemiant activity of the compounds according to the invention was determined orally on db/db mice.

15-week-old db/db mice are treated orally for 15 days with the compound of Example 18 (20 mg/kg/day). Each group studied comprises seven animals. After treatment for 15 days, retro-orbital samples are taken under mild anaesthesia and after fasting for four hours.

The following parameters were measured:

Assay of the glycaemia (glucose oxidase) and of the lipid parameters on the sera at D15 (COBAS): triglycerides, total cholesterol (CHOL), HDL cholesterol (HDL-C) and free fatty acids (FFA) (BioMérieux and Waco Chemicals assay kit).

The results obtained are given in the table below. The measurements reported represent mean values±standard error.

|  | Control | Example 18 | % var. |
|---|---|---|---|
| Glycaemia Mm | 27.1 ± 7.0 | 12.65 ± 7.0 | −53 ** |
| Triglycerides mM | 1.3 ± 0.3 | 0.77 ± 0.16 | −41 ** |
| HDL-C mM | 3.2 ± 0.2 | 3.53 ± 0.24 | +10 * |
| CHOL mM | 3.65 ± 0.2 | 4.57 ± 0.51 | +25 ** |
| FFA mM | 0.7 ± 0.1 | 0.42 ± 0.06 | −40 ** |

% var.: percentage of variation versus control.
Mann-Whitney test:
* $p < 0.05$ versus control
** $p < 0.01$ versus control These results demonstrate the antidiabetic and hypolipidaemiant activity of the compounds of the invention on triglycerides and free fatty acids. The marked increase in the level of HDL cholesterol with these same compounds should be noted.

The invention claimed is:

1. Compound of the formula (I):

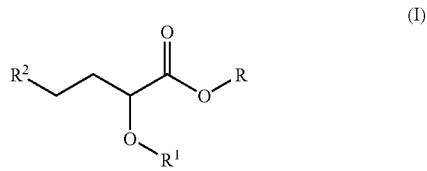

in which:

R is a hydrogen atom or a $C_1$-$C_{10}$ alkyl radical;

$R^1$ and $R^2$, which may be identical or different, are:

A.- either:

$R^1$ is:

a ($C_6$-$C_{18}$)aryl radical bearing from two to five identical or different substituents G;

a ($C_6$-$C_{18}$)aryl radical bearing a substituent G, itself comprising an optionally substituted ($C_6$-$C_{18}$)aryl radical and/or a saturated, unsaturated or aromatic, optionally substituted 5- to 8-membered monocyclic heterocyclic radical containing one or more O, N or S atoms;

an optionally substituted ($C_6$-$C_{18}$)aryl radical, fused to a saturated or unsaturated 5- to 8-membered monocyclic or polycyclic nucleus optionally containing one or more hetero atoms chosen from oxygen and sulfur, the said nucleus itself being optionally substituted;

an optionally substituted ($C_6$-$C_{18}$)aryl radical, fused to a saturated or unsaturated 6- to 8-membered monocyclic or polycyclic nucleus comprising at least one nitrogen atom as hetero atom, the said nucleus itself being optionally substituted; or a saturated, unsaturated or aromatic, 5- to 8-membered monocyclic heterocyclic radical containing one or more oxygen, nitrogen or sulphur atoms, optionally substituted by one or more of the following radicals; trifluoromethyl, a halogen atom, a $C_1$-$C_6$ alkylenediyl chain, a $C_1$-$C_6$ alkylenedioxy chain, nitro, cyano, ($C_1$-$C_{10}$)alkyl, ($C_2$-$C_{10}$)alkynyl, ($C_1$-$C_{10}$)alkylcarbonyl, ($C_1$-$C_{10}$)alkoxycarbonyl-A-, in which A represents ($C_1$-$C_6$)alkylene, ($C_2$-$C_8$)alkenylene or a bond, ($C_3$-$C_{10}$)cycloalkyl, trifluoromethoxy, di($C_3$-$C_{10}$)alkylamino, ($C_1$-$C_{10}$)alkoxy($C_3$-$C_{10}$)alkyl, ($C_1$-$C_{10}$)alkoxy, hydroxyl or oxo;

and, in this case, $R^2$ is:

a phenyl, naphthyl, anthryl or phenanthryl radical; or an optionally substituted 5- to 8-membered monocyclic aromatic heterocyclic radical containing one or more O, N or S atoms;

B.- or:

$R^2$ is:

an optionally substituted biphenyl radical; or;

an optionally substituted 5- to 8-membered monocyclic aromatic heterocyclic radical containing one or more O, N or S atoms;

and, in this case,
R¹ is:
an optionally substituted ($C_6$-$C_{18}$)aryl radical fused to a saturated or unsaturated 5- to 8-membered monocyclic or polycyclic nucleus optionally containing one or more hetero atoms chosen from oxygen and sulfur, the said nucleus itself being optionally substituted;

an optionally substituted ($C_6$-$C_{18}$)aryl radical fused to a saturated or unsaturated 6- to 8-membered monocyclic or polycyclic nucleus bearing at least one nitrogen atom as hetero atom, the said nucleus itself being optionally substituted; or a saturated, unsaturated or aromatic, 5- to 8-membered monocyclic heterocyclic radical containing one or more hetero atoms chosen from oxygen, nitrogen or sulfur, optionally substituted by one or more of the following radicals: trifluoromethyl, a halogen atom, a $C_1$-$C_8$ alkylenediyl chain, a $C_1$-$C_8$ alkylenedioxy chain nitro, cyano, ($C_1$-$C_{10}$)alkyl, ($C_3$-$C_{10}$)alkynyl, ($C_1$-$C_{10}$)alkylcarbonyl, ($C_1$-$C_{10}$) alkoxycarbonyl-A-, in which A represents ($C_1$-$C_8$) alkylene, ($C_2$-$C_8$)alkenylene or a bond, ($C_3$-$C_{10}$) cycloalkyl, trifluoromethoxy, di($C_1$-$C_{10}$) alkylamino, ($C_1$-$C_{10}$)alkoxy($C_3$-$C_{10}$)alkyl, ($C_1$-$C_{10}$)alkoxy, hydroxyl or oxo;

G is trifluoromethyl; a halogen atom; styryl; a monocyclic or, bicyclic aromatic heterocyclic radical comprising one or more O, N or S atoms, wherein the monocyclic aromatic heterocyclic radical is thiophene, imidazole, thiazole, isoxazole, isothiazole, furazane, pyridazine, pyrimidine, pyrazine, thiazines, oxazole, pyrazole, oxadiazole, triazole, thiadiazole, thianyl, triazine, pyran, thiopyran, morpholine, thiomorpholine, piperdine, thiazolidine, oxazolidine, tetrahydrothienyl, tetrahydrofuryl, pyrrolidine, isoxazolidine, imidazolidine and pyrazolidine, and wherein the bicyclic heteroaryls are indolizine, isoindole, indazole, benzimidazole, benzothiazole, benzoflurazane, benzothiofurazane, purine, quinoline, isoquinoline, cinnoline, phthalazine, quinazoline, quinoxaline, naphthyridine, pyrazolotriazine, pyrazolopyrimidine or pteridine, and optionally substituted by one or more radicals T as defined below; a group Het-CO—, in which Het represents an aromatic heterocyclic group, optionally substituted by one or more radicals T; a $C_1$-$C_6$ alkylenediyl chain; a $C_1$-$C_6$ alkylenedioxy chain; amino; nitro; cyano; ($C_1$-$C_{10}$)alkyl radical; ($C_2$-$C_6$)alkynyl radical; ($C_1$-$C_{10}$)alkylcarbonyl radical; ($C_1$-$C_{10}$) alkoxycarbonyl-A- radical, in which A represents ($C_1$-$C_6$)alkylene, ($C_2$-$C_6$)alkenylene radical or a bond; ($C_3$-$C_{10}$)cycloalkyl radical; trifluoromethoxy radical; di($C_1$-$C_{10}$)alkylamino radical; ($C_1$-$C_{10}$) alkoxy($C_1$-$C_{10}$)alkyl radical; ($C_1$-$C_{10}$)alkoxy radical; ($C_6$-$C_{18}$)aryloxy(CO)$_n$—radical, in which n is 0 or 1 and in which aryl is optionally substituted by one or more radicals T; ($C_6$-$C_{18}$)aryloxy(CO)$_n$-($C_2$-$C_6$)alkenyl radical, in which n is 0 or 1; ($C_6$-$C_{18}$)arylthio radical, in which aryl is optionally substituted by one or more radicals T; ($C_6$-$C_{18}$)aryloxy($C_1$-$C_{10}$)alkyl (CO)$_n$, in which n is 0 or 1 and in which aryl is optionally substituted by one or more radicals T; a saturated or unsaturated, monocyclic 5- to 8-membered heterocycle comprising one or more O, N or S atoms, optionally substituted by one or more radicals T; ($C_6$-$C_{18}$)arylcarbonyl radical optionally substituted by one or more radicals T; ($C_6$-$C_{18}$)arylcarbonyl-B-(CO)$_n$- radical, in which n is 0 or 1, where B represents ($C_1$-$C_6$)alkylene or ($C_2$-$C_6$)alkenylene and the aryl is optionally substituted by one or more radicals T; ($C_6$-$C_{18}$)aryl-C-(CO)$_n$- radical, in which n is 0 or 1, C represents ($C_1$-$C_6$)alkylene or ($C_2$-$C_6$)alkenylene and aryl is optionally substituted by one or more radicals T; or a ($C_2$-$C_{10}$)alkynyl radical; and T is a halogen atom; ($C_1$-$C_6$)alkyl; ($C_1$-$C_6$)alkoxy; nitro; carboxyl; ($C_1$-$C_6$)alkoxy -carboxyl; and T may represent oxo in the case where it substitutes a saturated or unsaturated heterocycle; or alternatively T represents ($C_1$-$C_6$)alkoxycarbonyl($C_1$-$C_6$)alkyl; or ($C_1$-$C_6$)alkylcarbonyl(($C_1$-$C_6$)alkyl)$_n$-, in which n is 0 or 1;

optical isomers thereof, or pharmaceutically acceptable addition salts thereof with acids or bases with the restriction that when R² represents a phenyl radical not substituted by an aromatic or heteroaromatic radical, then R¹ cannot represent a phenyl radical that is itself substituted by a phenyl or naphthyl radical.

2. Compound according to claim 1, in which R represents a hydrogen atom, R¹ and R² being as defined in claim 1, optical isomers thereof, or pharmaceutically acceptable addition salts thereof with acids or bases with the restriction that when R² represents a phenyl radical not substituted by an aromatic or heteroaromatic radical, then R¹ cannot represent a phenyl radical that is itself substituted by a phenyl or naphthyl radical.

3. Compound according to claim 1, in which R¹ represents a ($C_6$-$C_{18}$)aryl radical bearing a saturated, unsaturated or aromatic, optionally substituted 5- to 8-membered monocyclic heterocyclic radical containing one or more O, N or S atoms, or an aromatic bicyclic heterocyclic radical comprising one or more O, N or S atoms, optionally substituted by one or more radicals T, wherein the monocyclic heteroaryls are chosen from thiophene, imidazole, thiazole, isoxazole, isothiazole, furazane, pyridazine, pyrimidine, pyrazine, thiazines, oxazole, pyrazole, oxadiazole, triazole, thiadiazole, thienyl, triazine, pyran, thiopyran, morpholine, thiomorpholine, piperdine, thiazolidine, oxazolidine, tetrahydrothienyl, tetrahydrofuryl, pyrrolidine, isoxazolidine, imidazolidine and pyrazolidine, and wherein the bicyclic heteroaryls are chosen from indolizine, isoindole, benzothiophene, indazole, benzimidazole, benzothiazole, benzofurazane, benzothiofurazane, purine, quinoline, isoquinoline, cinnoline, phthalazine, quinazoline, quinoxaline, naphthyridine, pyrazolotriazine, pyrazolopyrimidine and oteridine; and R² chosen from:
a phenyl, naphthyl, anthryl and phenathryl and
an optionally substituted 5- to 8-membered monocyclic aromatic heterocyclic radical containing one or more O, N or S atoms;

R being as defined in claim 1,
optical isomers thereof, or pharmaceutically acceptable addition salts thereof with acids or bases, with the restriction that when R² represents a phenyl radical not substituted by an aromatic or heteroaromatic radical, then R¹ cannot represent a phenyl radical that is itself substituted by a phenyl or naphthyl radical.

4. Compound according to claim 1, in which R² represents an optionally substituted halogenated biphenyl radical, and R¹ is:
an optionally substituted ($C_6$-$C_{18}$)aryl radical fused to a saturated or unsaturated 5- to 8-membered monocyclic or polycyclic nucleus optionally containing one or more hetero atoms chosen from oxygen and sulfur, the said nucleus itself being optionally substituted;

an optionally substituted ($C_6$-$C_{18}$)aryl radical fused to a saturated or unsaturated 6- to 8-membered monocyclic or polycyclic nucleus comprising at least one nitrogen atom as hetero atom, the said nucleus itself being optionally substituted; or a saturated, unsaturated or aromatic, optionally substituted 5- to 8-membered monocyclic heterocyclic radical containing one or more O, N or S atoms, optionally substituted by one or more of the following radicals: trifluoromethyl, a halogen atom, a $C_1$-$C_6$ alkylenediyl chain, a $C_1$-$C_6$ alkylenedioxy chain, nitro, cyano, ($C_1$-$C_{10}$)alkyl, ($C_2$-$C_{10}$)alkynyl, ($C_1$-$C_{10}$)alkylcarbonyl, ($C_1$-$C_{10}$)alkoxycarbonyl-A-, in which A represents ($C_1$-$C_6$)alkylene, ($C_2$-$C_6$)alkenylene or a bond, ($C_3$-$C_{10}$)alkoxy($C_1$-$C_{10}$) cycloalkyl, trifluoromethoxy, di($C_1$-$C_{10}$)alkylamino, ($C_1$-$C_{10}$)alkoxy($C_1$-$C_{10}$) alkyl, ($C_1$-$C_{10}$)alkoxy, hydroxyl or oxo;

R being as defined in claim 1, optical isomers thereof, or pharmaceutically acceptable addition salts thereof with acids or bases.

5. Compound according to claim 1, which is:
(2S)-2- [4-(5-chlorothien-2-yl)phenoxy]-4-phenylbutanoic acid;
2-{2-[3-(4-chlorophenyl)acryloyl]-4-methylphenoxy}-4-phenylbutanoic acid;
(2S)-2-[4-(benzo[b]thiophen-2-yl)phenoxy]-4-phenylbutanoic acid; (2S)-2-[4-(benzo[b]thiophen-3-yl)phenoxy)-4-phenylbutanoic acid;
4-(2-fluorophenyl)-2-[4-(2-methylthiazol-4-yl)phenoxy] butanoic acid;
4-(4'-chlorobiphenyl-4-yl)-2-(4-nitrophenoxy)butanoic acid;
4-(4-fluorophenyl)-2-[4- (2-methylthiazol-4-yl)phenoxy] butanoic acid; or
(2S)-2-(4-furan-2-ylphenoxy)-4-phenylbutanoic acid.

6. Process for the preparation of a compound of formula I according to claim 1, by reaction of a compound of the formula (II) with an alcohol of the formula $R^1$—OH according to the following reaction scheme:

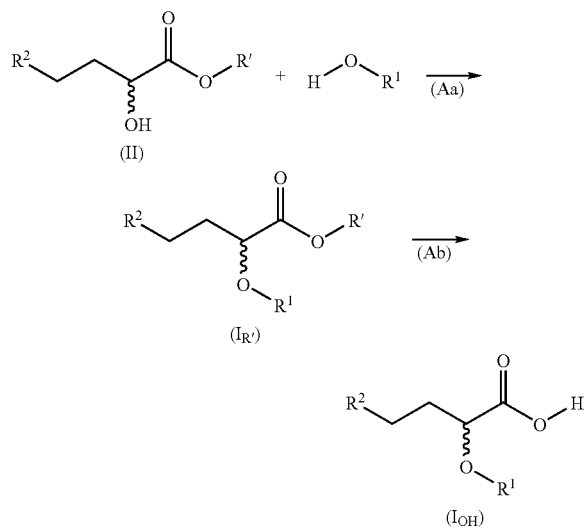

(Aa): THF/PPh$_3$/DIAD/room temp.
(Ab): EtOH/KOH/H$_2$O reflux in which reaction scheme $R^1$ $R^2$ as defined in claim 1, R' represents R as defined above, with the exception of hydrogen, the compound ($I_{R'}$) being the compound of the formula (I) in which R represents a $C_1$-$C_{10}$ alkyl radical, as defined above, and the compound ($I_{OH}$) being the compound of the formula (I) in which R represents —H.

7. Process for the preparation of a compound of formula I according to claim 1, in which $R^1$ represents an aryl radical substituted by a radical G, according to the following reaction scheme, a first step being performed in a polar aprotic solvent in the presence of a palladium 0 complex and a base; a second step being an optional saponification reaction:

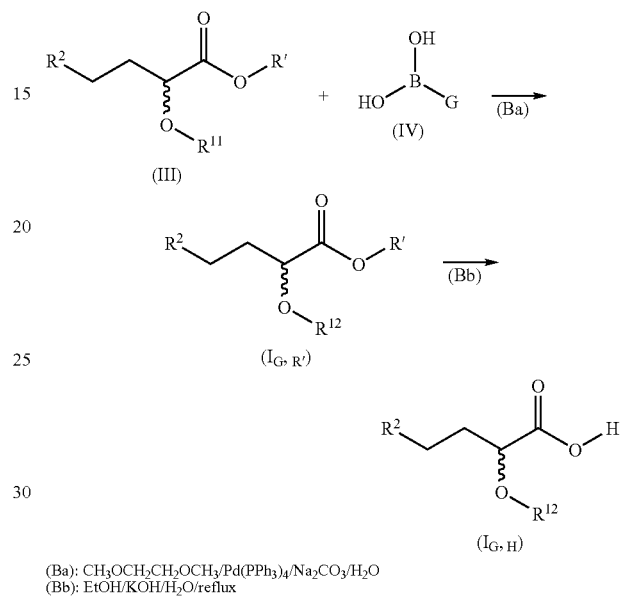

(Ba): CH$_3$OCH$_2$CH$_2$OCH$_3$/Pd(PPh$_3$)$_4$/Na$_2$CO$_3$/H$_2$O
(Bb): EtOH/KOH/H$_2$O/reflux in which reaction scheme:
$R^2$ is as defined in claim 1;
R' represents R, as defined in claim 1, with the exception of hydrogen;
$R^{11}$ represents $R^1$, as defined in claim 1, bearing a group that is reactive with the compound of the formula (IV) which is a bromine or iodine atom or a CF$_3$SO$_3$— radical, and
$R^{12}$ represents $R^{11}$, in which the group that is reactive with the compound of the formula (IV) has been substituted by the radical G.

8. Process for the preparation of a compound of formula I according to claim 1, using compounds grafted onto resin, according to the following reaction scheme:

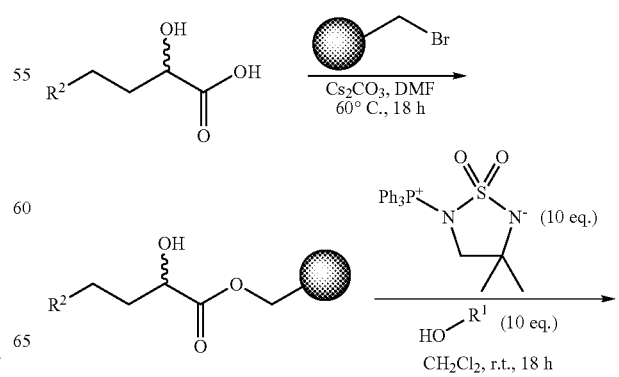

-continued

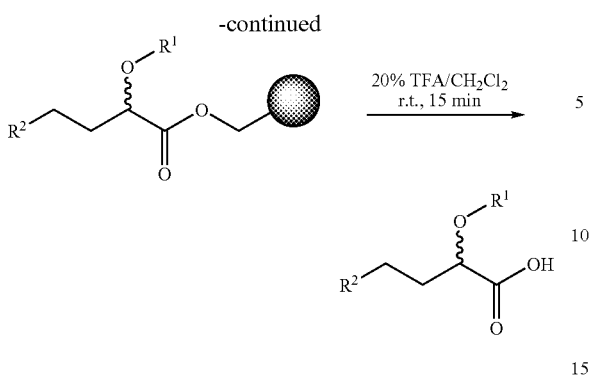

in which scheme $R^1$ and $R^2$ are as defined in claim 1,
this process comprising the steps of grafting a resin onto an α-hydroxy acid, which is then placed in contact with an alcohol of the formula $R^1$—OH, $R^1$ being as defined for formula (I), in the presence of a phosphine, the reaction being performed, at room temperature, for a time that may range from one to several hours, the resin then being detached from the substrate to give the compound of the formula (I) in which R represents hydrogen, which compound can be optionally converted into a compound of the formula (I) in which R is as defined in the general formula (I), with the exception of hydrogen.

9. Pharmaceutical composition comprising a pharmaceutically effective amount of at least one compound according to claim 1, in combination with one or more pharmaceutically acceptable vehicles.

10. A method for treating dyslipidaemia, atherosclerosis or diabetes comprising administering to a patient a compound of the formula (I) according to claim 1.

11. A method for treating diabetes, dyslipidemia and/or atherosclerosis, comprising administering to a patient a compound of the formula (1):

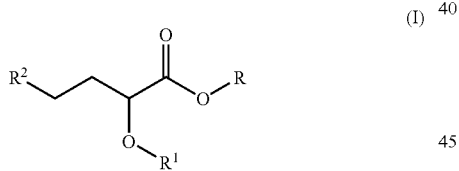

in which
R is a hydrogen atom or a $C_1$-$C_{10}$ alkyl radical;
$R^1$ and $R^2$, which may be identical or different, are:
A.-either:
  $R^1$ is:
    a ($C_6$-$C_{18}$)aryl radical bearing from two to five identical or different substituents G;
    a ($C_6$-$C_{18}$)aryl radical bearing a substituent G, itself comprising an optionally substituted ($C_6$-$C_{18}$)aryl radical and/or a saturated, unsaturated or aromatic, optionally substituted 5- to 8-membered monocyclic heterocyclic radical containing one or more hetero atoms chosen from O, N and S;
    an optionally substituted ($C_6$-$C_{18}$)aryl radical, fused to a saturated or unsaturated 5- to 8-membered monocyclic or polycyclic nucleus optionally containing one or more hetero atoms chosen from oxygen and sulfur, the said nucleus itself being optionally substituted;
    an optionally substituted ($C_6$-$C_{18}$)aryl radical, fused to a saturated or unsaturated 6- to 8-membered monocyclic or polycyclic nucleus comprising at least one nitrogen atom as hetero atom, the said nucleus itself being optionally substituted; or
    a saturated, unsaturated or aromatic, optionally substituted 5- to 8-membered monocyclic heterocyclic radical containing one or more oxygen, nitrogen or sulphur atoms;
and, in this case,
  $R^2$ is:
    a ($C_6$-$C_{18}$)aryl radical, which is optionally substituted and/or optionally fused to a saturated or unsaturated 5- to 8-membered monocyclic or polycyclic nucleus optionally containing one or more O, N or S atoms, said nucleus itself being optionally substituted; and
    an optionally substituted 5- to 8-membered monocyclic aromatic heterocyclic radical containing one or more O, N or S atoms; or
B.-
  $R^2$ is:
    a ($C_6$-$C_{18}$)aryl radical substituted by a ($C_6$-$C_{18}$)aryl radical, which is itself optionally substituted and/or optionally fused to a saturated or unsaturated 5- to 8-membered monocyclic or polycyclic nucleus optionally containing one or more O, N or S atoms, said nucleus itself being optionally substituted; and
    an optionally substituted 5- to 8-membered monocyclic aromatic heterocyclic radical containing one or more O, N or S atoms;
and, in this case,
  $R^1$ is:
    an optionally substituted ($C_6$-$C_{18}$)aryl radical fused to a saturated or unsaturated 5- to 8-membered monocyclic or polycyclic nucleus optionally containing one or more oxygen or sulphur atoms, said nucleus itself being optionally substituted;
    an optionally substituted ($C_6$-$C_{18}$)aryl radical fused to a saturated or unsaturated 6- to 8-membered monocyclic or polycyclic nucleus bearing at least one nitrogen atom, said nucleus itself being optionally substituted; and
    a saturated, unsaturated or aromatic, optionally substituted 5- to 8-membered monocyclic heterocyclic radical containing one or more oxygen, nitrogen or sulphur atoms;
  G is trifluoromethyl; a halogen atom; styryl; a monocyclic, bicyclic or tricyclic aromatic heterocyclic radical comprising one or more O, N or S atoms, and optionally substituted by one or more radicals T as defined below; a group Het-CO—, in which Het represents an aromatic heterocyclic group, optionally substituted by one or more radicals T; a $C_1$-$C_6$ alkylenediyl chain; a $C_1$-$C_6$ alkylenedioxy chain; amino; nitro; cyano; ($C_1$-$C_{10}$)alkyl radical; ($C_2$-$C_6$)alkynyl radical; ($C_1$-$C_{10}$) alkylcarbonyl radical; ($C_1$-$C_{10}$)alkoxycarbonyl-A- radical, in which A represents ($C_1$-$C_6$) alkylene, ($C_2$-$C_6$)alkenylene radical or a bond; ($C_3$-$C_{10}$)cycloalkyl radical; trifluoromethoxy radical; di($C_1$-$C_{10}$) alkylamino radical; ($C_1$-$C_{10}$)alkoxy($C_1$-$C_{10}$)alkyl radical; ($C_1$-$C_{10}$)alkoxy radical; ($C_6$-$C_{18}$)aryl radical optionally substituted by one or more radicals T; ($C_6$-$C_{18}$)aryl($C_1$-$C_{10}$)alkoxy -(CO)$_n$- radical, in which n is 0 or 1 and in which aryl is optionally substituted by one or more radicals T; ($C_6$-$C_{18}$)aryloxy(CO)$_n$- radical, in which n is 0 or 1 and in which aryl is optionally substituted by one or more radicals T; $(C_6-C_{18})$aryloxy$(CO)_n$-$(C_2-C_6)$alkenyl radical, in which n is 0 or 1; $(C_6-C_{18})$arylthio radical, in which aryl is optionally substituted by one or more radicals T; $(C_6-C_{18})$aryloxy$(C_1-C_{10})$alkyl$(CO)_n$, in which n is 0 or 1 and in which aryl is optionally substituted by one or more radicals T; a saturated or unsaturated, monocyclic 5- to 8-membered heterocycle comprising one or more O, N or S atoms, optionally substituted by one or more radicals T; $(C_6-C_{18})$arylcarbonyl radical optionally substituted by one or more radicals T; $(C_6-C_{18})$arylcarbonyl-B-$(CO)_n$- radical, in which n is 0 or 1, where B represents $(C_1-C_6)$alkylene or $(C_2-C_6)$alkenylene and the aryl is optionally substituted by one or more radicals T; $(C_6-C_{18})$aryl-C -$(CO)_n$- radical, in which n is 0 or 1, C represents $(C_1-C_6)$alkylene or $(C_2-C_6)$alkenylene and aryl is optionally substituted by one or more radicals T; $(C_6-C_{18})$aryl radical fused to a saturated or unsaturated heterocycle as defined above, optionally substituted by one or more radicals T; or a $(C_2-C_{10})$alkynyl radical; and T is a halogen atom; $(C_6-C_{18})$aryl; $(C_1-C_6)$alkyl; $(C_1-C_6)$alkoxy; nitro; carboxyl; or $(C_1-C_6)$alkoxycarboxyl; or T may represent oxo in the case where it substitutes a saturated or unsaturated heterocycle; or alternatively T represents $(C_1-C_6)$alkoxycarbonyl $(C_1-C_6)$alkyl; or $(C_1-C_6)$alkylcarbonyl$((C_1-C_6)$alkyl$)_n$-, in which n is 0 or 1;

optical isomers thereof, or pharmaceutically acceptable addition salts thereof with acids or bases with the restriction that when $R^2$ represents a phenyl radical not substituted by an aromatic or heteroaromatic radical, then $R^1$ cannot represent a phenyl radical that is itself substituted by a phenyl or naphthyl radical.

\* \* \* \* \*